US012761209B2

(12) United States Patent
Kshitiz et al.

(10) Patent No.: US 12,761,209 B2
(45) Date of Patent: Oct. 13, 2026

(54) DEVICES AND METHODS TO INDUCE ADULT TYPE MATURATION OF HUMAN PLURIPOTENT STEM CELL DERIVED CARDIOMYOCYTES

(71) Applicants: University of Connecticut, Farmington, CT (US); The Regents of the University of California, Oakland, CA (US)

(72) Inventors: Kshitiz, Farmington, CT (US); Junaid Afzal, Farmington, CT (US); Wenqiang Du, Farmington, CT (US); Yasir Suhail, Farmington, CT (US)

(73) Assignees: UNIVERSITY OF CONNECTICUT, Farmington, CT (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 700 days.

(21) Appl. No.: 18/184,851

(22) Filed: Mar. 16, 2023

(65) Prior Publication Data

US 2023/0296590 A1 Sep. 21, 2023

Related U.S. Application Data

(60) Provisional application No. 63/321,393, filed on Mar. 18, 2022.

(51) Int. Cl.

*G01N 33/50* (2006.01)
*C12N 5/077* (2010.01)

(52) U.S. Cl.

CPC ....... *G01N 33/5082* (2013.01); *C12N 5/0657* (2013.01); *C12N 2500/38* (2013.01); *C12N 2501/33* (2013.01); *C12N 2506/45* (2013.01); *C12N 2513/00* (2013.01); *C12N 2533/52* (2013.01); *C12N 2533/54* (2013.01); *C12N 2535/10* (2013.01)

(58) Field of Classification Search

None
See application file for complete search history.

(56) References Cited

U.S. PATENT DOCUMENTS 10,435,734 B2 * 10/2019 Kim .................. G01N 33/5002

OTHER PUBLICATIONS

Jafarkhani, Mahboubeh; et al; "Strategies for directing cells into building functional hearts and parts" Biomaterials Science, 6, 1664-1690, 2018 (Year: 2018).*

Schussler, Olivier; et al; "Possible Treatment of Myocardial Infarct Based on Tissue Engineering Using a Cellularized Solid Collagen Scaffold Functionalized with Arg-Glyc-Asp (RGD) Peptide" International Journal of Molecular Sciences, 22, 12563, 2021 (Year: 2021).*

Salabei, J.K., Gibb, A.A., and Hill, B.G. (2014). Comprehensive measurement of respiratory activity in permeabilized cells using extracellular flux analysis. Nat Protoc 9, 421-438.

(Continued)

*Primary Examiner* — David W Berke-Schlessel

(74) *Attorney, Agent, or Firm* — McDonnell, Boehnen, Hulbert & Berghoff, LLP

(57) ABSTRACT

Disclosed are constructs and methods to accelerate maturation of human pluripotent stem cell derived cardiomyocytes by maintaining them on a Cardiac Mimetic Matrix (CMM) substrate.

16 Claims, 65 Drawing Sheets

Specification includes a Sequence Listing.

(56) References Cited

OTHER PUBLICATIONS

Santos, C.X., Anilkumar, N., Zhang, M., Brewer, A.C., and Shah, A.M. (2011). Redox signaling in cardiac myocytes. Free Radic Biol Med 50, 777-793.
Sartiani, L., Bettiol, E., Stillitano, F., Mugelli, A., Cerbai, E., and Jaconi, M.E. (2007). Developmental changes in cardiomyocytes differentiated from human embryonic stem cells: a molecular and electrophysiological approach. Stem Cells 25, 1136-1144.
Schwach, V., and Passier, R. (2019). Native cardiac environment and its impact on engineering cardiac tissue, Biomater. Sci., 7, 3566-3580.
Schwer, B., and Verdin, E. (2008). Conserved metabolic regulatory functions of sirtuins. Cell metabolism 7, 104-112.
Sewanan, L.R., Schwan, J., Kluger, J., Park, J., Jacoby, D.L., Qyang, Y., and Campbell, S.G. (2019). Extracellular Matrix From Hypertrophic Myocardium Provokes Impaired Twitch Dynamics in Healthy Cardiomyocytes. JACC Basic Transl Sci 4, 495-505.
Shadrin, I.Y., Allen, B.W., Qian, Y., Jackman, C.P., Carlson, A.L., Juhas, M.E., and Bursac, N. (2017). Cardiopatch platform enables maturation and scale-up of human pluripotent stem cell-derived engineered heart tissues. Nat Commun 8, 1825.
Shao, D., Kolwicz, S.C., Jr., Wang, P., Roe, N.D., Villet, O., Nishi, K., Hsu, Y.A., Flint, G.V., Caudal, A., Wang, W., et al. (2020). Increasing Fatty Acid Oxidation Prevents High-Fat Diet-Induced Cardiomyopathy Through Regulating Parkin-Mediated Mitophagy. Circulation 142, 983-997.
Shi, M., Tien, N.T., de Haan, L., Louisse, J., Rietjens, I., and Bouwmeester, H. (2020). Evaluation of in vitro models of stem cell-derived cardiomyocytes to screen for potential cardiotoxicity of chemicals. Toxicol In Vitro 67, 104891.
Silva, A.C., Pereira, C., Fonseca, A., Pinto-do, O.P., and Nascimento, D.S. (2020). Bearing My Heart: The Role of Extracellular Matrix on Cardiac Development, Homeostasis, and Injury Response. Frontiers in cell and developmental biology 8, 621644.
Slenter, D.N., Kutmon, M., Hanspers, K., Riutta, A., Windsor, J., Nunes, N., Melius, J., Cirillo, E., Coort, S.L., Digles, D., et al. (2018). WikiPathways: a multifaceted pathway database bridging metabolomics to other omics research. Nucleic Acids Res 46, D661-D667.
Smith, A.S.T., Yoo, H., Yi, H., Ahn, E.H., Lee, J.H., Shao, G., Nagornyak, E., Laflamme, M.A., Murry, C.E., and Kim, D. H. (2017). Micro- and nano-patterned conductive graphene-PEG hybrid scaffolds for cardiac tissue engineering. Chem Commun (Camb) 53, 7412-7415.
Stanley, W.C., Recchia, F.A., and Lopaschuk, G.D. (2005). Myocardial substrate metabolism in the normal and failing heart. Physiol Rev 85, 1093-1129.
Stark, C., Breitkreutz, B.J., Reguly, T., Boucher, L., Breitkreutz, A., and Tyers, M. (2006). BioGRID: a general repository for interaction datasets. Nucleic Acids Res 34, D535-539.
Subramanian, A., Tamayo, P., Mootha, V.K., Mukherjee, S., Ebert, B.L., Gillette, M.A., Paulovich, A., Pomeroy, S.L., Golub, T.R., Lander, E.S., et al. (2005). Gene set enrichment analysis: a knowledge-based approach for interpreting genome-wide expression profiles. Proc Natl Acad Sci U S A 102, 15545-15550.
Sung, T.C., Su, H.C., Ling, Q.D., Kumar, S.S., Chang, Y., Hsu, S.T., and Higuchi, A. (2020). Efficient differentiation of human pluripotent stem cells into cardiomyocytes on cell sorting thermoresponsive surface. Biomaterials 253, 120060.
Tanner, L.B., Goglia, A.G., Wei, M.H., Sehgal, T., Parsons, L.R., Park, J.O., White, E., Toettcher, J.E., and Rabinowitz, J.D. (2018). Four Key Steps Control Glycolytic Flux in Mammalian Cells. Cell systems 7, 49-62 e48.
Thielicke, W., and Eize J. Stamhuis (2014). PIVlab—Towards User-Friendly, Affordable and Accurate Digital Particle Image Velocimetry in MATLAB. Journal of Open Research Software 2.
Thompson, W.R., Nadal-Ginard, B., and Mahdavi, V. (1991). A MyoD1-independent muscle-specific enhancer controls the expression of the beta-myosin heavy chain gene in skeletal and cardiac muscle cells. J Biol Chem 266, 22678-22688.
Tohyama, S., Hattori, F., Sano, M., Hishiki, T., Nagahata, Y., Matsuura, T., Hashimoto, H., Suzuki, T., Yamashita, H., Satoh, Y., et al. (2013). Distinct metabolic flow enables large-scale purification of mouse and human pluripotent stem cell-derived cardiomyocytes. Cell Stem Cell 12, 127-137.
Tu, C., Chao, B.S., and Wu, J.C. (2018). Strategies for Improving the Maturity of Human Induced Pluripotent Stem Cell-Derived Cardiomyocytes. Circ Res 123, 512-514.
Uosaki, H., Cahan, P., Lee, D.I., Wang, S., Miyamoto, M., Fernandez, L., Kass, D.A., and Kwon, C. (2015). Transcriptional Landscape of Cardiomyocyte Maturation. Cell Rep 13, 1705-1716.
Vining, K.H., and Mooney, D.J. (2017). Mechanical forces direct stem cell behaviour in development and regeneration. Nat Rev Mol Cell Biol 18, 728-742.
Wahl, R., Pomper, M., Foster, D.B., et al. (2017). Cardiosphere-Derived Cells Demonstrate Metabolic Flexibility That is Influenced by Adhesion Status. JACC Basic Transl Sci 2, 543-560.
Wakil, S.M., Muiya, N.P., Tahir, A.I., Al-Najai, M., Baz, B., Andres, E., Mazhar, N., Al Tassan, N., Alshahid, M., Meyer, B.F., et al. (2014). A new susceptibility locus for myocardial infarction, hypertension, type 2 diabetes mellitus, and dyslipidemia on chromosome 12q24. Dis Markers 2014, 291419.
Wang, Y.L., and Pelham, R.J., Jr. (1998). Preparation of a flexible, porous polyacrylamide substrate for mechanical studies of cultured cells. Methods Enzymol 298, 489-496.
Weinberger, F., Mannhardt, I., and Eschenhagen, T. (2017). Engineering Cardiac Muscle Tissue: A Maturating Field of Research. Circ Res 120, 1487-1500.
Wixon, J., and Kell, D. (2000). The Kyoto encyclopedia of genes and genomes—KEGG. Yeast 17, 48-55.
Wrighton, P.J., Klim, J.R., Hernandez, B.A., Koonce, C.H., Kamp, T.J., and Kiessling, L.L. (2014). Signals from the surface modulate differentiation of human pluripotent stem cells through glycosaminoglycans and integrins. Proc Natl Acad Sci U S A 111, 18126-18131.
Yan, J., Young, M.E., Cui, L., Lopaschuk, G.D., Liao, R., and Tian, R. (2009). Increased glucose uptake and oxidation in mouse hearts prevent high fatty acid oxidation but cause cardiac dysfunction in diet-induced obesity. Circulation 119, 2818-2828.
Yang, X., Pabon, L., and Murry, C.E. (2014). Engineering adolescence: maturation of human pluripotent stem cell-derived cardiomyocytes. Circ Res 114, 511-523.
Yu, J., Lee, A.R., Lin, W.H., Lin, C.W., Wu, Y.K., and Tsai, W.B. (2014). Electrospun PLGA fibers incorporated with functionalized biomolecules for cardiac tissue engineering. Tissue Eng Part A 20, 1896-1907.
Zhao, X., Cai, A., Peng, Z., Liang, W., Xi, H., Li, P., Chen, G., Yu, J., and Chen, L. (2019). JS-K induces reactive oxygen species-dependent anti-cancer effects by targeting mitochondria respiratory chain complexes in gastric cancer. Journal of cellular and molecular medicine 23, 2489-2504.
Afzal, J., Chan, A., Karakas, M.F., Woldemichael, K., Vakrou, S., Guan, Y., Rathmell, J., Wahl, R., Pomper, M., Foster, D.B., et al. (2017). Cardiosphere-Derived Cells Demonstrate Metabolic Flexibility That Is Influenced by Adhesion Status. JACC Basic Transl Sci 2, 543-560.
Ahmed, R.E., Anzai, T., Chanthra, N., and Uosaki, H. (2020). A Brief Review of Current Maturation Methods for Human Induced Pluripotent Stem Cells-Derived Cardiomyocytes. Front Cell Dev Biol 8, 178.
Akhmedov, M., LeNail, A., Bertoni, F., Kwee, I., Fraenkel, E., and Montemanni, R. (2017). A Fast Prize-Collecting Steiner Forest Algorithm for Functional Analyses in Biological Networks. Lect Notes Comput Sc 10335, 263-276.
Albrecht, S.C., Barata, A.G., Grosshans, J., Teleman, A.A., and Dick, T.P. (2011). In vivo mapping of hydrogen peroxide and oxidized glutathione reveals chemical and regional specificity of redox homeostasis. Cell Metab 14, 819-829.
Aquilano, K., Baldelli, S., and Ciriolo, M.R. (2014). Glutathione: new roles in redox signaling for an old antioxidant. Front Pharmacol 5, 196.

(56) References Cited

OTHER PUBLICATIONS

Aratyn-Schaus, Y., Oakes, P.W., Stricker, J., Winter, S.P., and Gardel, M.L. (2010). Preparation of complaint matrices for quantifying cellular contraction. J Vis Exp, 4;(46):2173.

Archer, C.R., Robinson, E.L., Drawnel, F.M., and Roderick, H.L. (2017). Endothelin-1 promotes hypertrophic remodelling of cardiac myocytes by activating sustained signalling and transcription downstream of endothelin type A receptors. Cell Signal 36, 240-254.

Ayad, N.M.E., Kaushik, S., and Weaver, V.M. (2019). Tissue mechanics, an important regulator of development and disease. Philos Trans R Soc Lond B Biol Sci 374, 20180215.

Barbuti, A., Benzoni, P., Campostrini, G., and Dell'Era, P. (2016). Human derived cardiomyocytes: A decade of knowledge after the discovery of induced pluripotent stem cells. Developmental dynamics : an official publication of the American Association of Anatomists 245, 1145-1158.

Barth, E., Stammler, G., Speiser, B., and Schaper, J. (1992). Ultrastructural quantitation of mitochondria and myofilaments in cardiac muscle from 10 different animal species including man. Journal of molecular and cellular cardiology 24, 669-681.

Bedada, F.B., Wheelwright, M., and Metzger, J.M. (2016). Maturation status of sarcomere structure and function in human iPSC-derived cardiac myocytes. Biochim Biophys Acta 1863, 1829-1838.

Bers, D.M. (2002). Cardiac excitation-contraction coupling. Nature 415, 198-205.

Bienstock, D., Goemans, M.X., Simchilevi, D., and Williamson, D. (1993). A Note on the Prize Collecting Traveling Salesman Problem. Math Program 59, 413-420.

Burgoyne, J.R., Mongue-Din, H., Eaton, P., and Shah, A.M. (2012). Redox signaling in cardiac physiology and pathology. Circ Res 111, 1091-1106.

Burridge, P.W., Matsa, E., Shukla, P., Lin, Z.C., Churko, J.M., Ebert, A.D., Lan, F., Diecke, S., Huber, B., Mordwinkin, N.M., et al. (2014). Chemically defined generation of human cardiomyocytes. Nature methods 11, 855-860.

Carson, D., Hnilova, M., Yang, X., Nemeth, C.L., Tsui, J.H., Smith, A.S., Jiao, A., Regnier, M., Murry, C.E., Tamerler, C., et al. (2016). Nanotopography-Induced Structural Anisotropy and Sarcomere Development in Human Cardiomyocytes Derived from Induced Pluripotent Stem Cells. ACS Appl Mater Interfaces 8, 21923-21932.

Caulfield, J.B., and Janicki, U.S. (1997). Structure and function of myocardial fibrillar collagen. Technol Health Care 5, 95-113.

Chanthra, N., Abe, T., Miyamoto, M., Sekiguchi, K., Kwon, C., Hanazono, Y., and Uosaki, H. (2020). A Novel Fluorescent Reporter System Identifies Laminin-511/521 as Potent Regulators of Cardiomyocyte Maturation. Scientific reports 10, 4249.

Chen, T.W., Wardill, T.J., Sun, Y., Pulver, S.R., Renninger, S.L., Baohan, A., Schreiter, E.R., Kerr, R.A., Orger, M.B., Jayaraman, V., et al. (2013). Ultrasensitive fluorescent proteins for imaging neuronal activity. Nature 499, 295-300.

Cho, G.S., Lee, D.I., Tampakakis, E., Murphy, S., Andersen, P., Uosaki, H., Chelko, S., Chakir, K., Hong, I., Seo, K., et al. (2017). Neonatal Transplantation Confers Maturation of PSC-Derived Cardiomyocytes Conducive to Modeling Cardiomyopathy. Cell Rep 18, 571-582.

Choi, J.S., Smith, A.S.T., Williams, N.P., Matsubara, T., Choi, M., Kim, J.W., Kim, H.J., Choi, S., and Kim, D.H. (2020). Nanopatterned Nafion microelectrode arrays for in vitro cardiac electrophysiology. Adv Funct Mater, 18;30(25):1910660.

Choy, J.Y., Boon, P.L., Bertin, N., and Fullwood, M.J. (2015). A resource of ribosomal RNA-depleted RNA-Seq data from different normal adult and fetal human tissues. Sci Data 2, 150063.

Correia, C., Koshkin, A., Duarte, P., Hu, D., Teixeira, A., Domian, I., Serra, M., and Alves, P.M. (2017). Distinct carbon sources affect structural and functional maturation of cardiomyocytes derived from human pluripotent stem cells. Scientific reports 7, 8590.

Crowder, S.W., Liang, Y., Rath, R., Park, A.M., Maltais, S., Pintauro, P.N., Hofmeister, W., Lim, C.C., Wang, X., and Sung, H.J. (2013). Poly(epsilon-caprolactone)-carbon nanotube composite scaffolds for enhanced cardiac differentiation of human mesenchymal stem cells. Nanomedicine (Lond) 8, 1763-1776.

De las Fuentes, L., Herrero, P., Peterson, L.R., Kelly, D.P., Gropler, R.J., and Davila-Roman, V.G. (2003). Myocardial fatty acid metabolism: independent predictor of left ventricular mass in hypertensive heart disease. Hypertension 41, 83-87.

Dias, T.P., Pinto, S.N., Santos, J.I., Fernandes, T.G., Fernandes, F., Diogo, M.M., Prieto, M., and Cabral, J.M.S. (2018). Biophysical study of human induced Pluripotent Stem Cell-Derived cardiomyocyte structural maturation during long-term culture. Biochem Biophys Res Commun 499, 611-617.

Doenst, T., Nguyen, T.D., and Abel, E.D. (2013). Cardiac metabolism in heart failure: implications beyond ATP production. Circ Res 113, 709-724.

Feaster, T.K., Cadar, A.G., Wang, L., Williams, C.H., Chun, Y.W., Hempel, J.E., Bloodworth, N., Merryman, W.D., Lim, C.C., Wu, J.C., et al. (2015). Matrigel Mattress: A Method for the Generation of Single Contracting Human-Induced Pluripotent Stem Cell-Derived Cardiomyocytes. Circ Res 117, 995-1000.

Feyen, D.A.M., McKeithan, W.L., Bruyneel, A.A.N., Spiering, S., Hormann, L., Ulmer, B., Zhang, H., Briganti, F., Schweizer, M., Hegyi, B., et al. (2020). Metabolic Maturation Media Improve Physiological Function of Human iPSC-Derived Cardiomyocytes. Cell Rep 32, 107925.

Fischer, R.S., Myers, K.A., Gardel, M.L., and Waterman, C.M. (2012). Stiffness-controlled three-dimensional extracellular matrices for high-resolution imaging of cell behavior. Nat Protoc 7, 2056-2066.

Friedman, C.E., Nguyen, Q., Lukowski, S.W., Helfer, A., Chiu, H.S., Miklas, J., Levy, S., Suo, S., Han, J.J., Osteil, P., et al. (2018). Single-Cell Transcriptomic Analysis of Cardiac Differentiation from Human PSCs Reveals HOPX-Dependent Cardiomyocyte Maturation. Cell Stem Cell 23, 586-598 e588.

Gintant, G., Burridge, P., Gepstein, L., Harding, S., Herron, T., Hong, C., Jalife, J., and Wu, J.C. (2019). Use of Human Induced Pluripotent Stem Cell-Derived Cardiomyocytes in Preclinical Cancer Drug Cardiotoxicity Testing: A Scientific Statement From the American Heart Association. Circ Res 125, e75-e92.

Goversen, B., van der Heyden, M.A.G., van Veen, T.A.B., and de Boer, T.P. (2018). The immature electrophysiological phenotype of iPSC-CMs still hampers in vitro drug screening: Special focus on IK1. Pharmacol Ther 183, 127-136.

Guo, Y., and Pu, W.T. (2020). Cardiomyocyte Maturation: New Phase in Development. Circ Res 126, 1086-1106.

Gutscher, M., Pauleau, A.L., Marty, L., Brach, T., Wabnitz, G.H., Samstag, Y., Meyer, A.J., and Dick, T.P. (2008). Real-time imaging of the intracellular glutathione redox potential. Nature methods 5, 553-559.

Harburger, D.S., and Calderwood, D.A. (2009). Integrin signalling at a glance. J Cell Sci 122, 159-163.

Harris, M.A., Clark, J., Ireland, A., Lomax, J., Ashburner, M., Foulger, R., Eilbeck, K., Lewis, S., Marshall, B., Mungall, C., et al. (2004). The Gene Ontology (GO) database and informatics resource. Nucleic Acids Res 32, D258-261.

He, C., Hu, H., Wilson, K.D., Wu, H., Feng, J., Xia, S., Churko, J., Qu, K., Chang, H.Y., and Wu, J.C. (2016). Systematic Characterization of Long Noncoding RNAs Reveals the Contrasting Coordination of Cis- and Trans-Molecular Regulation in Human Fetal and Adult Hearts. Circ Cardiovasc Genet 9, 110-118.

Herron, T.J., Rocha, A.M., Campbell, K.F., Ponce-Balbuena, D., Willis, B.C., Guerrero-Serna, G., Liu, Q., Klos, M., Musa, H., Zarzoso, M., et al. (2016). Extracellular Matrix-Mediated Maturation of Human Pluripotent Stem Cell-Derived Cardiac Monolayer Structure and Electrophysiological Function. Circ Arrhythm Electrophysiol 9, e003638.

Hom, J.R., Quintanilla, R.A., Hoffman, D.L., de Mesy Bentley, K.L., Molkentin, J.D., Sheu, S.S., and Porter, G.A., Jr. (2011). The permeability transition pore controls cardiac mitochondrial maturation and myocyte differentiation. Dev Cell 21, 469-478.

Hu, D., Linders, A., Yamak, A., Correia, C., Kijlstra, J.D., Garakani, A., Xiao, L., Milan, D.J., van der Meer, P., Serra, M., et al. (2018).

(56) References Cited

OTHER PUBLICATIONS

Metabolic Maturation of Human Pluripotent Stem Cell-Derived Cardiomyocytes by Inhibition of HIF1alpha and LDHA. Circ Res 123, 1066-1079.
Hubbi, M.E., Kshitiz, Gilkes, D.M., Rey, S., Wong, C.C., Luo, W., Kim, D.H., Dang, C.V., Levchenko, A., and Semenza, G.L. (2013). A nontranscriptional role for HIF-1alpha as a direct inhibitor of DNA replication. Sci Signal 6, ra10.
Huntley, R.P., Sawford, T., Mutowo-Meullenet, P., Shypitsyna, A., Bonilla, C., Martin, M.J., and O'Donovan, C. (2015). The GOA database: gene Ontology annotation updates for 2015. Nucleic Acids Res 43, D1057-1063.
Ingwall, J.S. (2009). Energy metabolism in heart failure and remodelling. Cardiovasc Res 81, 412-419.
Israeli-Rosenberg, S., Manso, A.M., Okada, H., and Ross, R.S. (2014). Integrins and integrin-associated proteins in the cardiac myocyte. Circ Res 114, 572-586.
Jin, L., Han, Z., Platisa, J., Wooltorton, J.R., Cohen, L.B., and Pieribone, V.A. (2012). Single action potentials and subthreshold electrical events imaged in neurons with a fluorescent protein voltage probe. Neuron 75, 779-785.
Jung, G., Fajardo, G., Ribeiro, A.J., Kooiker, K.B., Coronado, M., Zhao, M., Hu, D.Q., Reddy, S., Kodo, K., Sriram, K., et al. (2016). Time-dependent evolution of functional vs. remodeling signaling in induced pluripotent stem cell-derived cardiomyocytes and induced maturation with biomechanical stimulation. FASEB J 30, 1464-1479.
Jung, J.P., Hu, D., Domian, I.J., and Ogle, B.M. (2015). An integrated statistical model for enhanced murine cardiomyocyte differentiation via optimized engagement of 3D extracellular matrices. Sci Rep 5, 18705.
Kadota, S., Pabon, L., Reinecke, H., and Murry, C.E. (2017). In Vivo Maturation of Human Induced Pluripotent Stem Cell-Derived Cardiomyocytes in Neonatal and Adult Rat Hearts. Stem Cell Reports 8, 278-289.
Kaiser, N.J., Kant, R.J., Minor, A.J., and Coulombe, K.L.K. (2019). Optimizing Blended Collagen-Fibrin Hydrogels for Cardiac Tissue Engineering with Human iPSC-derived Cardiomyocytes. ACS Biomater Sci Eng 5, 887-899.
Kannan, M., Vasan, G., Huang, C., Haziza, S., Li, J.Z., Inan, H., Schnitzer, M.J., and Pieribone, V.A. (2018). Fast, in vivo voltage imaging using a red fluorescent indicator. Nature methods 15, 1108-1116.
Karakikes, I., Ameen, M., Termglinchan, V., and Wu, J.C. (2015). Human induced pluripotent stem cell-derived cardiomyocytes: insights into molecular, cellular, and functional phenotypes. Circ Res 117, 80-88.
Kedaigle A, and E., F. (2018). Discovering altered regulation and signaling through network-based integration of transcriptomic, epigenomic and proteomic tumor data. Methods in Molecular Biology, 1711:13-26.
Keung, W., Boheler, K.R., and Li, R.A. (2014). Developmental cues for the maturation of metabolic, electrophysiological and calcium handling properties of human pluripotent stem cell-derived cardiomyocytes. Stem Cell Res Ther 5, 17.
Khan, M., Xu, Y., Hua, S., Johnson, J., Belevych, A., Janssen, P.M., Gyorke, S., Guan, J., and Angelos, M.G. (2015). Evaluation of Changes in Morphology and Function of Human Induced Pluripotent Stem Cell Derived Cardiomyocytes (HiPSC-CMs) Cultured on an Aligned-Nanofiber Cardiac Patch. PLoS One 10, e0126338.
Kim, D.H., Kshitiz, Smith, R.R., Kim, P., Ahn, E.H., Kim, H.N., Marban, E., Suh, K.Y., and Levchenko, A. (2012). Nanopatterned cardiac cell patches promote stem cell niche formation and myocardial regeneration. Integr Biol (Camb) 4, 1019-1033.
Kim, H.E., Dalal, S.S., Young, E., Legato, M.J., Weisfeldt, M.L., and D'Armiento, J. (2000). Disruption of the myocardial extracellular matrix leads to cardiac dysfunction. J Clin Invest 106, 857-866.
Knoll, S.G., Ali, M.Y., and Saif, M.T. (2014). A novel method for localizing reporter fluorescent beads near the cell culture surface for traction force microscopy. J Vis Exp, 51873.
Kofron, C.M., and Mende, U. (2017). In vitro models of the cardiac microenvironment to study myocyte and non-myocyte crosstalk: bioinspired approaches beyond the polystyrene dish. J Physiol 595, 3891-3905.
Kojer, K., Bien, M., Gangel, H., Morgan, B., Dick, T.P., and Riemer, J. (2012). Glutathione redox potential in the mitochondrial intermembrane space is linked to the cytosol and impacts the Mia40 redox state. EMBO J 31, 3169-3182.
Kolberg, L., Raudvere, U., Kuzmin, I., Vilo, J., and Peterson, H. (2020). gprofiler2—an R package for gene list functional enrichment analysis and namespace conversion toolset g:Profiler. F1000Res 9.
Kolwicz, S.C., Jr., and Tian, R. (2011). Glucose metabolism and cardiac hypertrophy. Cardiovasc Res 90, 194-201.
Kshitiz, Afzal, J., Kim, D.H., and Levchenko, A. (2014). Concise review: Mechanotransduction via p190RhoGAP regulates a switch between cardiomyogenic and endothelial lineages in adult cardiac progenitors. Stem Cells 32, 1999-2007.
Kshitiz, Hubbi, M.E., Ahn, E.H., Downey, J., Afzal, J., Kim, D.H., Rey, S., Chang, C., Kundu, A., Semenza, G.L., et al. (2012). Matrix rigidity controls endothelial differentiation and morphogenesis of cardiac precursors. Sci Signal 5, ra41.
Kumar, N., Sridharan, D., Palaniappan, A., Dougherty, J.A., Czirok, A., Isai, D.G., Mergaye, M., Angelos, M.G., Powell, H.M., and Khan, M. (2020). Scalable Biomimetic Coaxial Aligned Nanofiber Cardiac Patch: A Potential Model for "Clinical Trials in a Dish". Front Bioeng Biotechnol 8, 567842.
Kurokawa, Y.K., and George, S.C. (2016). Tissue engineering the cardiac microenvironment: Multicellular microphysiological systems for drug screening. Adv Drug Deliv Rev 96, 225-233.
Lee, Y.K., Ng, K.M., Chan, Y.C., Lai, W.H., Au, K.W., Ho, C.Y., Wong, L.Y., Lau, C.P., Tse, H.F., and Siu, C.W. (2010). Triiodothyronine promotes cardiac differentiation and maturation of embryonic stem cells via the classical genomic pathway. Mol Endocrinol 24, 1728-1736.
Lewandowski, J., Rozwadowska, N., Kolanowski, T.J., Malcher, A., Zimna, A., Rugowska, A., Fiedorowicz, K., Labedz, W., Kubaszewski, L., Chojnacka, K., et al. (2018). The impact of in vitro cell culture duration on the maturation of human cardiomyocytes derived from induced pluripotent stem cells of myogenic origin. Cell Transplant 27, 1047-1067.
Liu, J., Laksman, Z., and Backx, P.H. (2016). The electrophysiological development of cardiomyocytes. Adv Drug Deliv Rev 96, 253-273.
Liu, J., Lieu, D.K., Siu, C.W., Fu, J.D., Tse, H.F., and Li, R.A. (2009). Facilitated maturation of Ca2+ handling properties of human embryonic stem cell-derived cardiomyocytes by calsequestrin expression. Am J Physiol Cell Physiol 297, C152-159.
Liu, Q., Tian, S., Zhao, C., Chen, X., Lei, I., Wang, Z., and Ma, P.X. (2015). Porous nanofibrous poly(L-lactic acid) scaffolds supporting cardiovascular progenitor cells for cardiac tissue engineering. Acta Biomater 26, 105-114.
Liu, W., Acin-Perez, R., Geghman, K.D., Manfredi, G., Lu, B., and Li, C. (2011). Pink1 regulates the oxidative phosphorylation machinery via mitochondrial fission. Proc Natl Acad Sci U S A 108, 12920-12924.
Liu, Z., Ding, J., McMillen, T.S., Villet, O., Tian, R., and Shao, D. (2020). Enhancing fatty acid oxidation negatively regulates PPARs signaling in the heart. Journal of molecular and cellular cardiology 146, 1-11.
Lopaschuk, G.D., and Jaswal, U.S. (2010). Energy metabolic phenotype of the cardiomyocyte during development, differentiation, and postnatal maturation. J Cardiovasc Pharmacol 56, 130-140.
Lopaschuk, G.D., Ussher, J.R., Folmes, C.D., Jaswal, J.S., and Stanley, W.C. (2010). Myocardial fatty acid metabolism in health and disease. Physiol Rev 90, 207-258.
Lopez-Acosta, O., de Los Angeles Fortis-Barrera, M., Barrios-Maya, M.A., Ramirez, A.R., Aguilar, F.J.A., and El-Hafidi, M. (2018). Reactive Oxygen Species from NADPH Oxidase and Mitochondria Participate in the Proliferation of Aortic Smooth Muscle

(56) References Cited

OTHER PUBLICATIONS

Cells from a Model of Metabolic Syndrome. Oxidative medicine and cellular longevity 2018, 5835072.
Lundy, S.D., Zhu, W.Z., Regnier, M., and Laflamme, M.A. (2013). Structural and functional maturation of cardiomyocytes derived from human pluripotent stem cells. Stem Cells Dev 22, 1991-2002.
Lunt, S.Y., and Vander Heiden, M.G. (2011). Aerobic glycolysis: meeting the metabolic requirements of cell proliferation. Annual review of cell and developmental biology 27, 441-464.
Madamanchi, N.R., and Runge, M.S. (2013). Redox signaling in cardiovascular health and disease. Free Radic Biol Med 61, 473-501.
Mamidi, A., Prawiro, C., Seymour, P.A., de Lichtenberg, K.H., Jackson, A., Serup, P., and Semb, H. (2018). Mechanosignalling via integrins directs fate decisions of pancreatic progenitors. Nature 564, 114-118.
Mammoto, T., and Ingber, D.E. (2010). Mechanical control of tissue and organ development. Development 137, 1407-1420.
Mansson-Broberg, A., Rodin, S., Bulatovic, I., Ibarra, C., Lofling, M., Genead, R., Wardell, E., Felldin, U., Granath, C., Alici, E., et al. (2016). Wnt/beta-Catenin Stimulation and Laminins Support Cardiovascular Cell Progenitor Expansion from Human Fetal Cardiac Mesenchymal Stromal Cells. Stem Cell Reports 6, 607-617.
Marian, A.J., and Braunwald, E. (2017). Hypertrophic Cardiomyopathy: Genetics, Pathogenesis, Clinical Manifestations, Diagnosis, and Therapy. Circ Res 121, 749-770.
McLellan, M.A., Skelly, D.A., Dona, M.S.I., Squiers, G.T., Farrugia, G.E., Gaynor, T.L., Cohen, C.D., Pandey, R., Diep, H., Vinh, A., et al. (2020). High-Resolution Transcriptomic Profiling of the Heart During Chronic Stress Reveals Cellular Drivers of Cardiac Fibrosis and Hypertrophy. Circulation 142, 1448-1463.
Meyer, A.J., and Dick, T.P. (2010). Fluorescent protein-based redox probes. Antioxid Redox Signal 13, 621-650.
Nishiuchi, R., Murayama, O., Fujiwara, H., Gu, J., Kawakami, T., Aimoto, S., Wada, Y., and Sekiguchi, K. (2003). Characterization of the ligand-binding specificities of integrin alpha3beta1 and alpha6beta1 using a panel of purified laminin isoforms containing distinct alpha chains. Journal of biochemistry 134, 497-504.
Nishiuchi, R., Takagi, J., Hayashi, M., Ido, H., Yagi, Y., Sanzen, N., Tsuji, T., Yamada, M., and Sekiguchi, K. (2006). Ligand-binding specificities of laminin-binding integrins: a comprehensive survey of laminin-integrin interactions using recombinant alpha3beta1, alpha6beta1, alpha7beta1 and alpha6beta4 integrins. Matrix Biol 25, 189-197.
Paige, S.L., Plonowska, K., Xu, A., and Wu, S.M. (2015). Molecular regulation of cardiomyocyte differentiation. Circ Res 116, 341-353.
Passier, R., Orlova, V., and Mummery, C. (2016). Complex Tissue and Disease Modeling using hiPSCs. Cell Stem Cell 18, 309-321.
Patra, C., Diehl, F., Ferrazzi, F., van Amerongen, M.J., Novoyatleva, T., Schaefer, L., Muhlfeld, C., Jungblut, B., and Engel, F.B. (2011). Nephronectin regulates atrioventricular canal differentiation via Bmp4-Has2 signaling in zebrafish. Development 138, 4499-4509.
Patra, C., Ricciardi, F., and Engel, F.B. (2012). The functional properties of nephronectin: an adhesion molecule for cardiac tissue engineering. Biomaterials 33, 4327-4335.
Phillips, N.R., Sprouse, M.L., and Roby, R.K. (2014). Simultaneous quantification of mitochondrial DNA copy number and deletion ratio: a multiplex real-time PCR assay. Scientific reports 4, 3887.
Picard, M., Taivassalo, T., Gouspillou, G., and Hepple, R.T. (2011a). Mitochondria: isolation, structure and function. J Physiol 589, 4413-4421.
Picard, M., Taivassalo, T., Ritchie, D., Wright, K.J., Thomas, M.M., Romestaing, C., and Hepple, R.T. (2011b). Mitochondrial structure and function are disrupted by standard isolation methods. PLoS One 6, e18317.
Rao, C., Prodromakis, T., Kolker, L., Chaudhry, U.A., Trantidou, T., Sridhar, A., Weekes, C., Camelliti, P., Harding, S. E., Darzi, A., et al. (2013). The effect of microgrooved culture substrates on calcium cycling of cardiac myocytes derived from human induced pluripotent stem cells. Biomaterials 34, 2399-2411.
Ronaldson-Bouchard, K., Ma, S.P., Yeager, K., Chen, T., Song, L., Sirabella, D., Morikawa, K., Teles, D., Yazawa, M., and Vunjak-Novakovic, G. (2018). Advanced maturation of human cardiac tissue grown from pluripotent stem cells. Nature 556, 239-243.
Rossi, M.A. (1998). Pathologic fibrosis and connective tissue matrix in left ventricular hypertrophy due to chronic arterial hypertension in humans. J Hypertens 16, 1031-1041.
Ruan, J.L., Tulloch, N.L., Razumova, M.V., Saiget, M., Muskheli, V., Pabon, L., Reinecke, H., Regnier, M., and Murry, C.E. (2016). Mechanical Stress Conditioning and Electrical Stimulation Promote Contractility and Force Maturation of Induced Pluripotent Stem Cell-Derived Human Cardiac Tissue. Circulation 134, 1557-1567.
Sa, S., Wong, L., and McCloskey, K.E. (2014). Combinatorial fibronectin and laminin signaling promote highly efficient cardiac differentiation of human embryonic stem cells. Biores Open Access 3, 150-161.
Sabass, B., Gardel, M.L., Waterman, C.M., and Schwarz, U.S. (2008). High resolution traction force microscopy based on experimental and computational advances. Biophys J 94, 207-220.
Kim, et al. (2010) "Nanoscale cure regulate the structure and function of macroscopic cardiac tissue constructs," PNAS, 107(2):562-570.
Kim, et al., (2010) "Supporting Information Kim et al. 10.1073/pnas.0906504107," PNAS, p. 1-11.

* cited by examiner p
Electric pulse stimulation
Nano-grooved traction force gel fabrication
q
r
d30
CMM
Pa
400
700
0 f Flowcytometry to evaluate cTnT during early differentiation and following plating on CMM

*b*. PCA comparison of CMM samples with EHT/3D cardiac tissue a b c k l b

C

Transcriptional factor act
Anisotropic vs Isotropic d e g

DEVICES AND METHODS TO INDUCE ADULT TYPE MATURATION OF HUMAN PLURIPOTENT STEM CELL DERIVED CARDIOMYOCYTES

CROSS REFERENCES

This application claim priority to U.S. Provisional Patent Application Ser. No. 63/321,393, filed Mar. 18, 2022, incorporated by reference here in its entirety.

STATEMENT OF GOVERNMENT SUPPORT

This invention was made with government support under CA248161 awarded by the National Institutes of Health. The government has certain rights in the invention.

SEQUENCE LISTING STATEMENT

A computer readable form of the Sequence Listing is filed with this application by electronic submission and is incorporated into this application by reference in its entirety. The Sequence Listing is contained in the file created on Mar. 6, 2023 having the file name "21-0110-US.xml" and is 13,847 bytes in size.

BACKGROUND

As robust protocols were developed in the last decade to differentiate human induced pluripotent stem cells (hiPSCs) into beating cardiomyocytes (hiPSC-CMs), expectations were set in to create human adult-like cardiac tissue constructs for applications in regenerative medicine, toxicity screens, basic science research, and precision medicine. However, differentiated beating cardiomyocytes exhibit immature phenotypes reminiscent of very early stages of heart development with limited applicability. To date, metabolic maturation, a hallmark of matured cardiac tissue and a fundamental functional necessity, is not yet convincingly demonstrated on engineered heart tissue constructs. Adult cardiomyocytes have a unique physiology, both at the cellular and tissue levels, rendering them highly specialized in generating sufficient and repeated forces for long durations.

SUMMARY DISCLOSURE

In a first aspect, the disclosure provides a construct including a patterned scaffold at submicron resolution. The patterned scaffold includes a polymeric hydrogel substrate including a plurality of wrinkles. The wrinkles include linear or branched folds directionally aligned over a centi-meter length scale. The polymeric substrate has a viscoelasticity between about 15 kPa and about 100 MPa, or about 15 kPa to about 75 MPa. The construct further includes one or more cardiac matrix ligands conjugated to the patterned scaffold. The one or more cardiac matrix ligands comprises 1, 2, 3, 4 or more of Nephronectin, GRGDS (Gly-Arg-Gly-Asp-Ser), GFOGER, GFPGER and/or other peptides containing one or more RGD motifs.

In a second aspect, the disclosure provides a method for making the construct of the first aspect. The method includes creating a patterned substrate comprising a plurality of wrinkles, wherein the plurality of wrinkles comprise linear or branched folds directionally aligned over a centimeter length scale; transferring the patterned substrate to a mold and then transferring the patterned substrate from the mold onto a polymeric hydrogel. The transfer to the polymeric hydrogel creates a patterned scaffold at submicron resolution comprising a plurality of wrinkles.

In a third aspect, the disclosure provides a method for making the construct of the first aspect. The method includes dual exposure patterning (DEP).

In a fourth aspect, the disclosure provides methods for generating cardiomyocytes, including culturing cardiomyocyte precursors on the construct of the first aspect of the disclosure, wherein the culturing is carried out for a time and under suitable conditions to generate differentiated cardiomyocytes.

In a fifth aspect the disclosure provides methods for using the construct of the first aspect of the disclosure.

DETAILED DESCRIPTION

Figure 1:
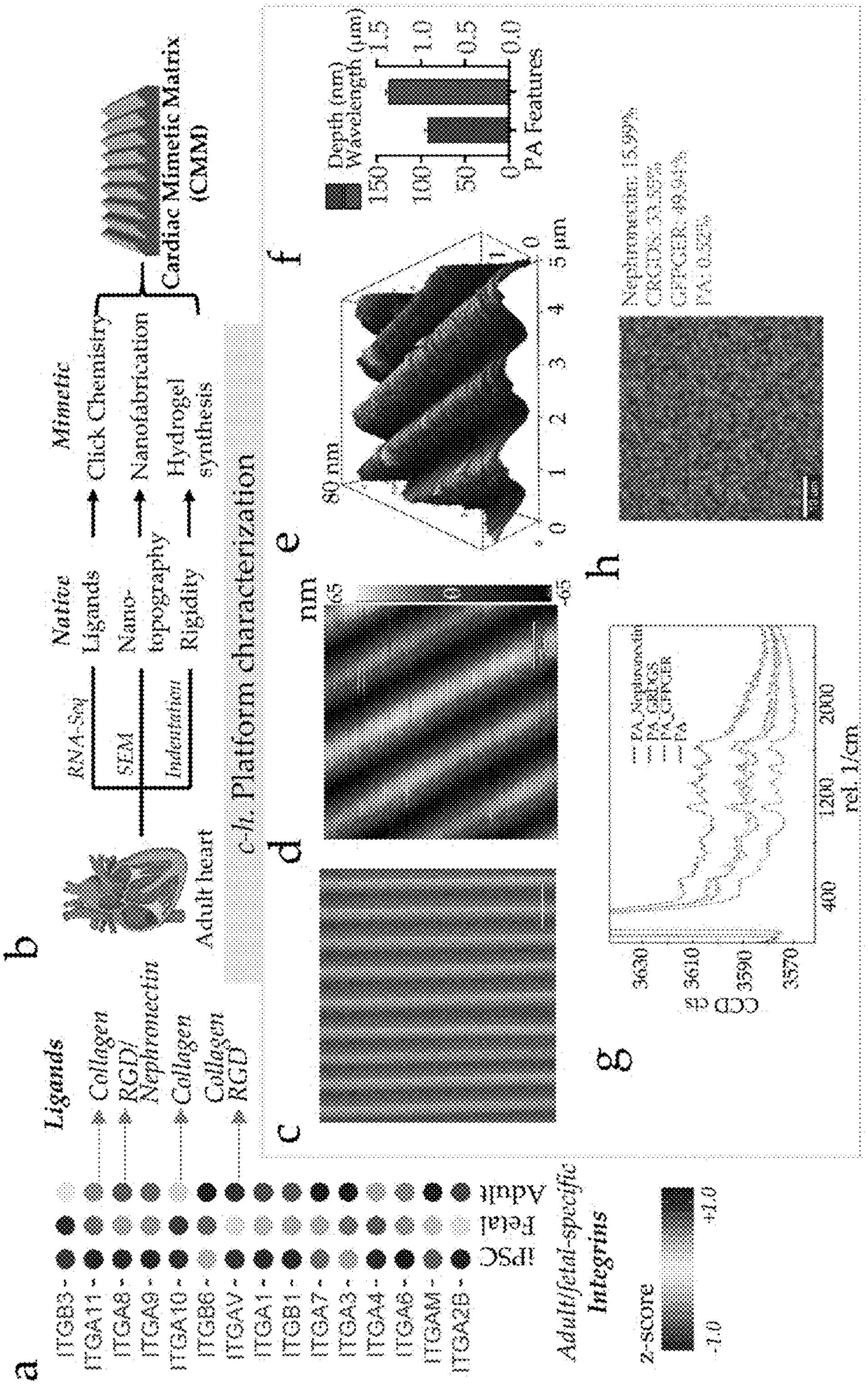
FIG. 1 shows adult heart-like matrix ligands, elasticity and ultrastructure drive a systemic maturation of differentiated human cardiomyocytes. (a) Expression of integrin genes in adult and fetal hearts vs iPSCs. (b) Selected ligands were conjugated to a substrate with anisotropric nanowrinkles (ANW) with Young's modulus of 23 kPa to form Cardiac Mimetic Matrix (CMM). (c) SEM image of polyurethane substrate with ANW, scale bar=2.5 μm; (d) AFM image of CMM, scale bar=1 μm; (e-f) Rendering of CMM topographical features and their quantification; n>6 features. (g) Raman spectroscopy of conjugated peptides on PA hydrogel (h) Raman spectroscopic xy scan showing bound ligands on CMM, scale bar=10 μm. (i) Schematic showing study design. (j-o) RNA Sequencing based analysis; (j) Genes in key functional categories related to cardiac maturation. (k) Unbiased differential gene set analysis between CMM and d30; Cx (complex), AP (action potential), ETC (electron transport chain), MT (mitochondria), SR (sarcoplasmic reticulum) (1-m) CMM accelerates cardiac development and maturation; (1) Maturation path of hiPSC-CMs towards adult heart captured in a linear path within the two largest PCs obtained from transcriptomic states of 30 days of culture (d30 & CMM), d60 and adult heart; line denotes the best fit curve, gray band denotes 95% confidence interval; (m) Adult-like gene expression obtained from cardiac maturation vector. (n) Hierarchical clustering of gene expression; (o) Cluster identity and relative expression of d30, d60 and CMM samples.
Figure 1:
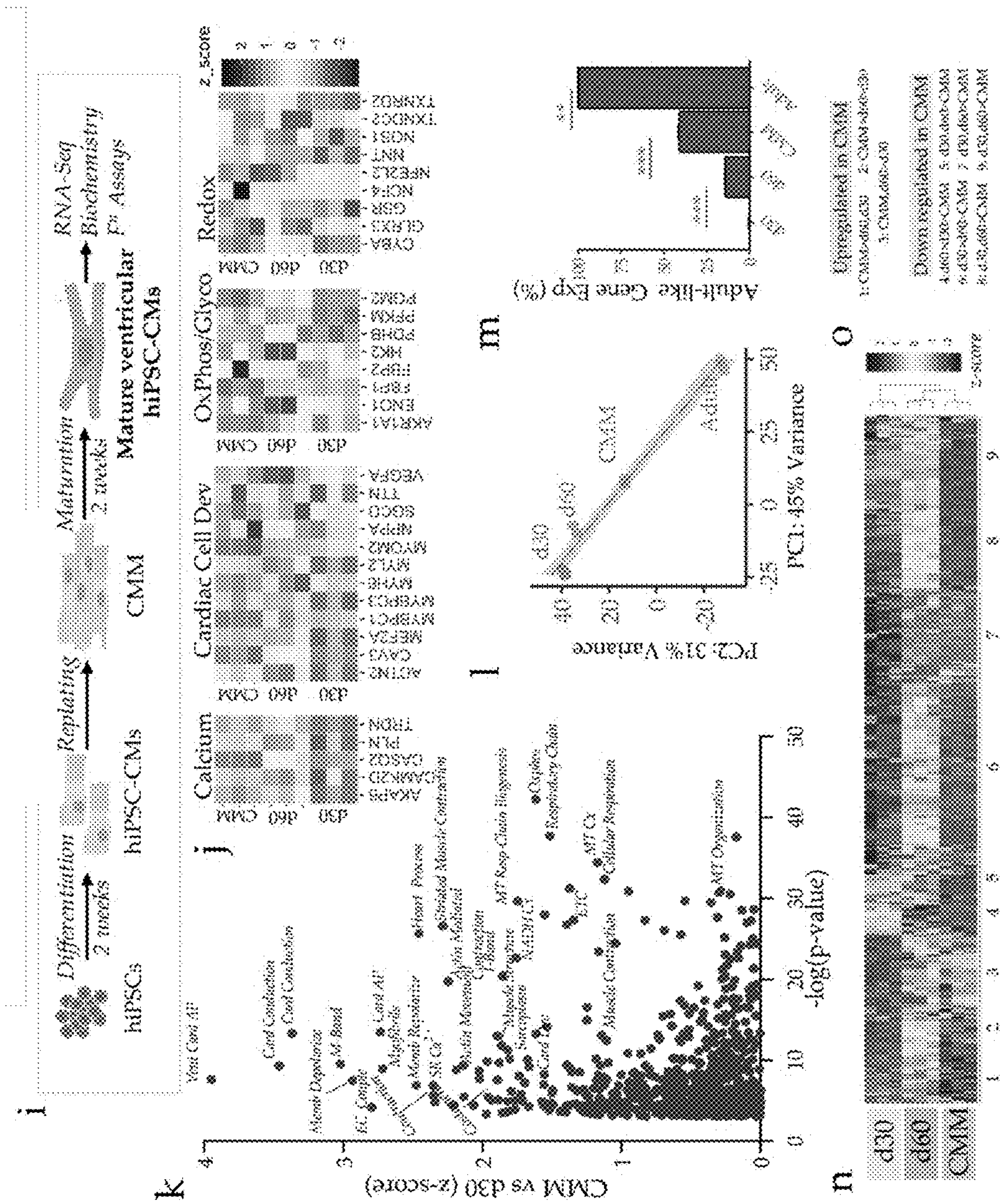

All references cited are herein incorporated by reference in their entirety. Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, CA), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, CA), Culture of Animal Cells: A Manual of Basic Technique, 2nd Ed. (R. I. Freshney. 1987. Liss, Inc. New York, NY), Gene Transfer and Expression Protocols, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the disclosure can be used in combination, unless the context clearly dictates otherwise.

As used herein, the term "about" means+/−5% of the recited value.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

In a first aspect, the disclosure provides a construct, comprising: (a) a patterned scaffold at submicron resolution, wherein the patterned scaffold comprises a polymeric hydrogel substrate comprising a plurality of wrinkles, wherein the wrinkles comprise linear or branched folds directionally aligned over a centi-meter length scale, wherein the polymeric substrate has a rigidity or viscoelasticity between about 15 kPa and about 100 MPa, or about 15 kPa to about 75 MPa; and (b) one or more cardiac matrix ligands conjugated to the patterned scaffold, wherein the one or more cardiac matrix ligands comprises 1, 2, 3, 4 or more of Nephronectin (see SEQ ID NO: 13), GRGDS (Gly-Arg-Gly-Asp-Ser) (SEQ ID NO: 10), GFOGER (SEQ ID NO: 11), GFPGER (SEQ ID NO: 12) and/or other peptides containing one or more RGD motifs.

As disclosed herein, the inventors provide constructs and methods to accelerate maturation of human pluripotent stem cell (induced, or embryonic) derived cardiomyocytes (hiPSC-CMs) by maintaining them on a substrate (referred to herein as Cardiac Mimetic Matrix (CMM)), which combines ligand presentation, anisotropic ultrastructure, and matrix elasticity that are surprisingly shown to synergistically mature hiPSC-CMs, resulting in a systemic adult-like manifestation of gene expression, metabolism, electrophysiological, redox and calcium handling, and force generation in an accelerated time frame. The resultant cardiac tissue is more matured than prolonged cultures, and more closely matches the transcriptomic state of late fetal and adult hearts, in respect to well established and expected structural, mechanical, and metabolic readouts. Specifically, the matured tissue developed using the methods and constructs of the present disclosure has more physiologically a) enhanced oxidative stress handling; b) enhanced calcium handling; c) expression of ion channels resulting in adult-like action potential profile, and responsiveness to to ion channel inhibitor drugs; d) increased expression of cardiac development related transcription factors and genes e) structural maturation with manifestation of fused elongated mitochondria alongside aligned with sarcomeres; f) mitochondrial maturation, and change in energetics with higher mitochondrial electron transport chain (ETC) respiration, increase Adp stimulated respiration, fatty acid oxidation, and metabolic substrate plasticity; and g) increased mechanical contractile, force generation, and increased electromechanical coupling.

In various embodiments, the construct comprises Nephronectin, RGD, and GFOGER (SEQ ID NO: 11) conjugated to the patterned scaffold. In one, non-limiting embodiment, the Nephronectin, RGD, and GFOGER (SEQ ID NO: 11) are present in about an equimolar ratio.

The construct can further comprise laminin, including but not limited to laminin 511/521 and/or laminin 211/221, conjugated to the patterned scaffold. As used herein, "aligned wrinkle ridges", or "aligned wrinkles" refer to raised portion of the polymer scaffold, arranged in highly parallel arrangements with average distance between adjacent ridges between 400 nm to 3 um, which can branch off in space to create new wrinkles while maintaining high degree of parallelness, with angle of branching ranging from 0 to 30 degrees.

In various embodiments, the one or more cardiac matrix ligands comprises proteins comprising the following amino acid sequence:

1. Nephronectin (SEQ ID NO: 13)

```
Mdfllalvlvsslylqaaaefdgrwprqivssiglcryggridccwgwar
qswgqcqpvcqprckhgecigpnkckchpgyagktcnqdlnecglkprpc
khrcmntygsykcyclngymlmpdgscssaltcsmancqygcdvvkgqir
cqcpspglqlapdgrtcvdvdecatgrascprfrqcvntfgsyickchkg
fdlmyiggkyqchdidecslgqyqcssfarcynirgsykckckegyqgdg
ltcvyipkvmiepsgpihvpkgngtilkgdtgnnnwipdvgstwwppktp
yippiitnrptskpttrptpkptpiptpppppplptelrtplppttperp
ttglttiapaastppggitvdnrvqtdpqkprgdvfiprqpsndlfeife
iergvsaddeakddpgvlvhscnfdhglcgwirekdndlhwepirdpagg
qyltvsaakapggkaarlvlplgrlmhsgdlclsfrhkvtglhsgtlqvf
vrkhgahgaalwgrngghgwrqtqitlrgadiksvvfkgekrrghtgeig
lddvslkkghcseer
```

2. RGD (rgd) repeated 1-100 times in sequence

3. GFOGER (Gly-Phe-Hyp-Gly-Glu-Arg) (SEQ ID NO: 11) repeated 1-20 times in sequence.

In various embodiments the polymeric hydrogel substrate comprises aligned wrinkle ridges. The aligned wrinkle ridges can be arranged in one or more (i.e.: 2, 3, 4, 5, 6, 7, 8, 9, 10, or more) continuous and ordered patterns.

The ridges may be of any suitable height between 10 nm to 4 μm; the ridges may all be of approximately the same height over the entire scaffold, of approximately the same height in each discrete section of the scaffold, or may vary between different sections or within a given section. In one embodiment, the height of ridges ranges between about 10 nm and about 2 μm. In one specific embodiment, the ridges are all of approximately the same height over the entire scaffold, or of approximately the same height in each discrete section of the scaffold. Valleys are present between the ridges.

In various, non-limiting embodiments a height of ridges ranges between about 10 nm and about 4 μm, and optionally the ridges are all of approximately the same height over the entire scaffold, or of approximately the same height in each discrete section of the scaffold. In various, non-limiting embodiments the valley to valley distances and/or ridge peak to ridge peak distances of between about 400 nm and about 3 μm. For example, the valley to valley distances and/or ridge peak to ridge peak distances of between about 400 nm and about 500 nm, about 400 nm and about 600 nm, about 400 nm and about 700 nm, about 400 nm and about 800 nm, about 400 nm and about 900 nm, about 400 nm and about 1 μm, about 400 nm and about 1.5 μm, about 400 nm and about 2 μm, or about 400 nm and about 2.5 μm.

As used herein, "valley to valley distance" means the distance between adjacent valleys separated by ridges (i.e.: ridges next to each other).

As used herein, "ridge peak to ridge peak distance" means the distance between immediately adjacent ridges (i.e.: ridges next to each other).

The valley to valley and/or peak to peak distances may all be the same, or may vary from one valley to valley or peak to peak distance to another.

Any suitable polymer may be used that is not toxic to cardiomyocytes, and can be fabricated at high fidelity at submicron scale, and can be fabricated within the rigidity or viscoelasticity range of about 10 kPa-75 MPa as Young's Modulus. In various, non-limiting embodiments the patterned polymeric scaffold comprises a polyacrylamide (PA) or polyethylene glycol (PEG) hydrogel, or poly lactic-co-Glycolic Acid (PLGA), or their chemical branch derivatives. In one embodiment, the patterned polymeric scaffold comprises a polyacrylamide (PA) hydrogel having a rigidity of between about 16-24 kPa. In various, non-limiting embodiments the polymer, such as PA, binds to the one or more cardiac matrix ligands via covalent binding, or polymer, such as PEG, binds to one or more cardiac matrix by functional group conjugation with peptide (e.g. NHS).

In various, non-limiting embodiments the construct comprises embedded fluorescent beads to calculate cellular traction force generation by detecting displacement of beads upon contraction, spontaneous or upon electrical stimulation. Inclusion of embedded fluorescent beads in the construct can be used, for example, to directly calculate cellular traction force, spontaneous or upon electrical stimulation, by detecting displacement of the fluorescent beads. The fluorescent beads may be embedded in the construct using any suitable technique. In one embodiment, the fluorescent beads are embedded in the hydrogel by coating poly-L-lysine (PLL) on plasma treated coverslips followed by bead placement, followed by replica molding of nanowrinkle pattern on polyacrylamide solution over the beads.

The patterned polymeric scaffold can be prepared by shrinking of hydrogel, or stretching of an elastic membrane, preferably polydimethylsiloxane (PDMS), and oxygen plasma administration after stretching to create a mold, which can be then transferred directly to a hydrogel, or via an intermediate oxygen impermeable mold using capillary force lithography, or nanoimprinting. In one non-limiting embodiment, the PDMS membrane has a rigidity of about 580 kPa (created by mixing about 10:1 ratio of base to crosslinker). In another non-limiting embodiment, the membrane may be stretched with the force of about 10.44 N to yield about a 30% strain to create anisotropic nanowrinkles. Shrinking or expansion of expansive hydrogels (e.g. polyacrylate) with prepared nanowrinkles can be utilized to achieve the desired feature sizes ranging from 0.1 μm to 10 μm. The nanowrinkles can be isotropic or non-aligned nanowrinkles and can be created by non-directional stretching, either by stretching in orthogonal directions, or in a circular pattern. Shrinking or expansion of hydrogel can be used to achieve desired feature size, to be used directly, or before transfer to a mold.

The construct can further comprise cardiomyocytes or precursors thereof seeded on the construct. In one non-limiting embodiment, the cardiomyocytes or precursors thereof comprise induced pluripotent stem cell (iPSC, such as human iPSC) derived cardiomyocytes. In a further non-limiting embodiment, the cardiomyocytes or precursors thereof comprise cardiomyocytes. In another non-limiting embodiment, the cardiomyocytes or precursors thereof comprise human cardiomyocytes or precursors thereof. In yet another non-limiting embodiment, the cardiomyocytes or precursors thereof comprise electrochemically connected cardiomyocytes. The cardiomyocytes on the construct may establish and maintain cellular/electrical communications such as gap junctions, such that they can serve as a model of cardiac tissue. In one embodiment, the electrically connected cells are capable of spontaneous synchronized contractions across all or part of the construct, or are capable of being paced in a synchronized fashion by external pacing.

In various, non-limiting embodiments the construct can further comprise cardiac fibroblasts or precursors thereof, endothelial cells, vascular smooth muscle cells and/or macrophages and/or other immune cells seeded on the construct. These embodiments can result in a construct which is similar to the in vivo environment including improved maturation of differentiated human cardiomyocytes, promotion of cell spreading, higher strain energy and contractility, decreased myofibroblast phenotype, maturation in calcium transients and electrophysiological parameters, and increased remodeling.

In a second aspect, the disclosure provides methods for making the construct of any embodiment or combination of embodiments disclosed herein. In one embodiment, the methods includes creating a patterned substrate comprising a plurality of wrinkles, wherein the plurality of wrinkles comprise linear or branched folds directionally aligned over a centimeter length scale; transferring the patterned substrate to a mold and then transferring the patterned substrate from the mold onto a polymeric hydrogel. The transfer to the polymeric hydrogel creates a patterned scaffold at submicron resolution comprising a plurality of wrinkles.

In one embodiment, the method includes two transfer steps; the double transfer involves replica transfer of patterns to a primary mold made of polymer without oxygen permeability, the fabricated pattern is then transferred to the hydrogel. As oxygen interferes with hydrogel polymerization, double transfer allows pattern replication with high fidelity and yield. Anisotropic patterned scaffolds are similar to the aligned bundles of collagen fibers in the human heart. Creating a patterned substrate comprising a plurality of wrinkles can occur using any suitable method, including, but not limited to, nanowrinkling nanoindentation, nanoetching, electron beam lithography, or photolithography, hot embossing, dual exposure patterning, and these methods can also be combined with shrinking or expansion to control feature size. Exemplary techniques are described in the Examples. The wrinkles can be isotropic or non-aligned wrinkles or nanowrinkles and can be created by non-directional stretching, either by stretching in orthogonal directions, or in a circular pattern. Shrinking or expansion of hydrogel can be used to achieve desired feature size. The transferring can occur using any suitable method according to the methods of the invention, including but not limited to capillary force lithography or replica molding. Exemplary techniques are described in the Examples.

Figure 25:
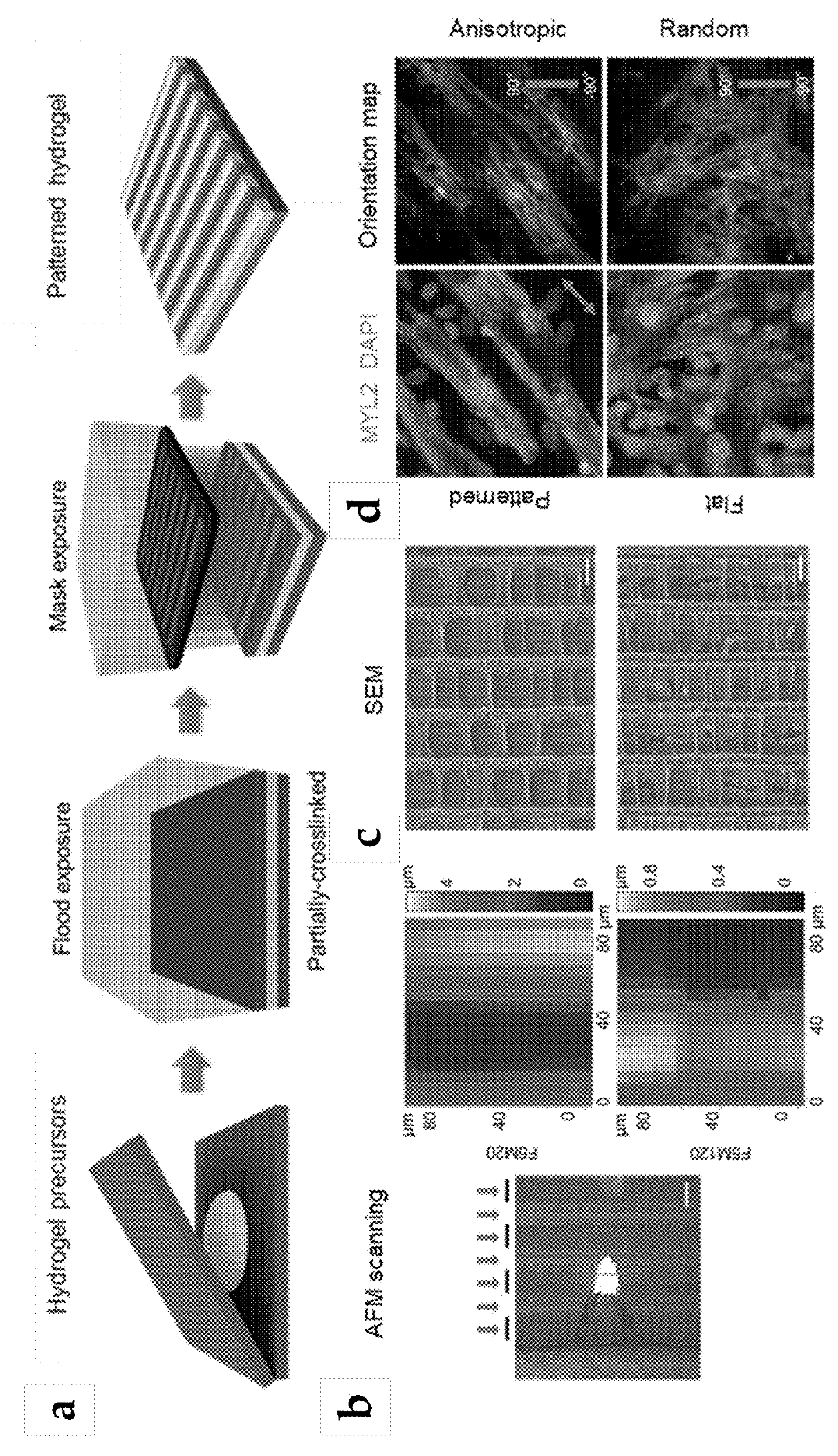
FIG. 25 shows that Dual exposure patterning (DEP) produces hydrogel with sinusoidal topographies. (a) Schematic showing sequential photo-crosslinking of hydrogel creates surfaces topographies using DEP. (b-c) Atomic force microscopy and scanning electron images of surface topographies of DEP fabricated hydrogel using various parameters: F5M20 indicates 5 s of flood exposure followed by 20 s of mask exposure. (d) Fluoresecent images (left column) of cardiomyocytes on patterend hydrogel fabricated using DEP; with flat hydrogel as control. Right column shows the corresponding orientation map.

In a third aspect, the methods for making the construct of any embodiment or combination of embodiments disclosed herein include dual exposure patterning (DEP). DEP can include sequential photo-crosslinking of hydrogel precursors in which (a) primary photo-crosslinking involves a flood light exposure to partially crosslink the precursors; (b) secondary photo-crosslinking involves a masked light exposure to fully crosslink the residual precursors. DEP can be utilized to rapidly achieve centimeter to meter-scale micro/nanopatterned hydrogel. In one embodiment, DEP is used to create anisotropic patterns to culture myocytes in an aligned fashion with directional expression of My12 (FIG. 25).

In various non-limiting embodiments, the patterned substrate comprises polydimethylsiloxane (PDMS) and/or the mold comprises polyurethane (PUA). In various other non-limiting embodiments, the polymeric hydrogel comprises polyacrylamide (PA) or polyethylene glycol (PEG) hydrogel, or poly lactic-co-Glycolic Acid (PLGA), polyurethane (PUA), polyacrylate (PA) or their chemical branch derivatives. In various non-limiting embodiments, the polymeric hydrogel substrate has a viscoelasticity between about 10 kPa and about 100 MPa, or about 15 kPa to about 75 MPa. For example, the polymeric hydrogel substrate has the viscoelasticity between about 15 kPa and about 95 MPa, about 15 kPa and about 90 MPa, about 15 kPa and about 85 MPa, about 15 kPa and about 80 MPa, about 15 kPa to about 70 MPa, about 15 kPa and about 65 MPa, about 15 kPa and about 60 MPa, about 15 kPa and about 55 MPa, about 15 kPa and about 50 MPa, about 15 kPa and about 45 MPa, about 15 kPa and about 40 MPa, about 15 kPa and about 35 MPa, about 15 kPa and about 30 MPa, about 15 kPa and about 25 MPa, about 15 kPa and about 20 MPa, about 15 kPa and about 15 MPa, about 15 kPa and about 10 MPa, or about 15 kPa and about 5 MPa. In various, non-limiting embodiments the patterned polymeric scaffold comprises a polyacrylamide (PA) or polyethylene glycol (PEG) hydrogel, or poly lactic-co-Glycolic Acid (PLGA), or their chemical branch derivatives. In one embodiment, the patterned polymeric scaffold comprises a polyacrylamide (PA) hydrogel having a rigidity of between about 16-24 kPa. For example, the patterned polymeric scaffold comprises the PA hydrogel having the rigidity of about 16 kPa, 17 kPa, 18 kPa, 19 kPa, 20 kPa, 21 kPa, 22 kPa, 23 kPa, or 24 kPa.

As described in the first aspect, the construct can comprises fluorescent beads. According to this embodiment, the fluorescent beads can be embedded in the hydrogel. In one-limiting example of this embodiment, the fluorescent beads can be embedded in the hydrogel by coating poly-L-lysine (PLL) on plasma treated coverslips followed by bead placement, followed by replica molding of nanowrinkle pattern on polyacrylamide solution over the beads.

The methods further comprise conjugating one or more cardiac matrix ligands to the patterned scaffold. In various embodiments, the one or more cardiac matrix ligands comprise 1, 2, 3, 4 or more of Nephronectin (SEQ ID NO: 13), GRGDS (SEQ ID NO: 10), GFOGER (SEQ ID NO: 11), GFPGER (SEQ ID NO: 12), and/or other peptides containing one or more RGD motifs.

The methods can further comprise seeding cardiomyocytes or precursors thereof seeded onto the patterned scaffold. In various, non-limiting embodiments, the cardiomyocytes or progenitors thereof comprise induced pluripotent stem cell (iPSC) derived cardiomyocytes. In one non-limiting embodiment, the cardiomyocytes or progenitors thereof comprise human cardiomyocytes or precursors thereof.

The methods can further comprise seeding cardiac fibroblasts, endothelial cells, vascular smooth muscle cells and/or macrophages and/or other immune cells alone, or in combination, seeded onto the patterned scaffold.

In a fourth aspect, the disclosure provides methods for generating cardiomyocytes, comprising culturing cardiomyocyte precursors on the construct of any embodiment or combination of embodiments disclosed herein, wherein the culturing is carried out for a time and under suitable conditions to generate differentiated cardiomyocytes. In various, non-limiting embodiments, and according to the methods of the disclosure, the cardiomyocytes precursors comprise induced pluripotent stem cell (iPSC, such as human iPSC) from healthy or patients with genetic mutation of interest (e.g. any mutation causing hypertrophic cardiomyopathy, dilated cardiomyopathy, or other cardiovascular diseases). In one non-limiting embodiment, the cardiomyocytes precursors comprise human cardiomyocyte precursors. In various, non-limiting embodiments, and according to the methods of the disclosure, generating cardiomyocytes comprises generating electrically and/or chemically connected cardiomyocytes. According to the methods of the disclosure, the methods may generate cardiomyocytes on the construct that establish and maintain cellular/electrical communications such as gap junctions, such that they can serve as a model of cardiac tissue. In one embodiment, the electrically connected cells are capable of spontaneous synchronized contractions across all or part of the construct. The methods according to the disclosure may generate an electrochemically coupled cardiac layer, expressing key potassium, calcium, or sodium channels in adult ventricular cardiomyocytes, sensitive to caffeine, dependent on fatty acid oxidation, structurally express gap junctions, aligned sarcomeres, fused mitochondria, sensitive to ion channel inhibitors in regulating action potential duration profile, and generating high contractile mechanical force. In various, non-limiting embodiments, and according to the methods of the disclosure, the cardiomyocytes possess one or more of the naturally expressed gene and/or protein characteristics disclosed in the Examples, including but not limited to those listed in Tables 1-4. Specific non-limiting examples include CAMK2D, CASQ2, PLN, TRDN, MYOM2, TTN, MYBPC3, CAV3, PFKM, PDHB, NEFL2, NNT, NOS1, GSR TNNI3, MYOD1, MYPN, MYH2, XIRP2, RYR1, RYR2, ACTN1, DAG1, NBR1, TRIM63, ACTN2, CAV3, GSK3A, MYBPC1/3, GATA4, MEF2C, MYOCD, SRF, KCNJ2, MYL2, MFN1, MFN2, DNM1L, OPA1, LTCC, SERCA, SCNA5, KCNA4, GATA4/5, PPARG, TBX5, MEF2A, MYL7, CICR, and MYOC.

In a fifth aspect the disclosure includes methods for using the construct of any embodiment or combination of embodiments of the disclosure for any suitable purpose, including but not limited to those disclosed in Examples. Examples of suitable methods include, but are not limited to testing the effect of candidate drugs on the construct as a model of the heart (such as human heart, healthy or diseased), studying heart development, and finding therapies for heart diseases (such as human heart disease), or testing toxicity of drugs on human cardiac tissue construct. In one embodiment, the methods may comprise contacting a construct of the disclosure that comprises cardiomyocytes or precursors thereof seeded on the construct with one or more candidate compounds to assess an effect of the one or more candidate compounds on the cardiomyocytes or precursors thereof. In this embodiment, the methods may be used to, for example, identify candidate compounds that elicit a desired effect, or that elicit an undesirable effect, on the cardiomyocytes or precursors thereof. Such methods are useful for identifying candidate compounds to treat heart disorders, as well as identifying candidate compounds that may be toxic to the cardiomyocytes or precursors thereof. Non-limiting effects that can be assessed in these methods include, but are not limited to changes in metabolic readouts, electrophysiological readouts, action potential profile, traction, force generation, calcium and redox handling readouts, optical mapping, transcriptomic and proteomic readouts, and/or mitochondrial function.

In a further non-limiting embodiment, the methods comprises testing candidate drugs for pro-fibrotic and anti-fibrotic effect of candidate drugs on the construct as a model of fibrosis, finding therapies for acquired and/or genetic diseases, and/or using the construct as a model of scarring or fibrotic cardiac tissue at different stages of fibrosis.

The constructs used in the methods may be any embodiment or combination of embodiments of the constructs of the disclosure that are seeded with cardiomyocytes or precursors thereof. In some embodiments, the cardiomyocytes or precursors thereof are human cardiomyocytes or precursors thereof. In other embodiments, the cardiomyocytes or precursors thereof are electrically connected. In other embodiments, the constructs can further comprise cardiac fibroblasts or precursors thereof, endothelial cells, vascular smooth muscle cells and/or macrophages and/or other immune cells seeded on the construct. These embodiments can result in a construct which is similar to the in vivo environment, closely mimicking natural heart collagen matrix architecture, including improved maturation of differentiated human cardiomyocytes, promotion of cell spreading, higher strain energy and contractility, decreased myofibroblast phenotype, maturation in calcium transients and electrophysiological parameters, and increased remodeling. These methods combine the ligand chemistry, elasticity, and anisotropic ultrastructure of the stromal matrix within the heart in a scalable, inexpensive, reproducible, and convenient platform for testing the effects of one or more candidate compounds or drugs on an animal heart model—at the tissue, individual myocytes and on an organelle level.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

EXAMPLES

Example 1: Materials and Methods

Human iPSC culture and cardiac differentiation. Human iPSCs (WTC-11) were cultured using chemically defined medium and published protocols (Burridge et al., 2014; Tohyama et al., 2013). Undifferentiated iPSCs were seeded (125,000 cells per cm$^2$) on Geltrex (ThermoScientific)-coated six-well plates and maintained in E8 medium (Life Technologies) for 4 days when they reached 80-85% confluence. Medium was then changed to cardiac differentiation medium (CDM), consisting of RPMI 1640 medium (11875, ThermoScientific), 500 μg/ml *O. sativa*—derived recombinant human albumin (A9731, Sigma-Aldrich), and 220 μg/ml L-ascorbic acid (A4544-Sigma-Aldrich), containing B27 supplement-insulin free (A1895601 ThermoScientific) to initiate differentiation. On d0-d2, medium was supplemented with 6 μM CHIR99021 (LC Laboratories) for induction of mesoderm. On d4-d5, medium was supplemented with 10 uM IWR (Selleck Chemicals) for cardiac differentiation. Contracting cells are typically noted, starting on d7-d8. To purify cardiac myocytes, a variant of RPMI 1640 medium without D-glucose (11879, Life Technologies) was supplemented with 4 mM sodium lactate (L4263, Sigma-Aldrich) for 2 days on day 10 of differentiation followed by culture in cardiac media, containing B-27™ Supplement with insulin (17504001, ThermoScientific) in CDM medium (Tohyama et al., 2013). Cells were dissociated on d13-d14 using TrypLE (ThermoScientific) and plated/cultured on either flat/anisotropic cell culture surfaces for 15-16 further days (d30 for flat and CMM) or 45 days (d60 for flat culture surface) in cardiac culture media. Cardiac culture media was used in all the conditions from day 13-d14 onwards, and it was composed of RPMI-1640, lipid-enhanced Cellastium S, 220 μg/ml L-ascorbic acid and B27 with insulin. Control flat tissue-culture surfaces were coated with fibronectin at a concentration of 4 μg/cm$^2$. For hypertrophy induction, day 30 differentiated cells were treated with 10 nM endothelin 1 (E7764 Millipore Sigma) for 48 hrs in cardiac culture media. Fabrication of Nanowrinkled Molds for Cardiac Mimetic Matrix.

Polydimethylsiloxane (PDMS) was prepared by mixing the pre-polymer and curing agent in a 10:1 ratio (Dow Corning Sylgard 184), cured at RT or 24 h on a horizontal surface followed by thermal curing of 4 h at 65° C. PDMS slabs (4 (L)×2 (W)×0.3 (H) cm) were then uniaxially stretched to yield 30% strain using a home-made mechanical stretcher and plasma treated with a plasma cleaner (Harrick Plasma PDC32G) with medium RF power for 5 minutes. PDMS nanowrinkles were obtained upon releasing the PDMS slabs from the mechanical stretcher. A library of PDMS nanowrinkles with various periodicity and depth can be achieved by modulating the strain, RF power, and plasma treatment time. The nanowrinkled slab was then transferred to a polyurethane (PU) mold by replica molding. This was achieved by drop dispensing 100 μl PU prepolymer (NOA 76) onto a clean glass slide, and covering the drop with PDMS slab and placing a 3-gram weight on the slab for 5 minutes. Cross-link NOA76 with a UV Cross linker (UV Stratalinker 188; 365 nm) for 20 minutes. Cool the sample at room temperature before peeling off the PDMS mold. SEM images of PDMS and PU molds were obtained using a Hitachi TM1000 tabletop SEM.

Fabrication of Cardiac Mimetic Matrix Substrates. PU molds, bonded to PET sheets for ease of handling, were used as a replica mold to transfer polyacrylamide (PA) topographic patterns. PEG with a similar elasticity was also tested, and no difference between either PEG or PA as measured by calcium response to caffeine, or RT-PCR of a panel of cardiac genes was found. PA precursor was prepared by mixing 10% acrylamide and 0.225% bis-acrylamide solution to yield an expected 23 kPa gel. After degassing for 30 min, 0.05% v/v tetramethylethylenediamine (TEMED) and 0.5% v/v 10% ammonium persulphate (APS) was mixed with precursor solution by gently pipetting. Precursor solution was dispersed onto PU mold, and covered with salinized coverslip for 20 min in a wet chamber. After cross-linking the hydrogel was immersed in 1× PBS for 1 h before peeling off from PU mold. All the samples were stored in 1× PBS solution at 4° C. AFM imaging of the surface topography of the hydrogel was performed using Asylum Research Cypher AFM with a PNP-TR probe in 1× PBS.

Functionalization of CMM and Raman Spectroscopy. Samples were functionalized with 1.3 mg/ml Sulfo-SANPAH under UV for 10 minutes, and incubated in GRGDS (SEQ ID NO: 10) (Peptides International PFA-4189-v), GFPGER (SEQ ID NO: 12) (Sigma-Aldrich 165044K), and nephronectin (SEQ ID NO: 13) (Novus 9560-NP-050) solutions at 4° C. overnight. The samples were washed with 1× PBS for 3 times and stored in PBS at 4° C. before Raman spectroscopy or cell culture. Raman spectroscopy of functionalized hydrogel was performed using WITec alpha300 R Raman microscopy with a 40× immersive objective in 1× PBS using a 785 nm laser. Briefly, five kind of samples were prepared: hydrogel functionalized with (i) no ligands, (ii) GRGDS (SEQ ID NO: 10), (iii) GFPGER (SEQ ID NO: 12), (iv) nephronectin (SEQ ID NO: 13), and (v) GRGDS/GFPGER/nephronectin (SEQ ID NOs: 10, 12, and 13). Individual spectrums of samples (i)-(iv) were obtained with integration time of 1 s and accumulation of 60 times. Distribution of each component in sample (v) was obtained by true component analysis of the large-area Raman scan (50 μm×50 μm, with resolution of 50 pixel×50 pixel) based on the individual spectrums of samples (i)-(iv).

Statistical analysis. Students t-test was performed unless otherwise mentioned with each result. Data is presented as ±SD or ±SEM and mentioned in each results section. Statistical significance is defined as the $p<0.05$ (*) $p<0.01$ () or $p<0.001$ (*).

For gene ontology analyses, statistical significance and z-scores for the enrichment of differentially expressed genes in Gene Ontology gene sets was computed using the following method. First, the individual gene level p-values were transformed to z scores using the inverse of the normal distribution, and the sign assigned by the direction of the fold change. Then, a p-value was evaluated for the gene set by the Student's t-test performed for the genes inside and outside the test. P-values were corrected for multiple testing using false discovery rate (Benjamin-Hochberg) method.

Mitochondrial number. Mitochondrial number was quantified by estimating the amount of mitochondrial DNA (mt-ND1 & mt-ND4) relative to nuclear DNA (B2M) using probe-based Taqman Real Time PCR as described earlier (primer/probes sequence and concentration)(Phillips et al., 2014).

```
mtND1 FP:
                                   (SEQ ID NO: 1)
CTAAATAGCCCACACGTTCCC,

RP:
                                   (SEQ ID NO: 2)
AGAGCTCCCGTGAGTGGTT,

Probe:
                                   (SEQ ID NO: 3)
CATCACGATGGATCACAGGT.

mtND4 FP:
                                   (SEQ ID NO: 4)
CTGTTCCCCAACCTTTTCCT,

RP:
                                   (SEQ ID NO: 5)
CCATGATTGTGAGGGGTAGG,

Probe:
                                   (SEQ ID NO: 6)
GACCCCCTAACAACCCCC.

B2M FP:
                                   (SEQ ID NO: 7)
GCTGGGTAGCTCTAAACAATGTATTCA,

RP:
                                   (SEQ ID NO: 8)
CCATGTACTAACAAATGTCTAAAATGGT,

Probe:
                                   (SEQ ID NO: 9)
CAGCAGCCTATTCTGC.
```

RNA Sequencing and analysis. RNA was isolated using RNeasy Mini Kit™ (Qiagen). Bioanalyzer 2100 (Agilent) was used to check the RNA integrity and samples with RIN <8 were used for library preparation. Library preparation and RNA sequencing were performed by Yale Center for Genome Analysis (YCGA). Reads were aligned to the NCBI GRCh38 genome assembly using the HISAT2 pipeline with default parameters. Reads were counted using HTSeq. Fold changes and statistical significance (p-values) for differential expression were calculated using DESeq2. P-values for differential expression were calculated for the Wald test.

For each functional category the following gene sets were used from the Gene Ontology(Harris et al., 2004), KEGG (Wixon and Kell, 2000), Msigdb(Subramanian et al., 2005), WikiPathways(Slenter et al., 2018), and EBI(Huntley et al., 2015) were used to select the genes to include in the transcriptomic analysis.

TABLE 1

Figure 7:
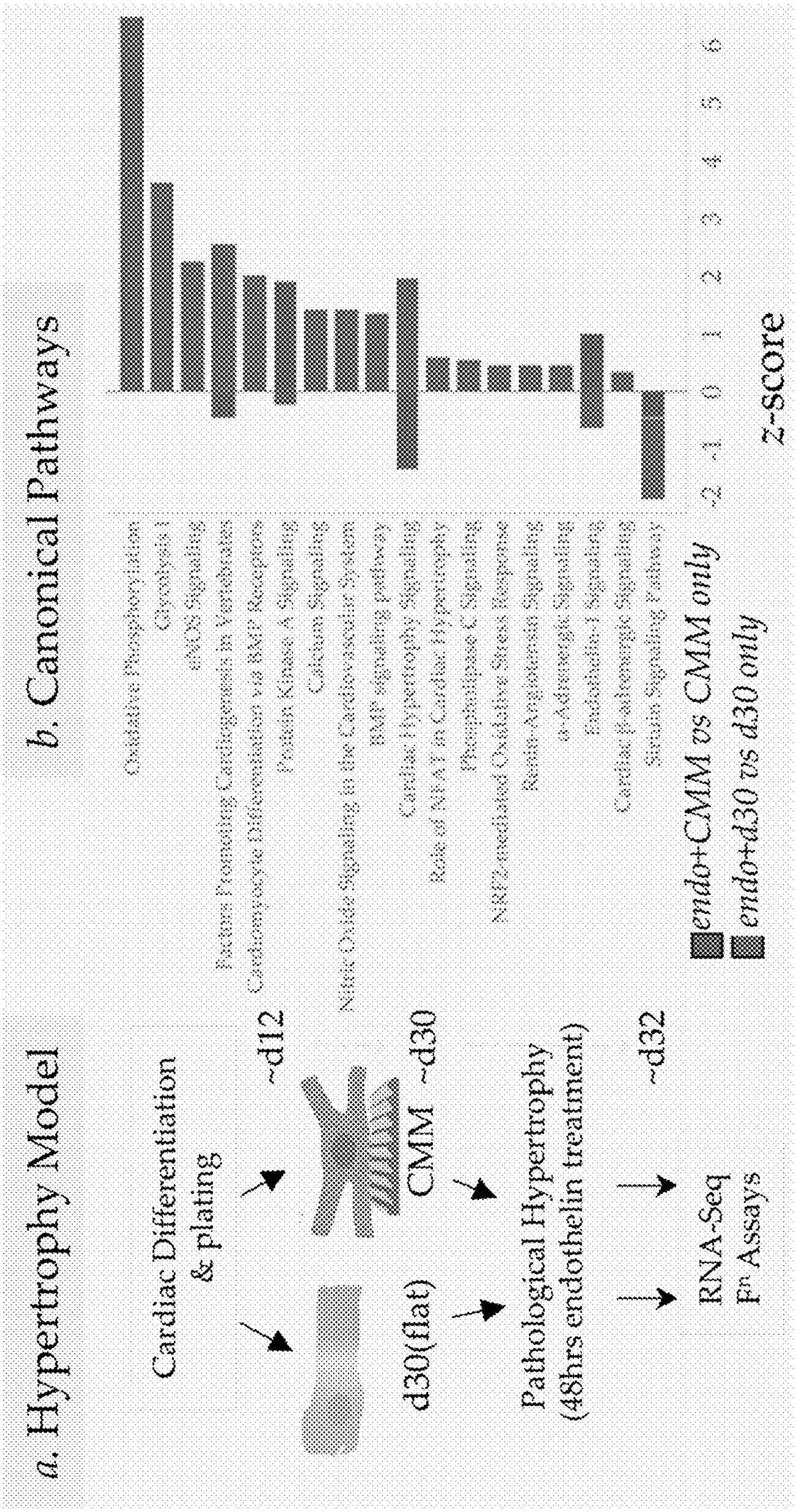
FIG. 7 shows cardiac ultrastructure attenuates pathological hypertrophy phenotype. (a) Schematic showing acute pathological hypertrophy model. (b-c) RNA Sequencing analysis of ET-1 treatment. (b) Canonical pathways (IPA) in ET-1 treated d30 and CMM compared to their respective untreated conditions. (c) Key transcriptional regulators affected by ET-1 treatment in d30 and CMM. (d-1) Functional evaluation of ET-1 effect on d30 and CMM cells. (d) Increase in OxPhos and Glycolysis in d30 cells while cells on CMM exhibits slight increase in glycolysis with no effect on OxPhos. (e) Reduction in FAO with hypertrophy induction on CMM (n=6). (f) Respiratory control ratio (state3/state4) of FAO. (g) Measure of glutathione pool. Systolic (h) and diastolic (i-j) calcium measurements. (k) Beating frequency (beats per minutes). (l) APD measured as time duration between 10% and 90% of peak values.
Figure 7:
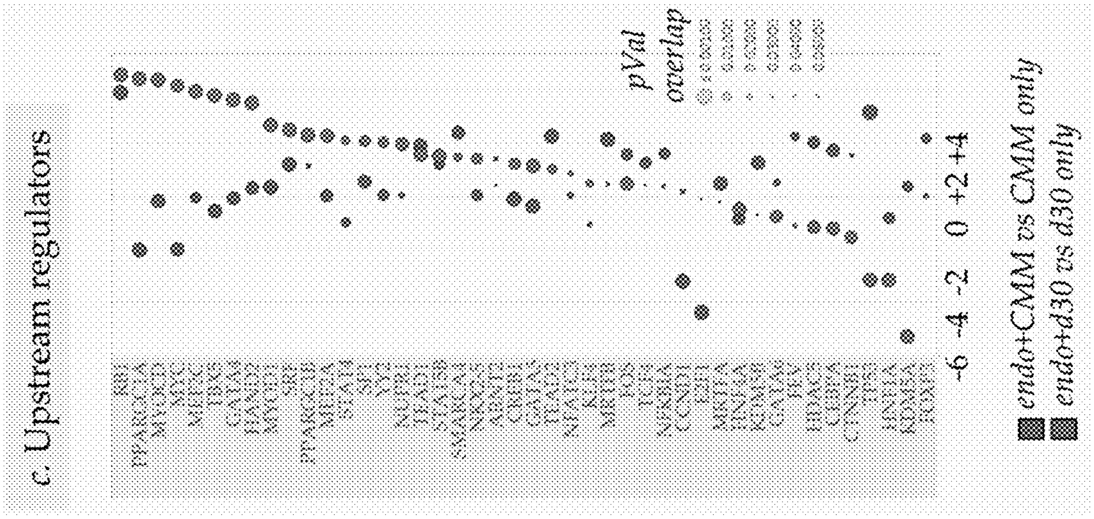
Figure 7:
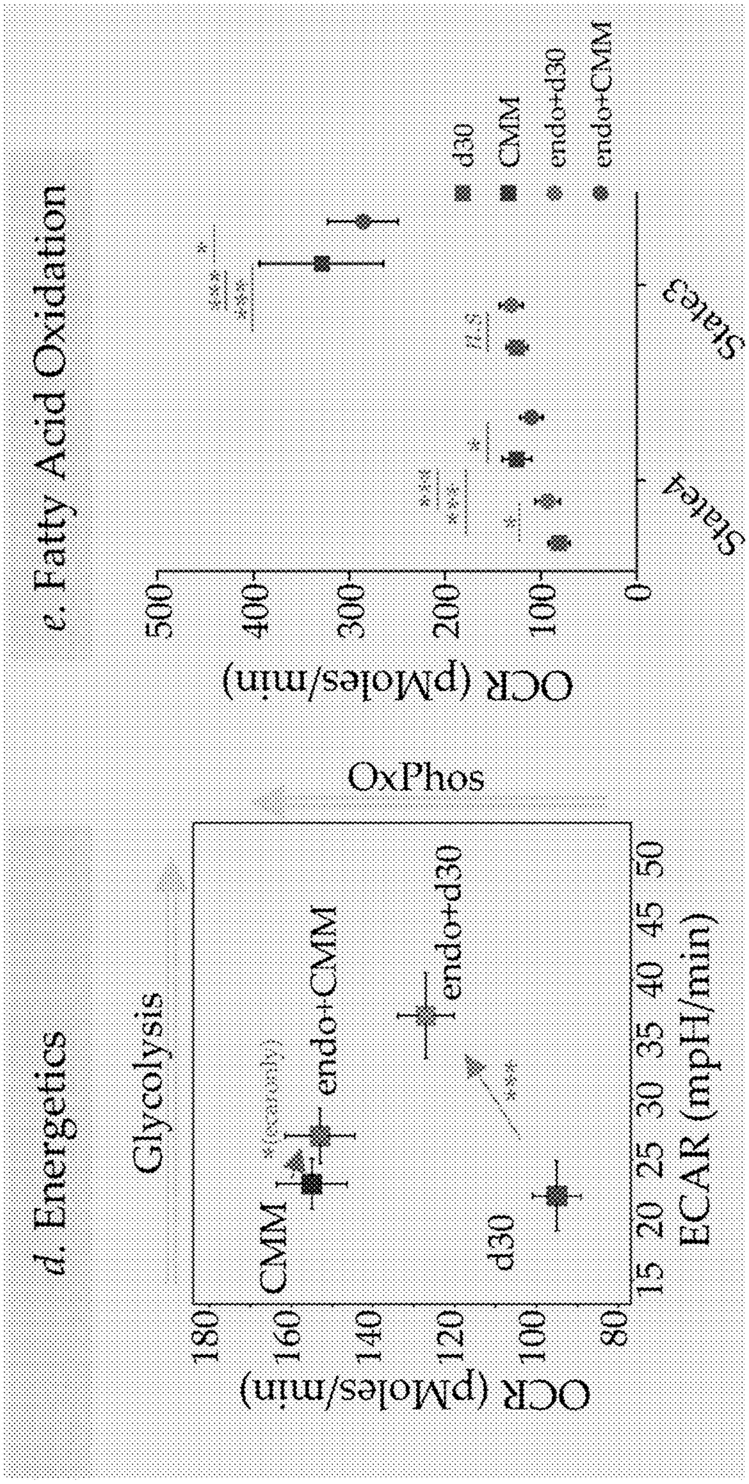
Figure 7:
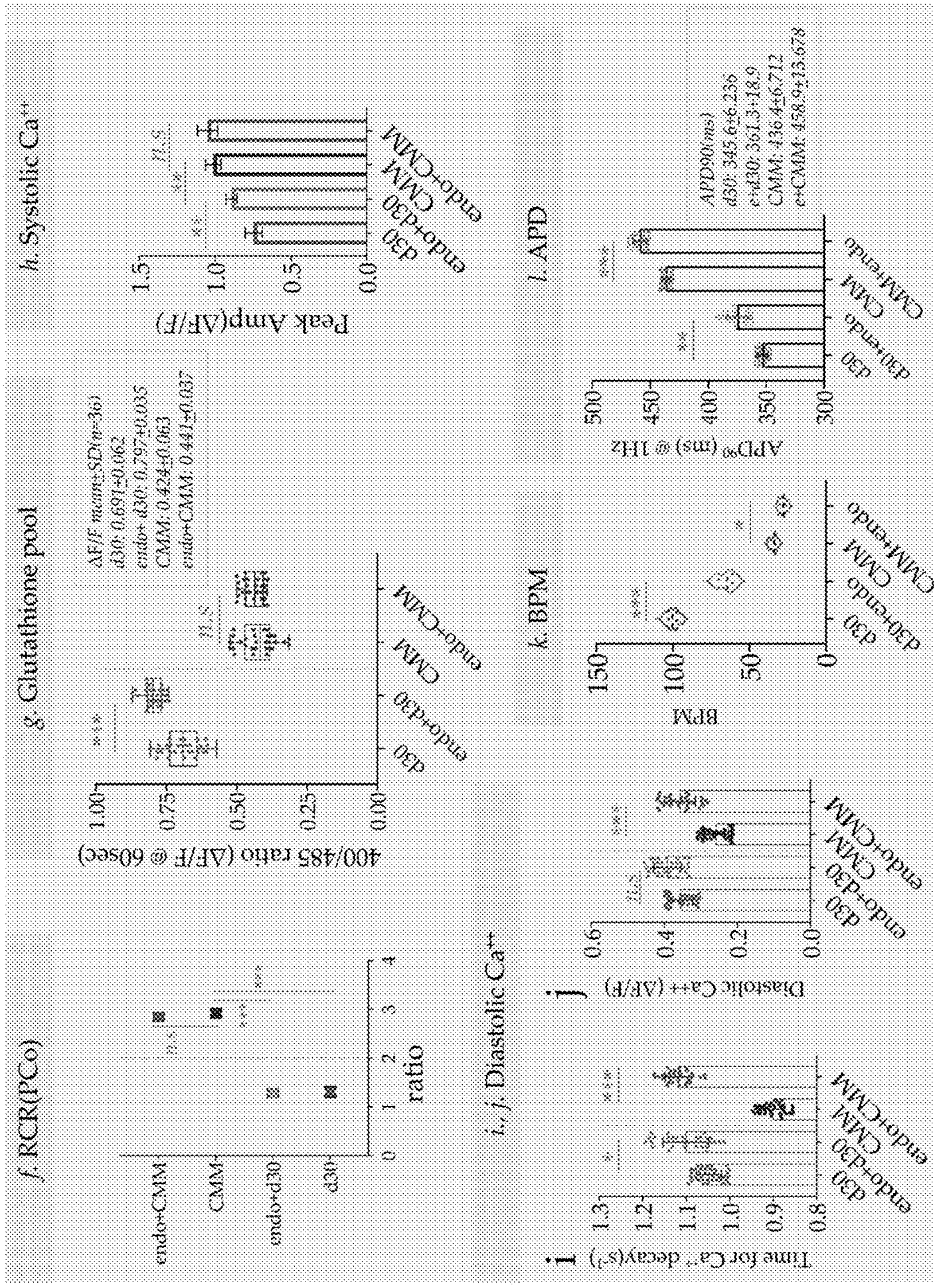

| Functional Category | Gene sets included | Source |
|---|---|---|
| Metabolism (FIG. 5a) | Gluconeogenesis (KEGG) | MSigDB |
| | Cell Redox Homeostasis (GO) | MSigDB |
| | Genes involved in Oxidative Phosphorylation(Pubmed 12808457) | MSigDB |
| | Fatty Acid Catabolic Process (GO) | MSigDB |
| Calcium handling and contractility (FIG. 5b) | Calcium Regulation in the Cardiac cell (www.ncbi.nlm.nih.gov/pubmed/12618512) | WikiPathways |
| | Regulation of Cardiac Muscle Contraction by Calcium Ion Signaling (GO) | MSigDB |
| Voltage and Action (FIG. 5c) | Action Potential (GO) | MSigDB |
| Structure (FIG. 3a, b) | Regulation of Actin Cytoskeleton (KEGG) | MSigDB |
| | Focal Adhesion (KEGG) | MSigDB |
| | ECM Receptor Interaction (KEGG) | MSigDB |
| | Gap Junction (KEGG) | MSigDB |
| Mechanics | Myosin II Complex (GO) | MSigDB |
| | Sarcomere Organization (GO) | MSigDB |
| | Titin Binding (GO) | MSigDB |
| | Actinin Binding (G) | MSigDB |
| Cardiac Cell Development (FIG. 2d-f) | Cardiac Cell Development (GO) | MSigDB |
| Cardiac muscle cell differentiation (FIG. 7) | Cardiac muscle cell differentiation (GO) | EBI |
| Actomyosin Organization (FIG. 7) | Actomyosin Organization (GO) | EBI |
| Mitochondrial Fusion (FIG. 3o) | Mitochondrial Fusion (GO) | EBI |

Hierarchical clustering using UPGMA method with eucledian distance were performed on samples and z-scores of all differentially regulated genes in either conditions, sorted using Anova analysis with FDR correction of 0.05) and 9 main clusters were observed. Ontologies were evaluated in each cluster in GO, Wikipathways, Kegg and Reactome using gprofiler2(Kolberg et al., 2020).

Immunostaining. Cultured cells were washed twice with PBS before fixing them with 4% paraformaldehyde (pH 7.4) for 15 min at room temperature. After fixation, cells were washed with cold PBS before permeabilizing them with PBS buffer containing 0.2% Triton™ X-100 and 0.1% BSA for 15 minutes followed by one-hour incubation with blocking buffer (1% BSA in PBS). Cells were then incubated overnight with primary antibodies with subsequent 30 minutes incubation with secondary antibody. Following primary antibodies were used for labeling; Alexa fluor™ 594 phalloidin (ThermoFisher A12381), Connexin™ 43 (ThermoFisher 35-5000), sarcomeric alpha actinin (ThermoFisher MA1-22863), cardiac troponin T (ThermoFisher MA5-12960), cardiac troponin I (Abcam ab47003), MYL2 (Abcam ab79935), and Wheat Germ Agglutinin, Alexa Fluor™ 488 Conjugate (ThermoFisher W11261). Following Alexa Fluor Secondary Antibodies (ThermoFisher) were used: Alexa Fluor™ 568 (A-11004, A-11011), Alexa Fluor™ 488 (A32723, A32731). Cells were counterstained with DAPI (ThermoFisher D21490) before imaging. The data was analyzed using ImageJ software (version 1.48, National Institutes of Health, Bethesda, MD, USA).

Confocal and Airyscan Imaging. Confocal Images were acquired using a laser scanning confocal microscope, Zeiss LSM 880. Images were taken using a 63× oil objective. Imaging was performed on LSM 880 laser scanning confocal microscope (ZEISS) equipped with 63X Plan Apochromatic 1.40 NA oil objective, an Airyscan super-resolution module, GaAsP detectors and Zen Black acquisition software (ZEISS). The pixel dwell time, laser intensity and detector gain were kept low to avoid saturation and photobleaching during the image acquisition. To increase signal-to-noise ratio and resolution, acquired images were processed by 3D Airyscan filter strength 7.0 with Zen Black software.

Figure 3:
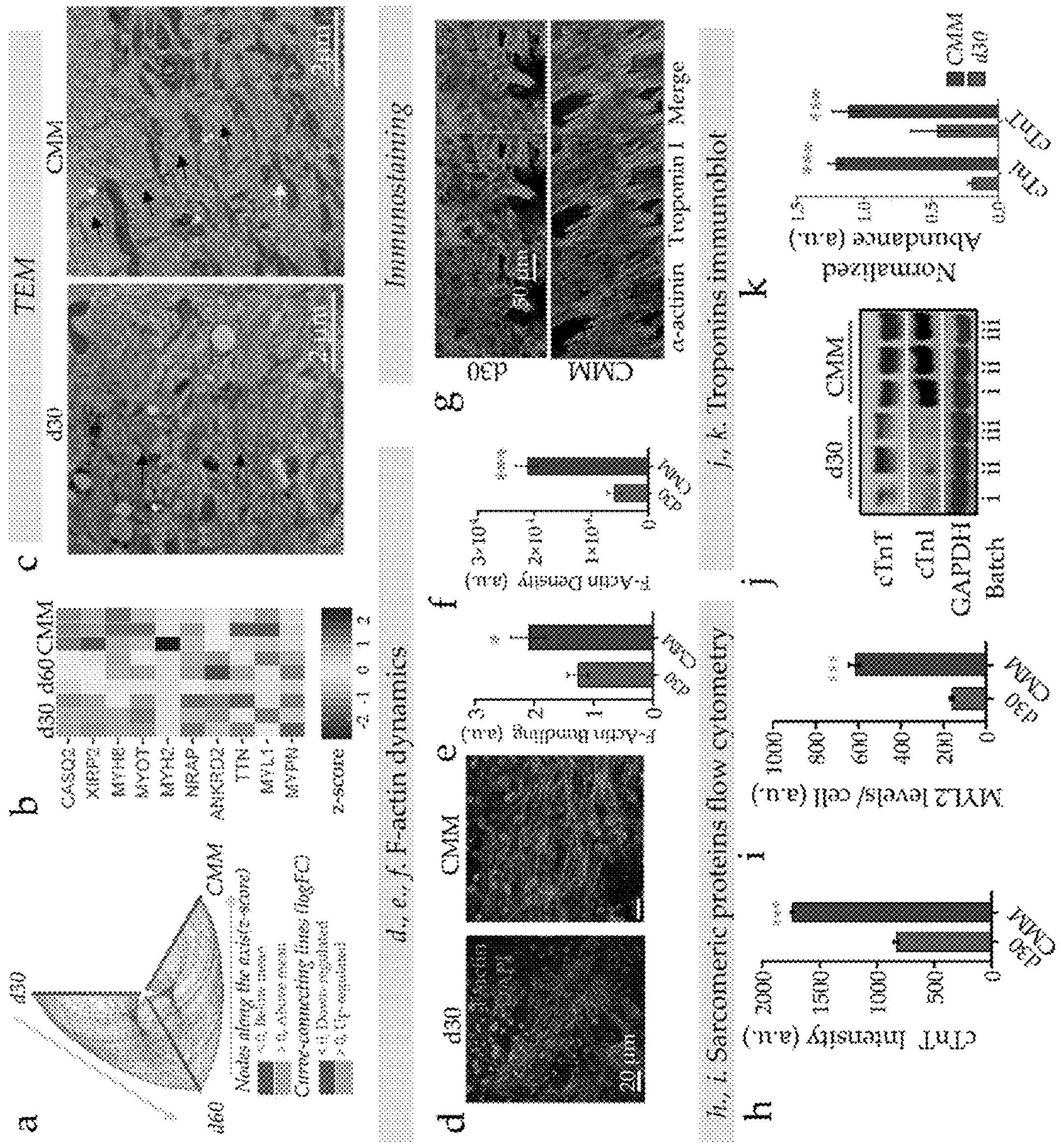
FIG. 3 shows CMM promotes structural maturation of differentiated cardiomyocytes. (a-b) CMM increases expression of genes associated with structural maturation of cardiomyocytes. (a) Hive plot showing relative expression of genes associated with structure related pathways (regulation of actin cytoskeleton, focal adhesion, ECM receptor interaction, and GAP junctions); (b) Top 10 cardiac structure related genes upregulated in CMM vs d30. (c) Ultrastructure analysis using TEM shows aligned sarcomeric structures on CMM compared to d30, black arrows perpendicular to myofibril Z-band, white arrows: mitochondria. Z-Band are oriented in same direction on CMM. (d-f) Aligned and thick F-actin fibers on CMM; n>4 samples. (g) 2-photon images of troponin I and α-actinin show aligned sarcomere on CMM compared to disoriented sarcomere in d30. (h-i) Flow cytometry analysis of sarcomeric proteins. My12 (h) and cTnT (i). (j-m) Higher abundance of cardiac troponins (TnT, TnI) (j-k) and myosin light chain 2 isoforms (1-m) on CMM vs d30. (n) Airyscan image of cells on CMM stained with cardiac troponin T and a-actinin show banding. Sarcomere length (inlet): 1.83±0.1404. Data is represented as ±SD. (o) Overlay of velocity vectors (length: contractile magnitude, angle: direction of contraction) determined by Particle Image Velocimetry on phase-contrasted monolayers of hiPSC-CMs on CMM or control during spontaneous contraction. (p-q) Anisotropic Nanowrinkle (ANW)-incorporated Traction Force Microscopy (TFM). (p) Schematic showing electric pace stimulation of hiPSC-CMs on ANW-TFM substrate. (q) Images showing embedding of fluorescent beads ~3 μm below nanowrinkled pattern. (r) TFM strain energy density maps on d30 and CMM. (s-t) Strain energy and contractility levels of cells on CMM & d30 at 1 Hz paced cells.
Figure 3:
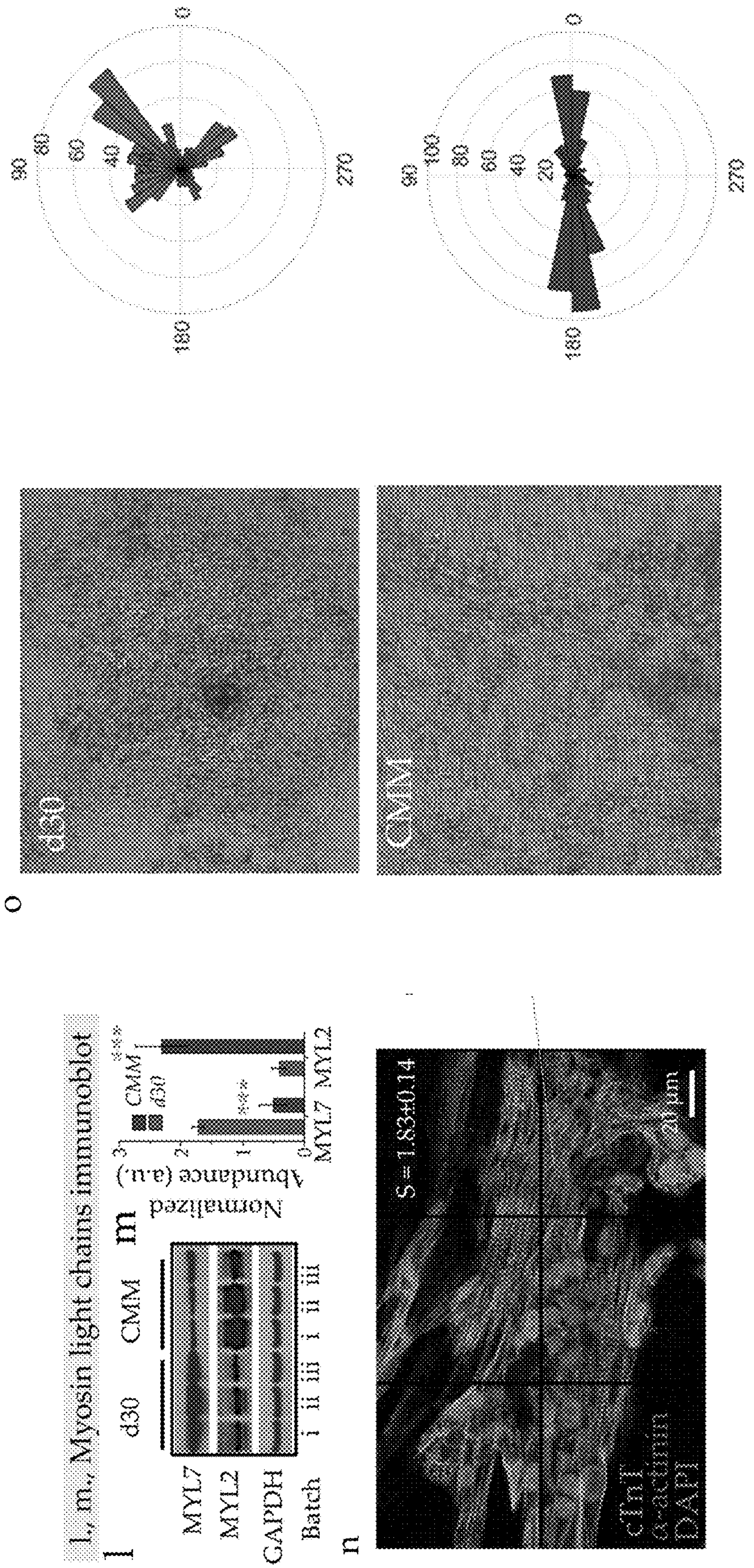
Figure 3:
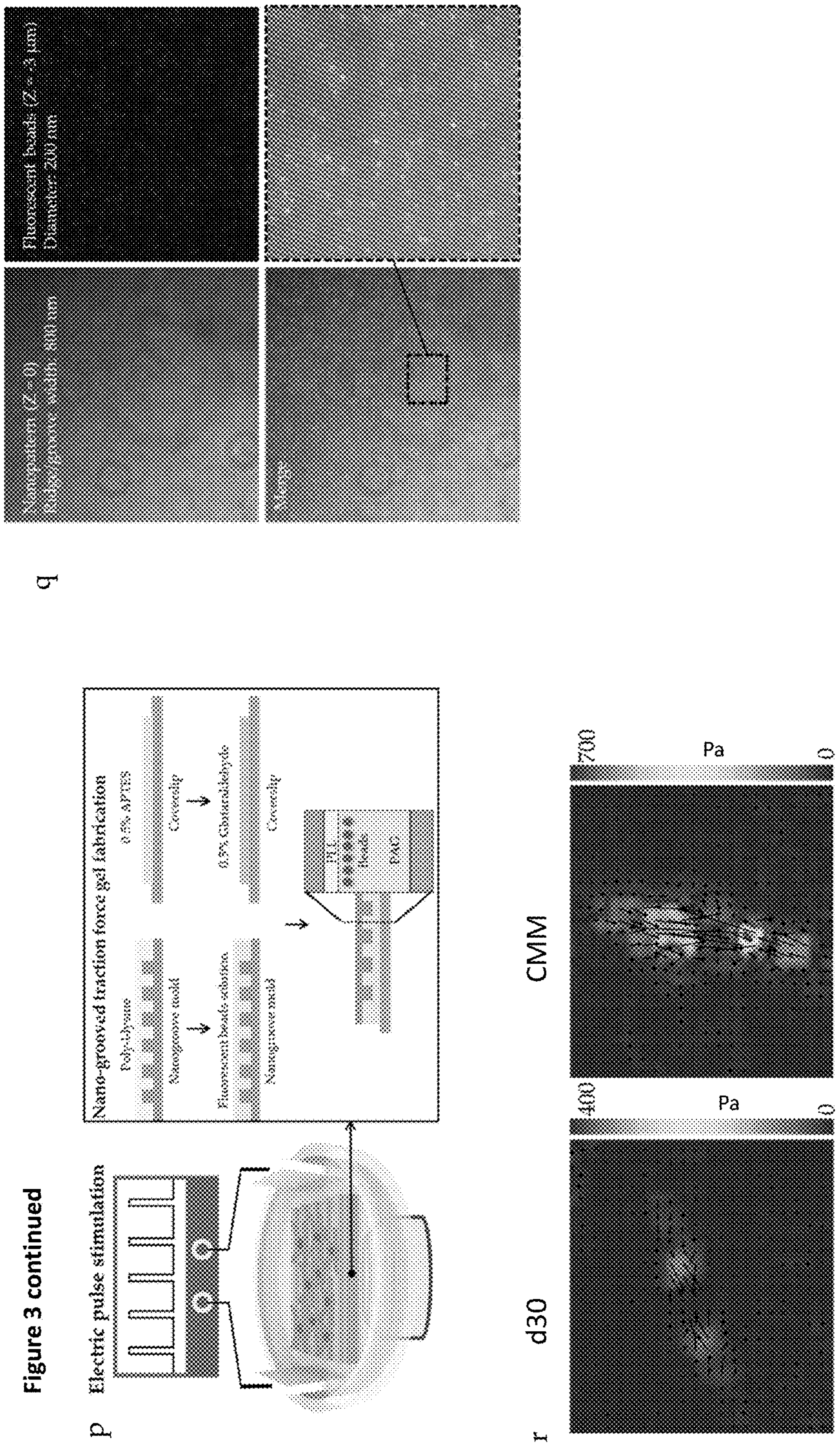
Figure 3:
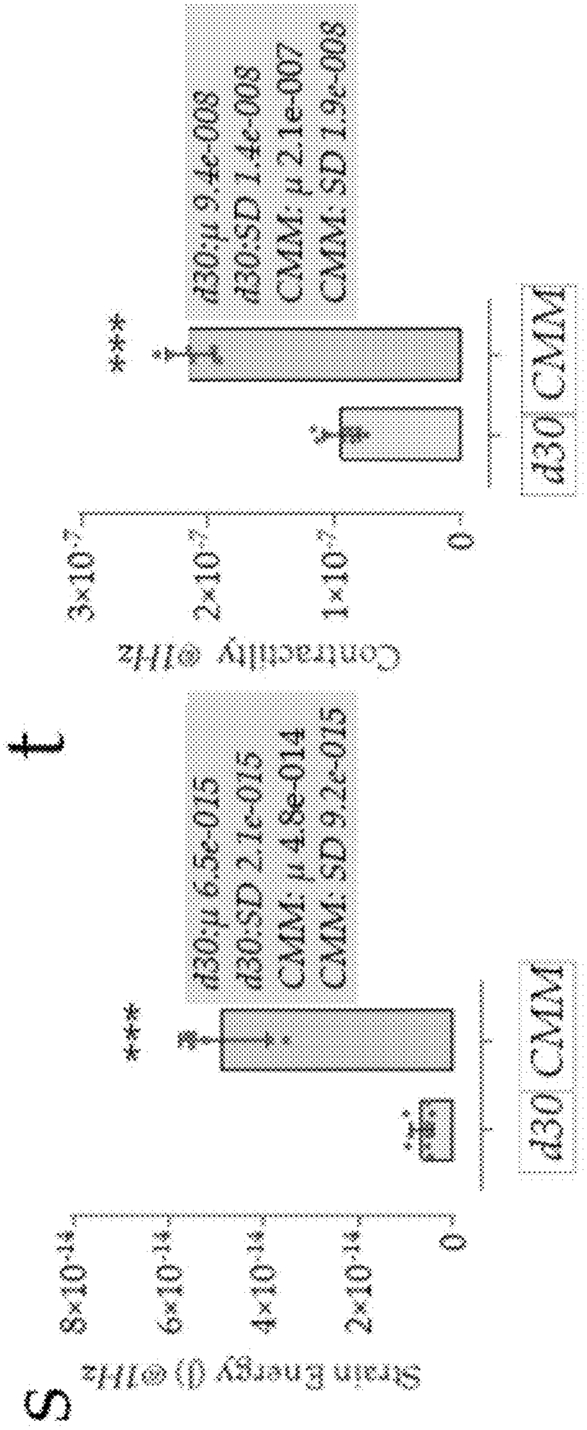
Figure 8:
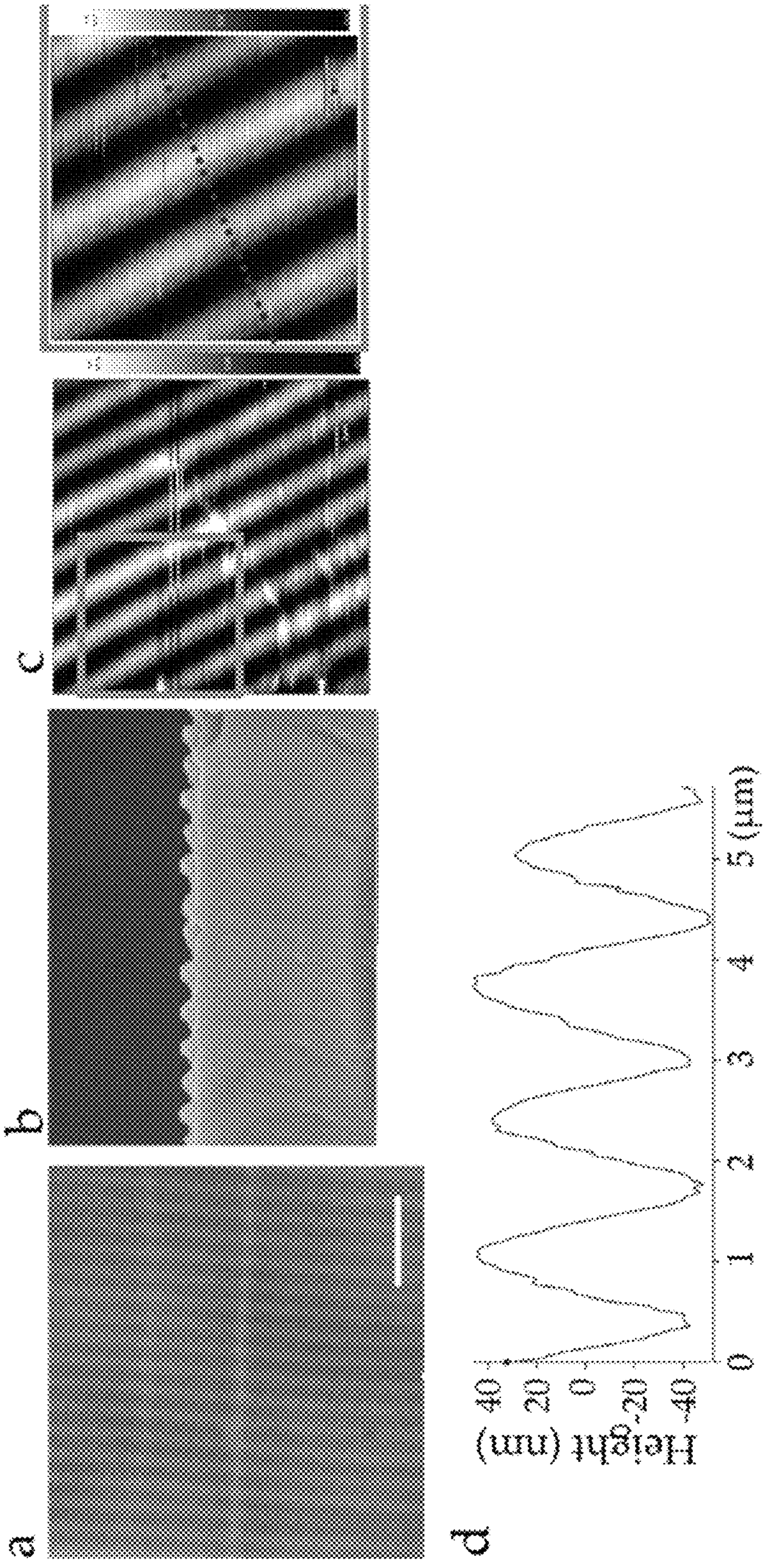
FIG. 8 shows characterization of topographical features in CMM, Related to FIG. 1. (a-b) Phasecontrast image of nanowrinkled PDMS transferred to a polyurethane substrate from top (a), and sideways (b); scale bar=20 μm in a, and 10 μm in b. (c) Atomic force microscopy (AFM) imaging of polyacrylamide based CMM substrate, with zoomed area shown in the right; scale bar=2 μm and 1 μm respectively; height measurements of grooves measured across the dashed line in (d). (e) Flow cytometry data from early differentiated cardiac cells before plating them on flat culture surface or CMM for 2 more weeks. Percent population of Cardiac troponin T cells at d12-14 cells following metabolic selection shows >95% of cardiac cells in three different batches of differentiations that were used in this study. (f) Flow cytometry showing cTnT intensities in a differentiated batch of iPSC-CM at day 14 (~95% of cTnT+ cells), and a batch from same iPSCs differentiated, and then plated on CMM at day 30 (>99% cTnT cells). Negative control was used to exclude nonspecific antibody binding.
Figure 8:
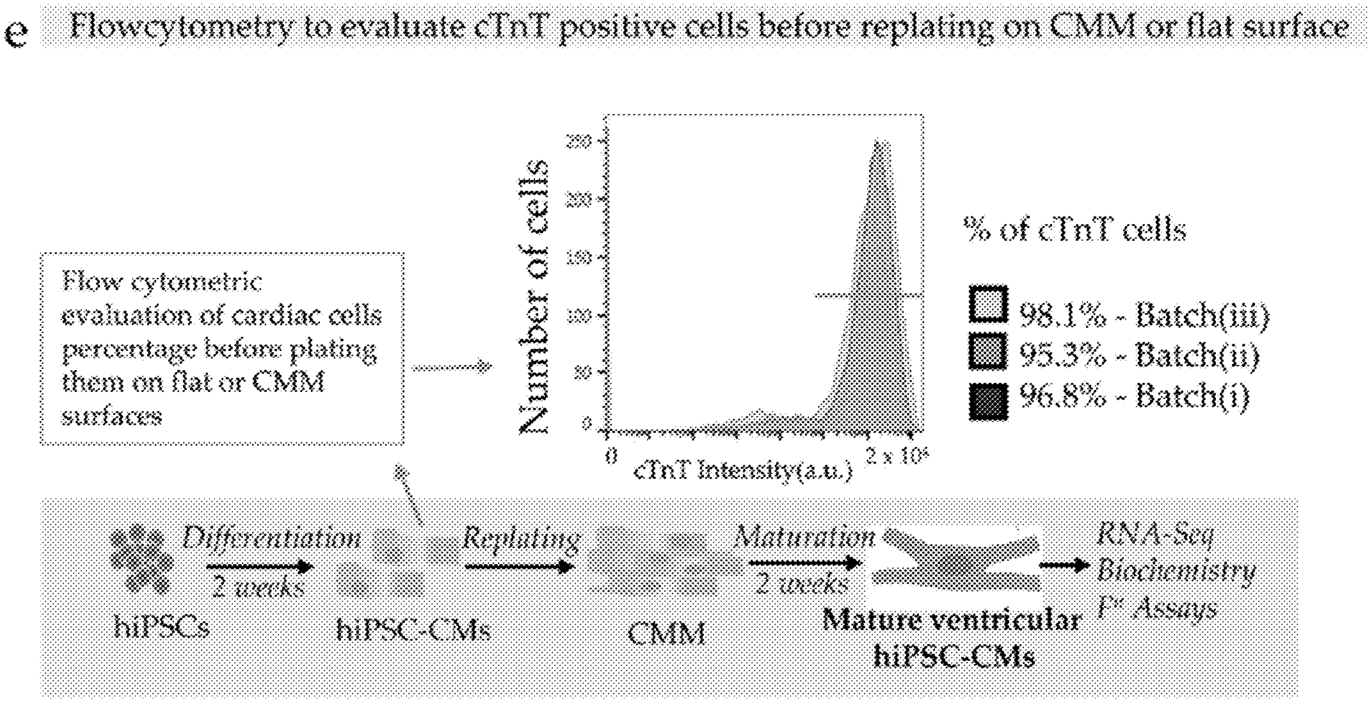
Figure 8:
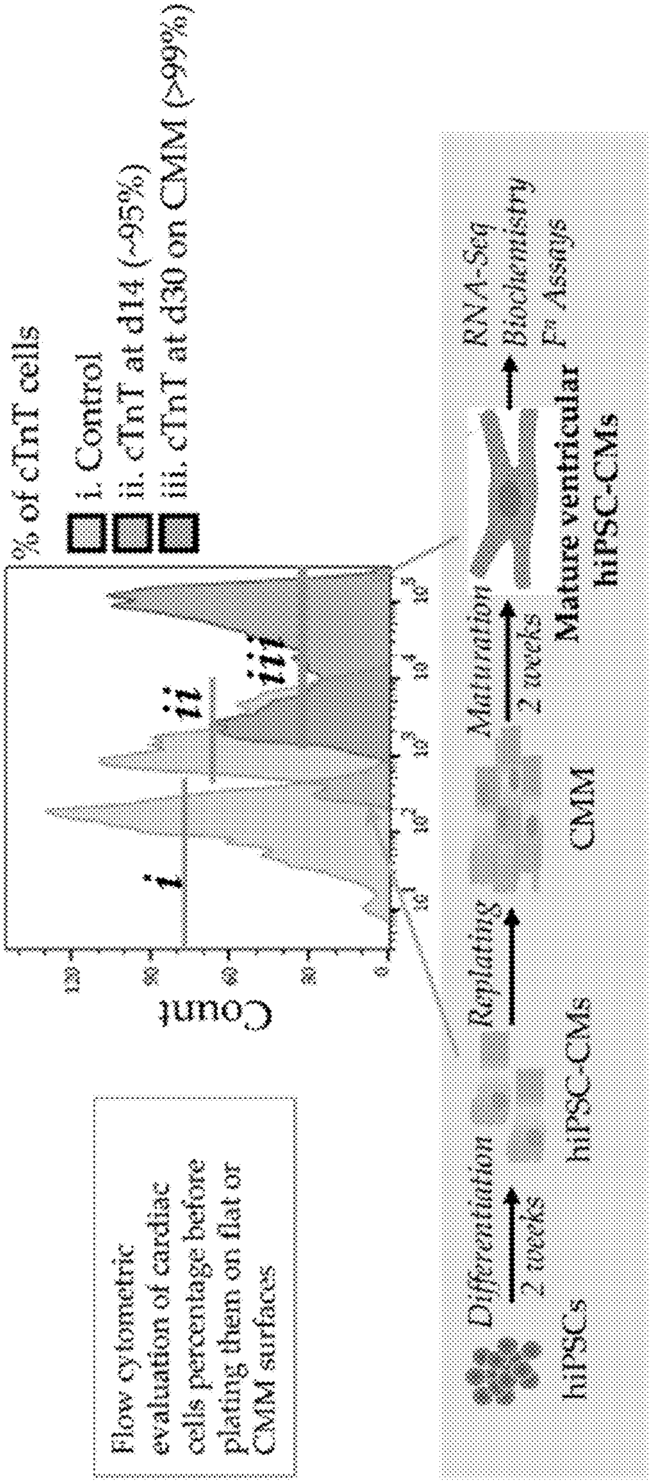

Imaging in FIGS. 3*h* and 8 is with pixel size 0.041×0.041 μm, image size of 202×202 μm and 9 Tiles.

Imaging in FIG. 3*i* is with pixel size 0.070 λ0.070 μm, image size of 133×133 μm and 4 Tiles.

Figure 4:
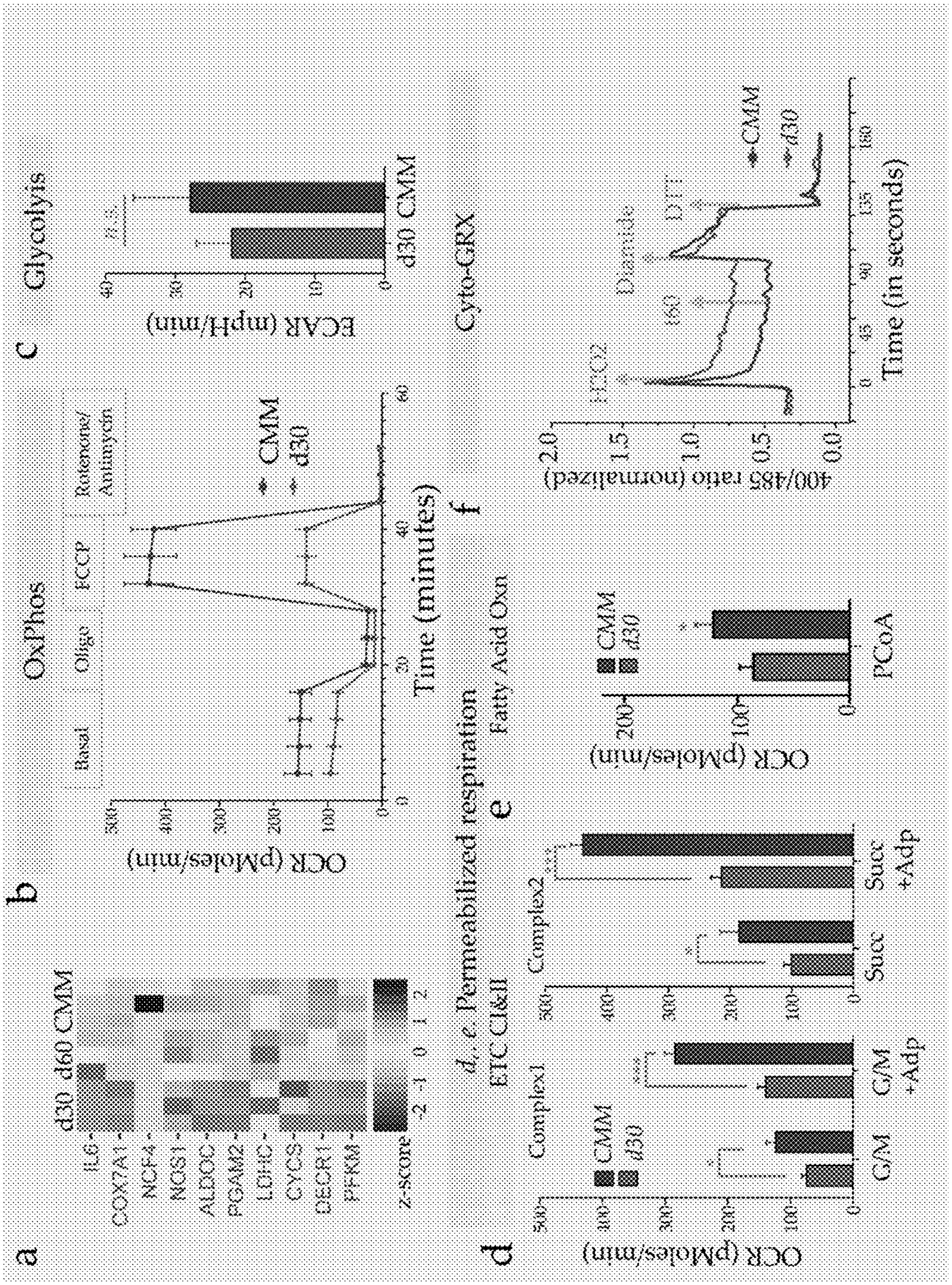
FIG. 4 shows metabolic maturation of cardiomyocytes is accelerated by CMM. (a) Heat map of top 10 genes upregulated in CMM vs d30. (b-e) CMM increases respiration of hiPSC-CMs. In intact cells, (b) hiPSC-CMs cultured on CMM showed increase in basal, coupled (oligomycin sensitive), and uncoupled (FCCP sensitive) respiration, but not in glycolysis (c). (d-e) Permeabilized respiration, (d) state4 and state3 respiration on CMM vs d30. (e) oxidation of long chain fatty acid (200 μM Palmitoyl CoA) on CMM vs d30 (f-g) CMM increases oxidative stress handling capacity in differentiated cardiomyocytes; (f) Representative roGFP2-Grx signal in hiPSC-CMs maintained on CMM or control substrate pulsed with 100 μM $H_2O_2$, washed out after perfusion, and glutathione pool monitored for 60 seconds before adding Diamide and DTT to obtain max & min signal respectively; (g) Quantitative measure showing >80% recovery of glutathione pool on CMM compared to 50% recovery on d30 control; n=30 in each experimental replicate. (h-i) Immunoblot of key metabolic enzymes.
Figure 4:
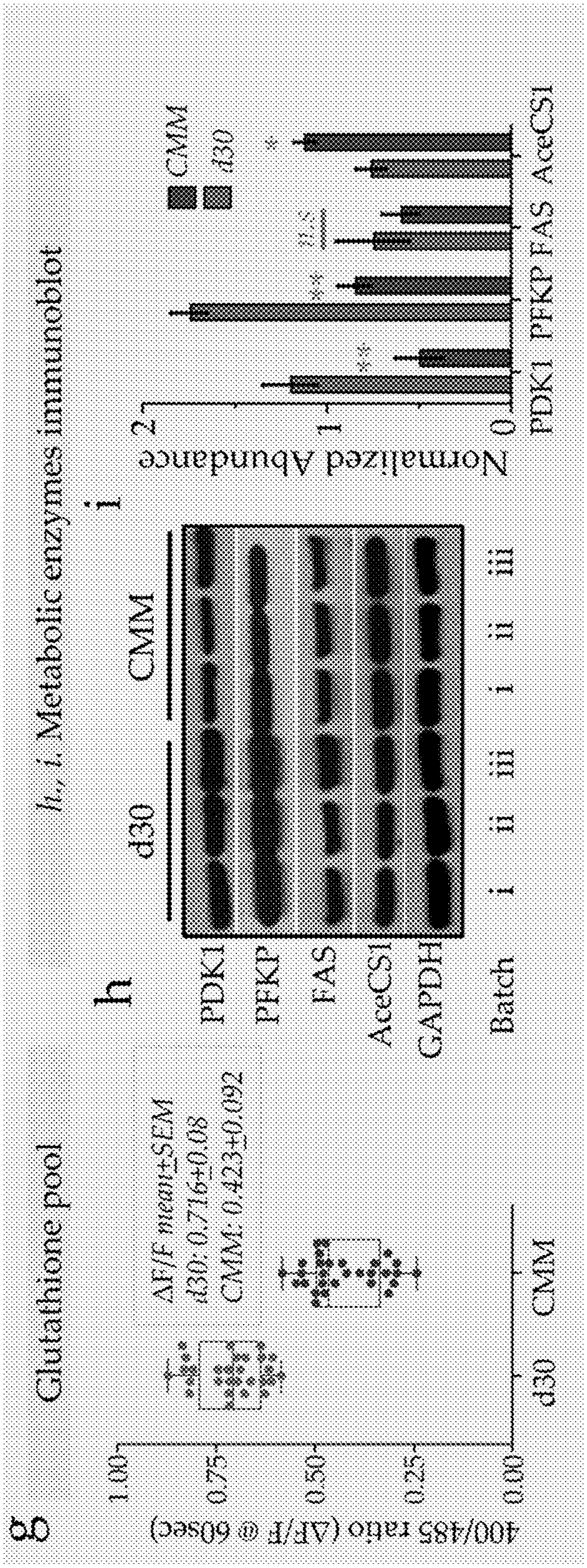
Figure 9:
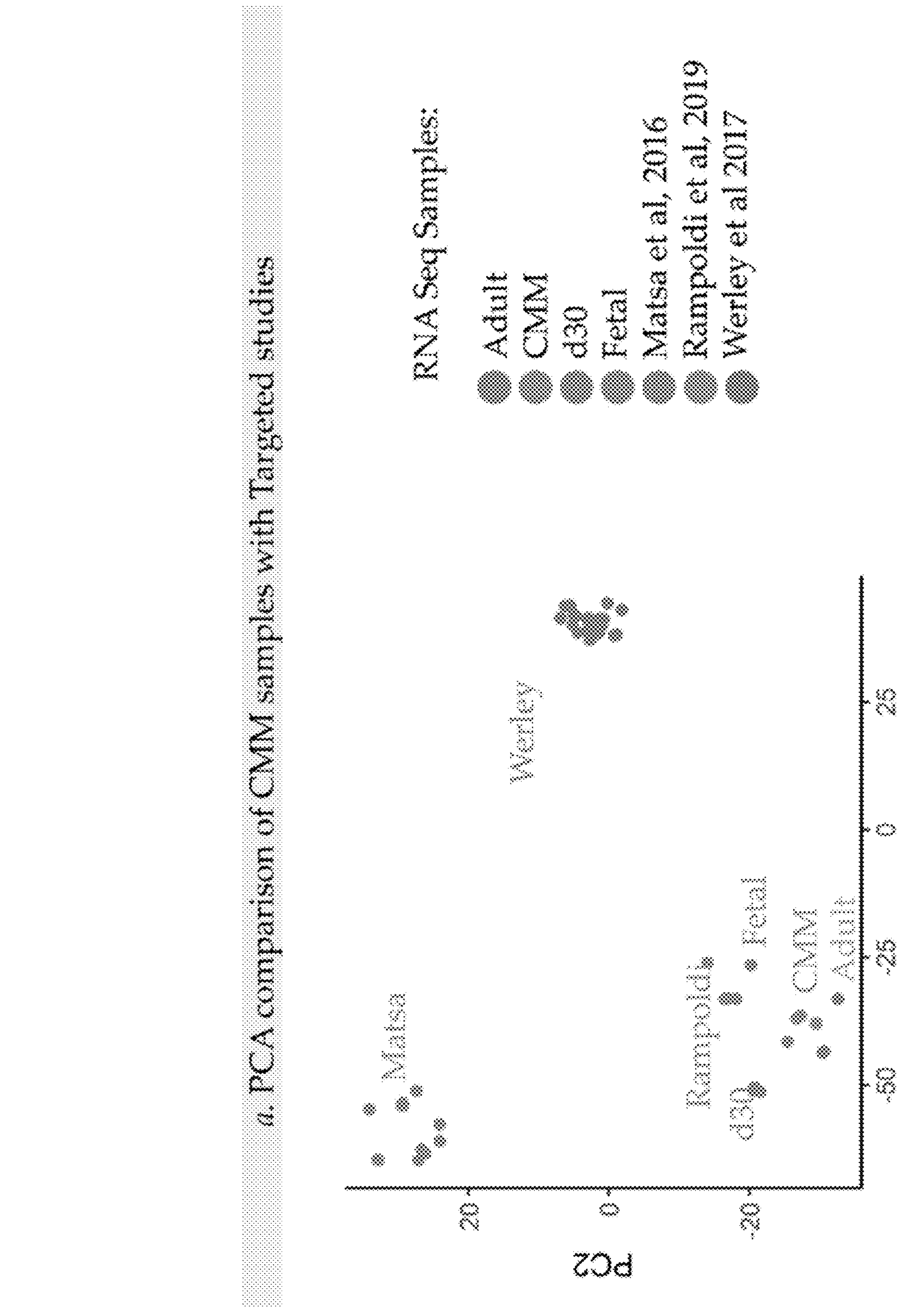
FIG. 9 shows comparative transcriptomic analysis, Related to FIG. 1. (a) Principal component analysis (PCA) showing the two chief principal components explaining variance between transcriptomic data for various published studies, our control group (d30), CMM, as well as fetal and adult heart. PCA plot showed that control conditions are well prepared transcriptomically with high quality cardiomyocytes which are closer to the fetal and adult myocytes. CMM further enhanced their maturation towards an adult-like phenotype. (b) PCA comparison of CMM samples with published EHT/3D tissue. Cells on CMM (30-day culture) show enhanced maturation when compared to monolayer 2D culture of 30 days (d30)/60 days (d60) and engineered heart tissue/3D culture. (c) Enrichment score of top ontologies from principal component (PC) 1 versus PC2 from (b) PCA analysis. PC1 signifies several ontologies related to metabolism and fatty acid oxidation and is more enriched in CMM while most PC2 enriched genes are related to vitamin B12 and complement activation pathway. Striated muscle contraction ontology is activated in both PC1 and PC2 but the $-\log_{10}$ pVal is higher in PC1.
Figure 9:
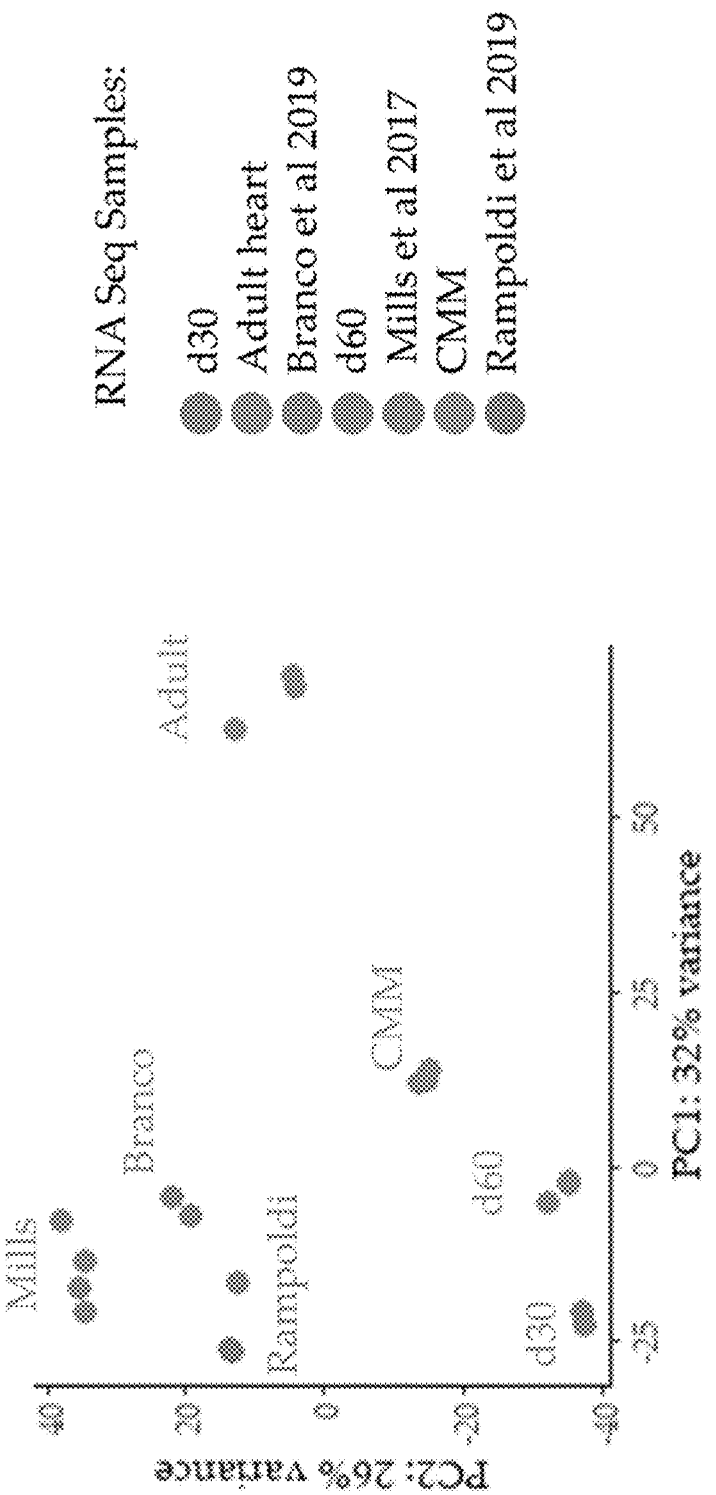
Figure 9:
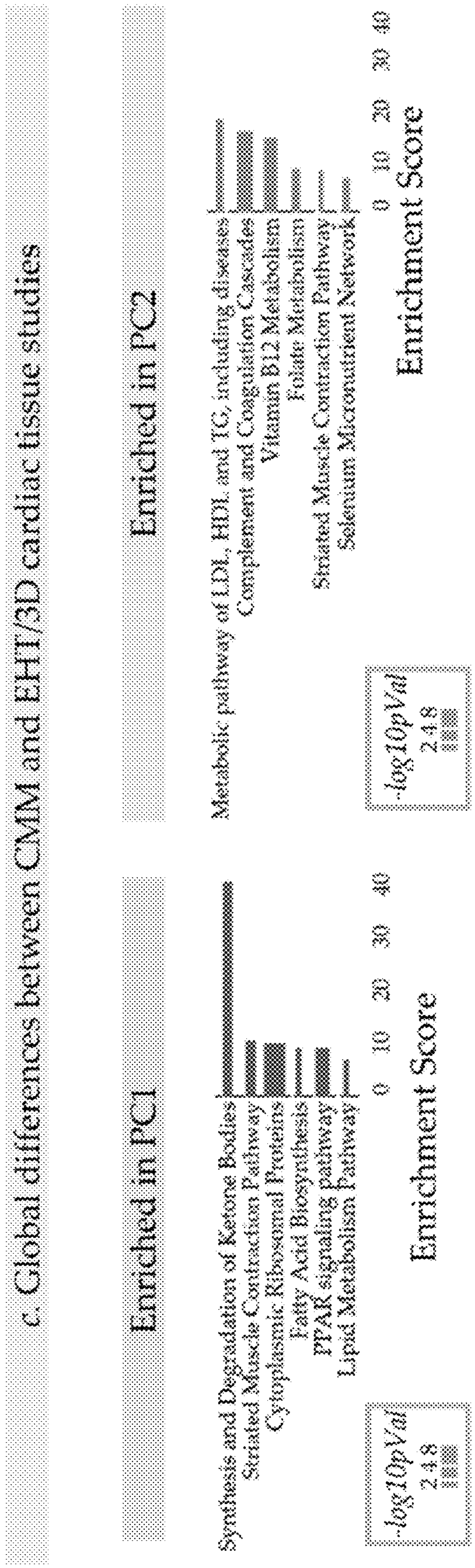
Figure 10:
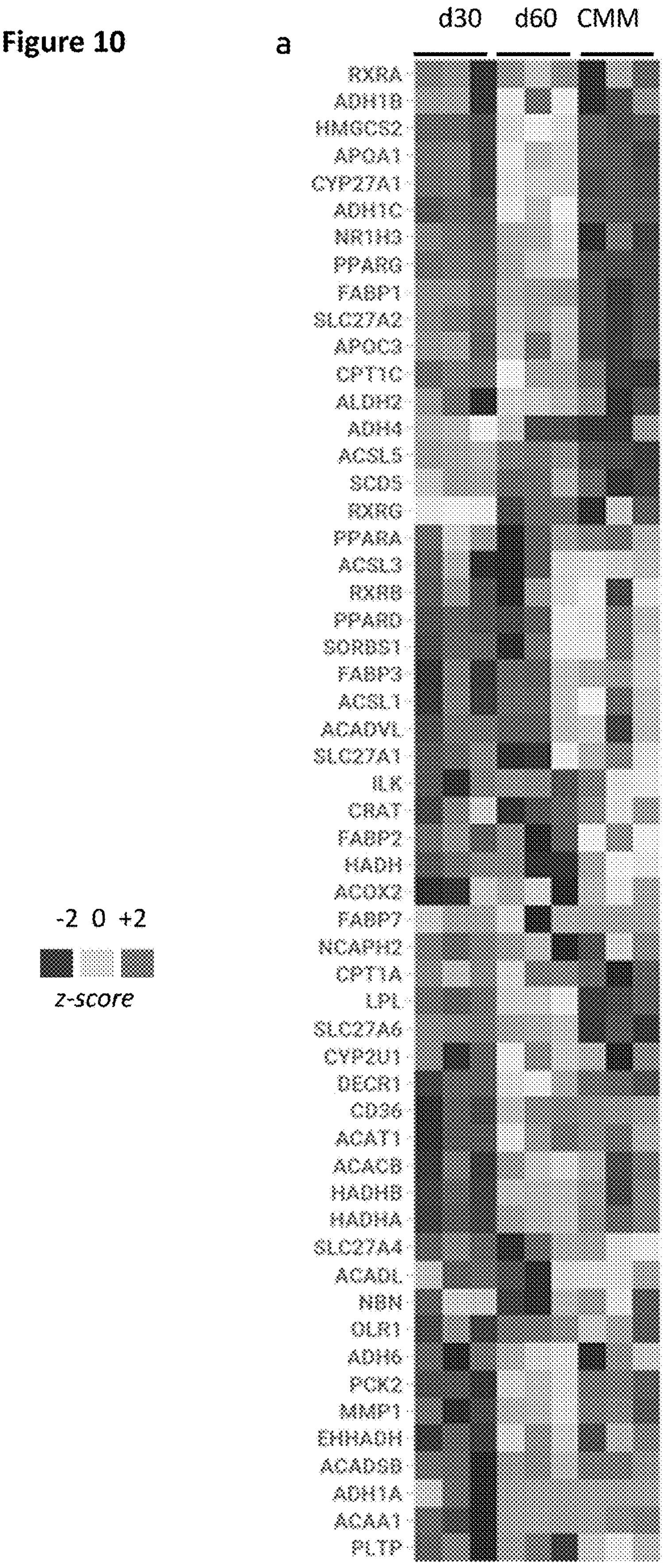
FIG. 10 shows heatmaps of differentially regulated genes (either condition) in relevant ontologies, Related to FIG. 1. (a) Genes in fatty acid oxidation (fao) and Ppar signaling. (b) Citric acid cycle (TCA) and electron transport chain (ETC) (c) Muscle contraction (GO:0060048) and calcium.
Figure 10:
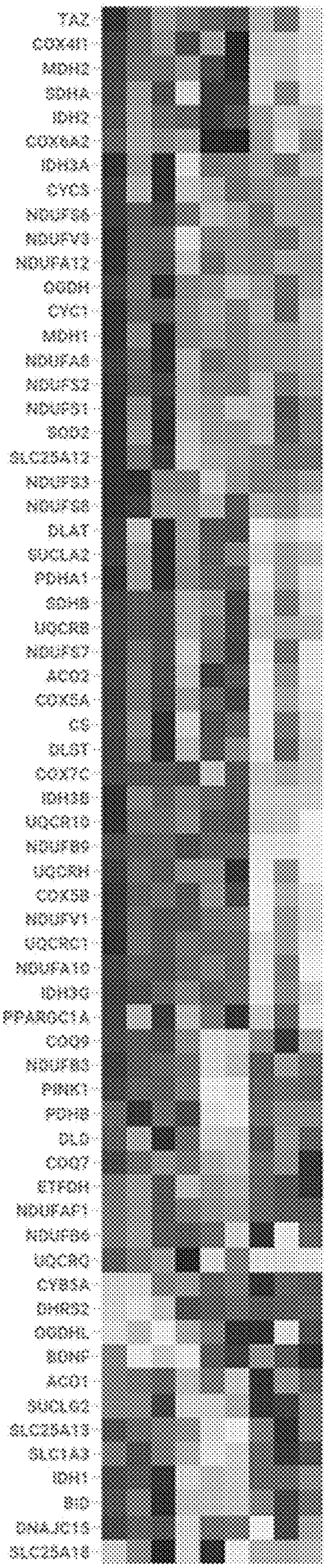
Figure 10:
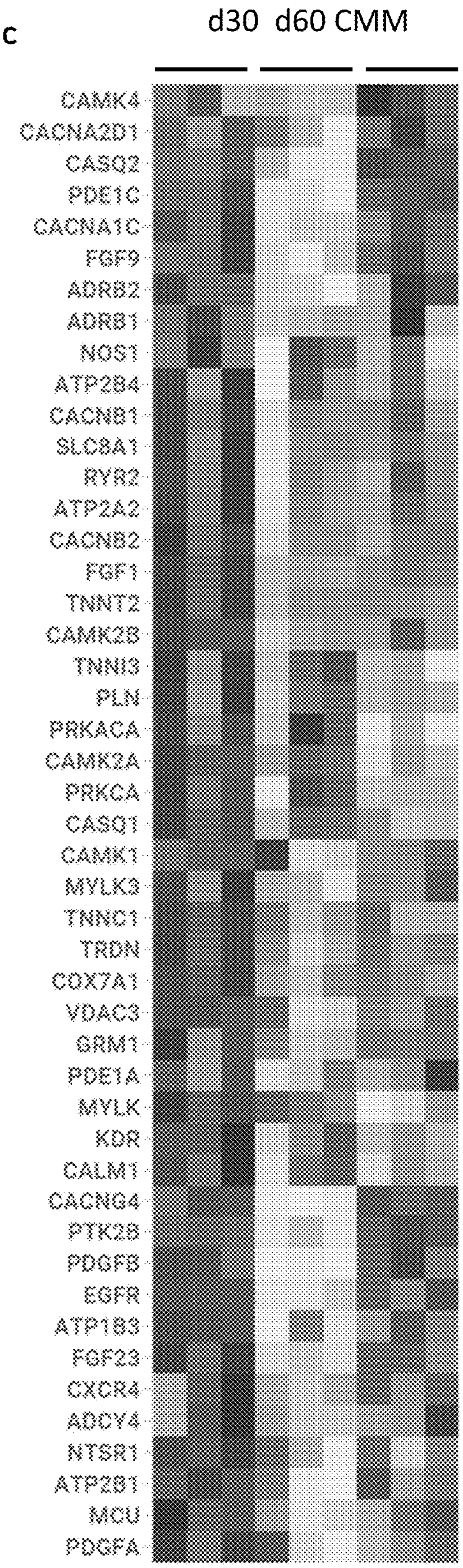

Imaging in FIGS. 4*f* and 9 is with pixel size 0.070×0.070 μm, image size of 268×133 μm and 8 Tiles.

Banding patterns prevalent as signatures of cardiac maturity were measured using ImageJ and analyzed using custom MATLAB scripts. Banding frequency was measured as the spatial metric between peak intensities of myosin light chain in the respective α-Actinin and cardiac troponin (cTnT) images.

Flow Cytometry. Cells were detached from the substrate with TrypLE Airyscan (Gibco), quenched with excess medium, and washed thrice with phosphate-buffered saline (PBS). Isolated cells were either labeled with the requisite dye (Mitotracker-Green at 100 nM for 15 minutes, and washed twice with PBS), or fixed in 4% paraformaldehyde in PBS and stained with primary and secondary antibodies with method described previously(Hubbi et al., 2013; Kshitiz et al., 2012). Primary antibodies used were: Myosin Light Chain 2 (Abcam ab79935), sarcomeric alpha actinin (ThermoFisher MA1-22863) and cardiac troponin T (ThermoFisher MA5-12960). Cells were analyzed in a BD FacsARIA II, and analyzed using Flowing software (Turku University). Gating was performed using the requisite negative controls in each channel with unlabeled cells.

Immunoblots. Three different biological replicates (batches) were generated using separate cultures/cardiac differentiations of iPSCs for immunoblots. Samples were harvested and lysed in buffer containing radioimmunoprecipitation assay lysis buffer (Cell Signaling Technology 9806), protease inhibitors (Sigma-Aldrich P8340) and phosphatase inhibitors (Sigma-Aldrich 4906845001-PhosSTOP). Protein concentration was quantified using bicinchoninic acid assay kit (Thermo Fisher Scientific). Proteins were denatured 95° C. for 5 minutes in SDS and 20 µg of samples were loaded on 4-12% NuPAGE™ Bis-Tris Gel (Thermo Fisher Scientific NP0322BOX). They were transferred to polyvinylidene difluoride (PVDF) membranes, and subsequently blocked with 5% BSA for 1 h at room temperature and incubated overnight at 4° C. with primary antibody—cardiac troponin I (Abcam ab47003); Troponin T (ThermoFisher MA5-12960), PDK1 (Cell Signaling Technology 5662), AceCS1 (Cell Signaling Technology 3658), FAS (Cell Signaling Technology 3180), PFPK (Cell Signaling Technology 12746). For Total OxPhos primary antibody (Abcam ab110413), samples were prepared in lysis buffer (as above) but loaded onto the gel without denaturation. Proteins samples were transferred onto PVDF membranes at 4° C. and equal protein loading was verified with Ponceau S staining solution (Cell Signaling Solution 59803). Following the primary antibody incubation, membranes were washed several times before incubation with GAPDH (Cell Signaling Technology 5174) for 1 h at room temperature. Subsequently, samples were incubated with horseradish peroxidase-linked anti-rabbit or mouse IgG secondary antibody (GE healthcare NA9340 or NA9310) for 1 h at room temperature. An enhanced chemiluminescence reagent (Thermo Fisher Scientific 34095) was used to visualize the bands. Semi-quantification of protein was conducted by comparison against the GAPDH bands using ImageJ software.

Mitochondrial respiration. Cellular energetics was monitored using the Seahorse Bioscience XF instrument in intact cells (non-permeabilized cells) and permeabilized cells(Afzal et al., 2017; Salabei et al., 2014). Intact cell respiration was monitored to evaluate the contribution of oxidative phosphorylation versus glycolysis, whereas permeabilized cell respiration was used to monitor electron transport chain (ETC) complex function/activity using ETC complex specific substrates and fatty acid oxidation.

Respiratory rates were measured as basal rates (in the absence of added compounds/metabolic inhibitors) and after injection of compounds through injection ports of Seahorse XF analyzer during the assay run. Specific components of ETC or glycolysis (in intact cells) were inhibited to investigate components of metabolism. Oligomycin (404) was used to inhibit mitochondrial FIFO-ATP synthase, rotenone (204) to inhibit Complex 1 of ETC, antimycin A (204) to inhibit complex 3 of ETC, FCCP (204) to uncouple mitochondria for quantification of maximum respiratory capacity and iodoacetate (100 µM) to inhibit glycolysis (glyceraldehyde-3-phosphate dehydrogenase). The compounds were prepared as stock solutions and dissolved in the assay media immediately before the experiment. For intact cell respiration, Seahorse XF Base Medium (Part #102353-100) with addition of D-glucose (11 mM) and glutamine (2 mM) were used.

For permeabilized cell respiration, iPSC-CMs were permeabilized using 2 nM of Seahorse XF Plasma Membrane Permeabilizer (Part #102504-100). In permeabilized cells only OCR is measured. Mitochondria respiration were assayed using Buffer (pH 7.2) containing 137 mM KCl, 2 mM $KH_2PO_4$, 0.5 mM EGTA, 2.4 mM $MgCl_2$, 20 mM HEPES with 0.2% fatty acid-free BSA (Sigma). Respiration rates were normalized to the protein concentration using BCA assay. Complex I respiration were evaluated by 5 mM glutamate and 5 mM malate (G/M) to evaluate State 4 respiration; 4 mM ADP was then injected to evaluate State 3 respiration. Maximal respiratory capacity (uncoupled mitochondria) was measured by injecting 204 FCCP. Coupling of Electron Transport Chain respiration to ATP synthesis were evaluated using the ATP synthase inhibitor oligomycin (4 uM). Complex II respiration were measured using 5 mM succinate. Fatty acid oxidation was measured by injecting 200 uM of Palmitoyl-1-carnitine chloride/2.5 mM Malate and assessing the increase in OCR.

Particle Image Velocimetry (PIV) analysis. Time lapse movies of three given conditions were taken using a 4× magnification lens to capture the contraction dynamics over a 2.2×1.5 mm field of view (FOV). The images were taken using the EVOS™ Imaging system with a camera (X) equipped for image acquisition at video rate (60 Hz) over a period of 20 seconds. Particle image velocimetry metrics was employed to track the dynamical movements of cell monolayers during the period of contraction. From the time-lapse images, the local contrast was sufficient to track movement of the monolayers over the 140×140 um interrogation window. Further spatial and temporal filtering was employed to assess correct measurement of particle velocities(Thielicke, 2014). These metrics were used to assess the instantaneous velocities of the monolayer over the field of view and the beating frequency. Furthermore, metrics over localized areas were used to measure the temporal signatures in the contractile moments and the directional movement of the monolayer during contraction.

Transmission Electron Microscopy. Transmission Electron Microscopy was performed by Dr. Maya Yankova at the UConn Health Central Electron Microscopy Facility. To assess the subcellular organizational changes of cardiomyocytes cultures for the two varying topographies, samples were prepared for Transmission Electron Microscopy using standard protocols. Briefly, post culturing cells in flat and CMM, samples were fixed in 2%/2.5% paraformaldyhyde/glutaraldehyde solution overnight. Following fixation, samples were treated with 1% osmium tetroxide and embedded in Epon resin for sectioning. Thin, 70 nm sections were imaged using X imaging setup at various locations using Hitachi H-7650 EM. Organelle structures such as mitochondria size and fusion, sarcomeric structures and banding were visually assessed and imaged.

Traction Force Microscopy. Polyacrylamide substrates were prepared and functionalized to measure traction forces generated by cardiomyocytes from standard gel preparation protocols(Aratyn-Schaus et al., 2010; Fischer et al., 2012; Wang and Pelham, 1998). Briefly, coverslips for gel attachment were cleaned with ethanol and sonication, treated with air plasma, and silane-activated with 0.5% glutaraldehyde and 0.5% (3-Aminopropyl)triethoxysilane. Coverslips (for TFM) and nanopatterned poly(urethane acrylate) molds (for nanoTFM) for beads coating were treated with air plasma, coated with 0.01% poly-L-lysine (PLL), and then coated with carboxylate-modified fluorescent microspheres (0.2 um; Thermo Fisher). Gel precursor solution containing 7.5% acrylamide and 0.15% bis-acrylamide was degassed for 30 mins and mixed with 0.1% tetramethylethylenediamine and 0.1% ammonium persulfate before sandwiched between silane-activated coverslips and beads-coated coverslips or molds for 20 mins. Gels were functionalized using 1 mg/mL suflo SANPAH (ThermoFisher) for 10 min under UV lamp (UV StratAligner 1800) and incubated in 30 ug/ml collagen type I (Thermo Fisher) overnight at 4° C. Gels were sterilized under UV for at least 2 hours before cell seeding.

Harvested cardiomyocytes from flat and nano substrates were seeded on functionalized gels and incubated for 36 hours prior to imaging. Differential Interference Contrast (DIC) and fluorescent beads were imaged using a Zeiss Observer Z 1. Monolayer contractions were imaged over a period of 20 seconds to accurately assess contraction dynamics of at least 4-6 cell cycles. Cells were paced at different rates by coverslips with cells in a chamber connected to grass stimulator with 4.0 ms pulse duration and 5V of current at which one to one pacing was observed at different pacing rates. Cells were then detached by trypsinization, and stress-free reference images were recorded. Traction stress calculations were performed by comparing images containing beads position displaced by cellular traction force and reference images using particle image velocimetry as described in detail (Sabass et al., 2008). Strain energy calculations were made as mentioned earlier to assess contractile energies of cardiomyocytes (Sabass et al., 2008).

Cyto-calcium, Action potential and redox handling. Cytoplasmic calcium and redox status of iPSC-CMs using spinning disk confocal microscope (Olympus/Andor Revolution XD) was monitored. 3$^{rd}$ gen. lentiviral probes using ViraPower™ Lentiviral mix was generated and transduced iPSC-CMs using MOI 5 (multiplicity of infection) that generated good signal to noise ratio. Cytoplasmic targeted roGFP-Grx1 probes(Gutscher et al., 2008), Calcium probe (genetically encoded $Ca^{2+}$ indicators (GECIs)-GCamP6f (Hubbi et al., 2013), Arclight(Jin et al., 2012) and Varnam (Kannan et al., 2018) were obtained from Addgene and transferred to pENTR™/SD/D-TOPO® vector using PCR. The vector was sequence verified and then transferred to pLEX_307 vector (Addgene plasmid #41392) that contains the EF1α promoter using the LR reaction. The vector was sequence verified and transferred to pLEX_307 vector using the LR reaction. The virus was generated for each probe in HEK293-FT cells using an optimized mix of three packaging plasmids (pLP1, pLP2, and pLP/VSVG). The virus was concentrated using PEG-it™ Virus Precipitation Solution (SBI biosciences) that also removes HEK293-FT cell medium. MOI was calculated using qRT-PCR and MOI=5 was found to be optimal for these probes in iPSCs-CMs.

To monitor the florescence signal from cells transduced with probes, cells were plated at a density of 200,000 per $cm^2$ on cultured surfaces for at least 10-15 days prior to imaging, to achieve cell-cell coupling. During the experiment, continuous perfusion of modified Tyrode solution was performed at 37C with pH 7.4 containing (in mM) 130 NaCl, 5 KCl, 1 $MgCl_2$, 2 $CaCl_2$), 20 Na-HEPES, 11 glucose, 2 pyruvate, 0.1% fatty acid free-BSA.

Florescence from cells (transduced with probes) was collected separately at a frame rate of 5112×512 using an electron-multiplying charge-coupled device (EMCCD) camera using Andor Revolution X1 Spinning Disk confocal inverted microscope. Data was acquired with 2×2 pixel binning. ROS (roGFP2-Grx) probes were excited with 405 nm and 488 nm laser and emission was detected using bandpass filter of 500 nm-554 nm. The image 405 nm image was divided by 488 nm image (pixel by pixel), and the values are reported as the ratio of 405/488. Recovery of glutathione pool was monitored for 180-240 sec before the utilization of diamide (oxidized) and DTT (reduced) to obtain min and max signal. Recovery timepoint of 60 seconds were selected as the signal was stable 60 sec in most cells. Cells transduced with cytoplasmic GCamp6f were excited at 488 nm and emission was detected using bandpass filter of 500 nm-554 nm. Cells transduced with Arclight were excited at 488 nm and emission was collected using bandpass filter of 500 nm-554 nm. The data was analyzed using image J (NIH).

To investigate calcium content of the sarcoplasmic reticulum (SR), Fura2 (ThermoFisher 3 uM) loaded cells were perfused with caffeine. Cells were initially perfused with modified Tyrode solution at 37C (pH 7.4) containing (in mM) 130 NaCl, 5 KCl, 1 MgCl2, 1.2 CaCl2, 20 Na-HEPES, 10 glucose, 1 pyruvate, 0.1% fatty acid free-BSA. After pacing the cells at 0.5 Hz for 30-40 sec, cells were perfused with the modified Tyrode buffer containing caffeine (10 mM). Images were analyzed using image J (NIH). Line plots (trace plots) were generated for both action potential and calcium transients by calculating average intensity (and standard deviation) from 3 biological batches with >100 cells for each timepoint and plotting it against the time (using R).

Steiner tree based Protein-Protein Interaction Map. Networks intending to generate hypotheses for proteins mediating the transcriptomic response related to specific ontologies from the ECM coated nanofabricated substrate was derived. Our method prioritizes including the genes from a particular gene set that are differentially up-regulated in the nanofabricated structures and the ECM receptors (integrins) that are supposed to cause the response.

The networks are generated from the protein-protein interactions taken from BioGRID. In order to get the gene set related subnetwork of differentially expressed genes, the Prize Collecting Steiner Tree algorithm was modified. The prize for including a differentially regulated gene that is a member of the gene set under consideration is set as $$p_g = \alpha(1 + f_g\ I_{f_g>0}),$$

where $f_i$ is the log 2 fold change of the gene i, $I_{f_g}>0$ is the indicator function (i.e., $I_{f_g}>0=1$ if $f_g>0$, and 0 otherwise). The prize for an integrin whose ligand was coated on the substrate is P. The prize for all genes other than the ones in the gene set of interest or the receptors of interest are zero. Thus, they may be included in the network if they are needed to connect the selected integrins and up-regulated genes. The edges have costs associated with them that are related to the degree and differential expression of the nodes they connect. First, the degree of each gene i in the un-wieghted validated protein-protein interaction network from BioGRID is calculated as $$k_i = \sum_j e_{i,j}$$

Then, the cost of each edge (i,j) is set as $$c_{i,j} = \sqrt{\frac{k_i}{1 + I_{f_i>0}}\frac{k_j}{1 + I_{f_j>0}}}$$

where $I_{f>0}$ is again the indicator function. The numerator is the equivalent of symmetrical degree normalization of the adjacency matrix, while the denominator has the effect of decreasing the cost for edges that connect up-regulated edges. Overall, promiscuous and non up-regulated genes are penalized. The indicator function was used so that it isn't, per se penalizing down-regulation because down-regulation may either mean the shutting down of a signaling pathway or the participation of a particular gene in some complex dynamics.

The Prize Collecting Steiner Tree algorithm then attempts to join the genes with prizes using edges and any other out of set genes as needed to maximize the total gene prizes minus the total edge costs. A small set of genes needed to connect the gene set will be included by the algorithm, prioritized by their up-regulation and specificity (i.e., low degree in the PPI network). OmicsIntegrator2 was used to arrive at a solution to the optimization problem (Kedaigle A and E., 2018).

For FIG. 9*a*, all experimentally observed physical interactions were considered in building the Steiner Tree, while for FIGS. 9*b-d*, the Steiner Tree was constructed using only those genes marked as multi-validated according to BioGRID based on its confirmation in multiple studies or experimental systems Patch Clamp Electrophysiology. Cardiac cells differentiated on flat and CMM substrate (d30 and CMM cells) were harvested as single cell and plated on fibronectin coated cover slips followed by few days of culture in cardiac media to recover them before performing patch clamp and action potential recording. Action potential was recorded under whole-cell current clamp mode using an Axon Axopatch 200B amplifier and pclamp9 software (Molecular Devices, USA) at room temperature. Patch pipettes were pulled from borosilicate glass tubes to give a resistance about 10 MΩ when filled with pipette solution. Data were low-pass filtered at 1 kHz and digitized at a rate of 10 kHz. The bath solution contained 140 mM NaCl, 3 mM KCl, 1 mM CaCl2, 1 mM MgCl2, 10 mM HEPES, pH7.41 and the pipette solution was 145 mM KCl, 5 mM NaCl, 2 mM CaCl2, 2 mM MgCl2, 3 mM MgATP, 4 mM EGTA, and 10 mM HEPES, pH7.35. A 0.2 nA stimulation was applied for 2 ms to induce action potential firing. Nifedipine at 100 nM was used through a gravity-perfusion system until reach the maximum inhibition was achieved. MDP, MDR, APD20, APD50 and APD90 were analyzed using the pclamp10 software.

Cell culture and Treatment. Normal human ventricular cardiac fibroblasts were purchased from Lonza biosciences (CC-2904). Cells were cultured and expanded in cardiac fibroblast media (Millipore Sigma, 316-500). Experiments were performed at passage 4 of sub culture. Cells were replated on anisotropic and flat surfaces on an uncoated surface for 7 days before starting any treatment.

TOP (5 ug/ml) treatment was performed in serum free Dmem/f12 containing ITS (insulin transferrin selenium) solution (Thermo Fisher 41400045) and 0.1% BSA. Cells were washed twice with PBS before starting the Tgfβ treatment for 48 hours. Multiple biological batches were used for experiments but the passage number (p4) and confluency (70-80%) were kept the same in the experiments.

RNA isolation, RNA Sequencing and analysis. RNA was isolated using RNeasy™ Mini Kit (Qiagen). Bioanalyzer 2100 (Agilent) was used to check the RNA integrity and samples with RIN ~8 were used for library preparation. Library preparation and RNA sequencing were performed by Novogene. The data was aligned against NCBI GRCh38 genome assembly using the HISAT2 pipeline with default parameters and reads were counted using HTSeq. Deseq2 was used to calculate Fold changes and statistical significance (p-values) for differential expression. P-values for differential expression were calculated for the Wald test. IPA (ingenuity pathway analysis-Qiagen) was used for canonical pathway and predicted activation of transcriptional factors.

Gene sets from the Gene Ontology(12), KEGG(13), Msigdb(14), WikiPathways(15), and EBI(16) were used in the relevant pathway/ontology related transcriptomic analysis.

qRT PCR. RNA isolated using RNeasy™ Mini Kit (Qiagen) was converted into cDNA using High-Capacity cDNA Reverse Transcription Kit (ThermoFisher). Predesigned primers were purchased from integrated DNA technologies (IDT, PrimeTime qPCR Primer Assays) to run real-time PCR using intercalating dye with melting curve at the end of each assay. PowerUp SYBR Green Master Mix (ThermoFisher) was used in Biorad CFX384 thermal cycler to estimate the relative gene expression.

Statistical analysis. Students t-test was performed for most of the analysis unless otherwise mentioned. Data is presented as ±SD or ±SEM. Statistical significance is defined as the $p<0.05$ (*) $p<0.01$ () $p<0.001$ (*) or $p<0.0001$ (****).

For ontology related analyses, statistical significance and z-scores for the enriched differentially expressed genes in gene sets were calculated by transforming the individual gene level p-values to z scores using the inverse of the normal distribution, and then the sign was assigned by the direction of the fold change. Student's t-test was used to calculate p-value and correction for multiple testing was performed using false discovery rate (Benjamini-Hochberg) method.

Immunostaining and imaging. Cultured fibroblasts were washed multiple times with PBS before treating them with 4% paraformaldehyde (pH 7.4) for 15 min at room temperature for cell fixation. Cells were subsequently washed with cold PBS and permeabilized with permeabilization buffer containing PBS, 0.2% Triton X-100 and 0.1% BSA for 15 minutes. Permeabilized cells were then blocked with one-hour incubation with blocking buffer (1% BSA in PBS). Overnight incubated was performed with primary antibodies with subsequent 30 minutes incubation with secondary antibody. Following primary antibodies were used for labeling; Alexa fluor™ 594 phalloidin (ThermoFisher). Following Alexa Fluor Secondary Antibodies (ThermoFisher) were used: Alexa Fluor 568 (A-11004, A-11011), Alexa Fluor 488 (A32723, A32731). Image J (National Institutes of Health, Bethesda, MD, USA) was used to analyze the data.

Immunoblots. Cardiac fibroblasts were harvested and lysed in cell lysis buffer containing radioimmunoprecipitation assay lysis buffer (Cell Signaling Technology 9806), protease inhibitors (Sigma-Aldrich P8340) and phosphatase inhibitors (Sigma-Aldrich 4906845001-PhosSTOP). Bicinchoninic acid assay kit (Thermo Fisher Scientific) was used for protein concentration. For collagen, non-denatured samples (10 ug) were loaded on the tris acetate gels (Thermo Fisher Scientific) while other immunoblots were performed with denatured samples (95° C. for 5 minutes in SDS) before loading samples on 4-12% NuPAGE Bis-Tris Gel (Thermo Fisher Scientific). Proteins were then transferred to polyvinylidene difluoride (PVDF) membranes, and subsequently blocked with 5% BSA for 1 h at room temperature and incubated overnight at 4° C. with primary antibody. GAPDH loading control was used (Cell Signaling Technology 5174). Horseradish peroxidase-linked anti-rabbit or mouse IgG secondary antibody (GE healthcare NA9340 or NA9310) for 1 h at room temperature was used to visualize the protein bands using enhanced chemiluminescence reagent (Thermo Fisher Scientific). Protein quantification was performed using ImageJ software.

Enzyme-linked immunosorbent assay (Elisa). Cell culture supernatant was collected at the end of treatment (48 hours following treatment in serum free media) from 6 wells (100 ul from each well). Colorimetric sandwich enzyme-linked immunosorbent assay (ELISA) kits were used from R&D Systems (Igf1 DY291, MMP1 DY901B, Postn DY3548B) and Abcam (Vegfa ab119566, Opn ab100618). Elisa was performed following manufacturer's instructions and BioTek Synergy microplate reader was used to measure the absorbance. Protein secretion was estimated after normalizing the data with cell number from each well. Cell numbers were calculated using Countess 3 FL Automated Cell Counter (ThermoFisher) after harvesting the cell from each well following 48 hours of treatment and media collection. Per well protein concentration was estimated after calculating the calibration curve for each Elisa kit

Example 2: Cardiac Mimetic Matrix Synergistically Promotes Maturation of Cardiomyocytes A substratum was created matching the chemistry, elasticity, and topographic ultrasctructure of the extracellular matrix that adult cardiomyocytes respond to. Integrin alpha and beta subunits combine to form more than 20 different heterodimers with varying ligand specificity, and transduce extracellular chemical and mechanical information to intracellular signaling modulating various cellular phenotypes, including cell fate and differentiation (Kshitiz et al., 2012; Mamidi et al., 2018). Adult human hearts transcriptomic data was used (Choy et al., 2015; He et al., 2016; Lopez-Acosta et al., 2018; Zhao et al., 2019), and identified genes encoding integrin receptor subunits upregulated in comparison to hiPSCs (FIG. 1*a*). Adult human cardiomyocytes expressed higher levels of transcripts encoding integrins specific for widely used matrix peptide motifs, including RGD and collagen binding alpha11, alpha10, and alpha1 subunits. Alpha7 and alpha3, receptors for laminin were also highly expressed in adult heart, although alpha6 expression was low (Burridge et al., 2014; Sung et al., 2020). In addition, alpha8 was also upregulated with high specificity for Nephronectin, responsible for cardiac development and cardiomyocytes adhesion (Patra et al., 2011; Patra et al., 2012) (FIG. 1*a*).

It was surmised that combining nano-architectured substrates, elasticity matching heart tissue, and adult-cardiomyocytes inspired ligand chemistry would, in combination, affect hiPSC-CM maturation. Based on transcriptomic analysis of integrins present in the adult human heart, RGD, GFOGER (SEQ ID NO: 11) (a commercial alternative to GFOGR (SEQ ID NO: 14)), and Nephronectin (SEQ ID NO: 13) was conjugated in equal amounts with hydrogel patterns into nano-architectured arrays produced by anisotropic nanowrinkle pattern transfer to create a cardiac mimetic matrix (CMM) substrate (FIG. 1*b*). A nanowrinkled polydimethylsiloxane (PDMS) substrate was created, which recapitulates cardiac matrix ultrastructure more than completely anisotropic arrays (Caulfield and Janicki, 1997; Silva et al., 2020), transferred the pattern to polyurethane molds, and thereafter into polyacrylamide (PA) hydrogels matching heart matrix elasticity. A double transfer was necessitated because PA required mold non-permeable to atmospheric oxygen. Scanning electron microscopy (FIG. 1*c*, Sla-b), and atomic force microscopy (FIG. 1*d-f*, S1*c*) showed that nanowrinkled PDMS patterns transferred to PUA (FIG. 1*c*) and thereafter to the hydrogel (FIG. 1*d-f*) were anisotropic, similar to the aligned bundles of collagen fibers in the heart (FIG. 1*f*, S1*d*)(Kshitiz et al., 2014) with matching substrate elasticity(Kshitiz et al., 2012). Raman spectroscopic confocal microscopy confirmed a spatially uniform and equal distribution of RGD, GFOGR (SEQ ID NO: 14), and Nephronectin conjugation (FIG. 1*g-h*). The capability of CMM to mature differentiated hiPSC-CMs was tested. hiPSCs were differentiated into beating cardiomyocytes using well established protocol (Burridge et al., 2014), metabolically purified using lactate yielding >95% TNNT2$^+$ cells (FIG. 8*e-f*) (Burridge et al., 2014; Tohyama et al., 2013), of high quality, comparable with multiple studies (FIG. 9*a-c*). Cells were plated on tissue-culture plastic with fibronectin as control for a total of 30 days (d30), for prolonged culture of 60 days as positive control (d60), or on CMM surfaces on day 13-14 until day 30 (FIG. 1*i*). After termination of the experiment, RNA was collected, sequenced, and analyzed, as well as functional tests performed. It was found that culture on CMM resulted in significant, and substantial upregulation of important genes related to key characteristics of ventricular cardiomyocytes, including calcium handling (CAMK2D, CASQ2, PLN, TRDN), cardiac development (MYOM2, TTN, MYBPC3, CAV3), and cardiac-type metabolism (PFKM, PDHB, NEFL2, NNT, NOS1, GSR) (FIG. ij, 10).

Figure 11:
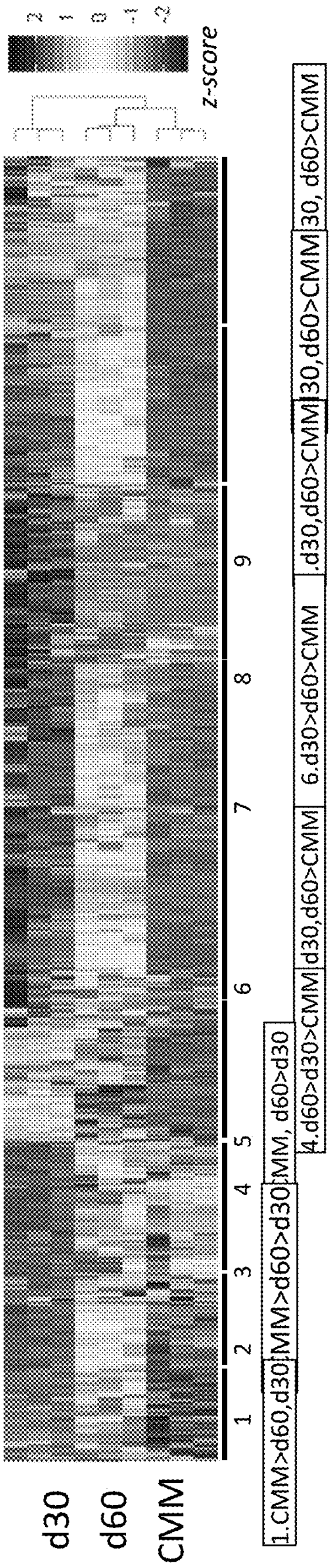
FIG. 11 shows hierarchical clustering (samples and transcripts), Related to FIG. 1. CMM shows upregulation in cluster 1-3 and downregulation in cluster 4-9.

Example 3: CMM Accelerates Systemic Gene Transcription Towards an Adult-Like State Considering the short period of culture on CMM, many gene sets were found to be different in CMM vs d30 ($p<0.05$), surprisingly most being related to cardiac function (FIG. 1*k*). CMM resulted in upregulation of several key ontologies related to cardiac electrophysiological development (Vent Card AP, cardiac conduction, SR Calcium), structural maturation (muscle structure, muscle contraction) and metabolic processes (OxPhos, cellular respiration, NADH Complex, mitochondrial respiratory chain biogenesis and organization) (FIG. 1*k*). Global transcription was compared in cells cultured on CMM, on control substrate for 30 and 60 days with published data of adult human heart samples (Choy et al., 2015; Dias et al., 2018; He et al., 2016; Lewandowski et al., 2018). Principal Component Analysis (PCA) of two largest components (accounting for 75% of variance) showed a strong linear regression suggesting a systemic movement of cellular transcription towards a more adult-like state (FIG. 1*l*). This regression could be construed as a cardiac maturation vector, with cells cultured on CMM being more adult-like than d30, as well as ahead of d60 (FIG. 1*m*). Hierarchical clustering on z normalized data showed enrichment of gene-sets in CMM (cluster-1) related to cardiac muscle maturation, ECM binding, collagen synthesis, assembly, cross-liking, and organization (FIG. 1*n*, 11, Tables 2-3), indicating that hiPSC-CMs were highly receptive to physiological matrix; as well as gene-sets related to mature actomyosin assembly, striation, and increased contractility (cluster-2). Other gene-sets also directed towards a trend of increased cardiac maturation on CMM (FIG. 11, and Table 2-3).

TABLE 2

| Upregulated in CMM | | |
|---|---|---|
| Clust_1_ID | Clust_1_Description | −log10padj |
| GO: 0030020 | extracellular matrix structural constituent conferring tensile strength | 4.736 |
| GO: 0005201 | extracellular matrix structural constituent | 4.124 |

TABLE 2-continued

| Upregulated in CMM | | |
|---|---|---|
| GO: 0005518 | collagen binding | 3.090 |
| GO: 0022836 | gated channel activity | 1.971 |
| GO: 0005267 | potassium channel activity | 1.421 |
| GO: 0005261 | cation channel activity | 1.327 |
| REAC: R-HSA-2022090 | Assembly of collagen fibrils and other multimeric structures | 6.085 |
| REAC: R-HSA-1474290 | Collagen formation | 5.737 |
| REAC: R-HSA-1650814 | Collagen biosynthesis and modifying enzymes | 5.645 |
| REAC: R-HSA-1442490 | Collagen degradation | 4.528 |
| REAC: R-HSA-8948216 | Collagen chain trimerization | 4.439 |
| REAC: R-HSA-1474244 | Extracellular matrix organization | 3.959 |
| REAC: R-HSA-216083 | Integrin cell surface interactions | 3.596 |
| REAC: R-HSA-1474228 | Degradation of the extracellular matrix | 2.862 |
| REAC: R-HSA-2243919 | Crosslinking of collagen fibrils | 2.219 |
| REAC: R-HSA-9006934 | Signaling by Receptor Tyrosine Kinases | 2.131 |
| REAC: R-HSA-3000178 | ECM proteoglycans | 1.729 |
| **Clust_2_ID** | **Clust_2_Description** | **−log10padj** |
| GO: 0003015 | heart process | 9.700 |
| GO: 0008016 | regulation of heart contraction | 9.009 |
| GO: 0060047 | heart contraction | 8.980 |
| GO: 0006941 | striated muscle contraction | 4.918 |
| GO: 0051239 | regulation of multicellular organismal process | 4.696 |
| GO: 0006936 | muscle contraction | 4.432 |
| GO: 0002027 | regulation of heart rate | 4.276 |
| GO: 0060048 | cardiac muscle contraction | 4.138 |
| GO: 0030054 | cell junction | 8.387 |
| GO: 0071944 | cell periphery | 7.424 |
| GO: 0031674 | I band | 7.224 |
| GO: 0042383 | sarcolemma | 7.224 |
| GO: 0030018 | Z disc | 6.560 |
| GO: 0030016 | myofibril | 6.411 |
| GO: 0043292 | contractile fiber | 6.210 |
| **Clust_3_ID** | **Clust_3_Description** | **−log10padj** |
| GO: 0003012 | muscle system process | 17.419 |
| GO: 0006936 | muscle contraction | 15.251 |
| GO: 0060047 | heart contraction | 11.269 |
| GO: 0008016 | regulation of heart contraction | 9.596 |
| GO: 0061061 | muscle structure development | 8.889 |
| GO: 0002026 | regulation of the force of heart contraction | 6.109 |
| GO: 0001508 | action potential | 5.852 |
| GO: 0060048 | cardiac muscle contraction | 5.768 |
| GO: 0061337 | cardiac conduction | 5.645 |
| GO: 0086001 | cardiac muscle cell action potential | 5.560 |
| GO: 0070252 | actin-mediated cell contraction | 5.459 |
| GO: 0055001 | muscle cell development | 5.396 |
| GO: 0030239 | myofibril assembly | 5.262 |

TABLE 3

| Down regulated in CMM | | |
|---|---|---|
| **Clust_4_ID** | **Clust_4_Description** | **−log10padj** |
| KEGG: 04976 | Bile secretion | 1.624 |
| WP: WP716 | Vitamin A and Carotenoid Metabolism | 1.798 |
| WP: WP4917 | Proximal tubule transport | 1.330 |
| **Clust_5_ID** | **Clust_5_Description** | **−log10padj** |
| KEGG: 00220 | Arginine biosynthesis | 1.833 |
| KEGG: 01230 | Biosynthesis of amino acids | 1.335 |
| REAC: R-HSA-70635 | Urea cycle | 2.328 |
| **Clust_6_ID** | **Clust_6_Description** | **−log10padj** |
| GO: 0061041 | regulation of wound healing | 9.547 |
| GO: 0061045 | negative regulation of wound healing | 9.534 |
| GO: 1903035 | negative regulation of response to wounding | 8.975 |
| GO: 1903034 | regulation of response to wounding | 8.140 |
| GO: 0065008 | regulation of biological quality | 7.835 |
| KEGG: 05200 | Pathways in cancer | 1.405 |
| REAC: R-HSA-140877 | Formation of Fibrin Clot | 2.688 |
| REAC: R-HSA-382551 | Transport of small molecules | 2.404 |
| REAC: R-HSA-425407 | SLC-mediated transmembrane transport | 1.344 |
| **Clust_7_ID** | **Clust_7_Description** | **−log10padj** |
| KEGG: 04550 | Signaling pathways regulating pluripotency of stem cells | 2.056 |
| KEGG: 04350 | TGF-beta signaling pathway | 1.971 |
| KEGG: 04151 | PI3K-Akt signaling pathway | 1.829 |
| KEGG: 05323 | Rheumatoid arthritis | 1.332 |
| REAC: R-HSA-500792 | GPCR ligand binding | 2.532 |
| REAC: R-HSA-373076 | Class A/1 (Rhodopsin-like receptors) | 1.479 |
| **Clust_8_ID** | **Clust_8_Description** | **−log10padj** |
| KEGG: 04977 | Vitamin digestion and absorption | 2.520 |
| REAC: R-HSA-174824 | Plasma lipoprotein assembly, remodeling, and clearance | 1.698 |
| REAC: R-HSA-8964043 | Plasma lipoprotein clearance | 1.446 |
| **Clust_9_ID** | **Clust_9_Description** | **−log10padj** |
| KEGG: 04975 | Fat digestion and absorption | 2.865 |
| KEGG: 04977 | Vitamin digestion and absorption | 2.153 |
| KEGG: 04974 | Protein digestion and absorption | 1.867 |
| KEGG: 00830 | Retinol metabolism | 1.560 |
| KEGG: 04979 | Cholesterol metabolism | 1.487 |
| REAC: R-HSA-425407 | SLC-mediated transmembrane transport | 2.284 |
| REAC: R-HSA-1500931 | Cell-Cell communication | 2.065 |
| REAC: R-HSA-8963888 | Chylomicron assembly | 2.048 |
| REAC: R-HSA-446728 | Cell junction organization | 1.758 |
| REAC: R-HSA-382551 | Transport of small molecules | 1.716 |

TABLE 3-continued

| Down regulated in CMM | | |
|---|---|---|
| REAC: R-HSA-6806942 | MET Receptor Activation | 1.304 |
| WP: WP2882 | Nuclear Receptors Meta-Pathway | 2.201 |

GO: BP
GO: CC

Example 4: CMM Accelerates Transcriptional Program for Cardiac Development

Figure 2:
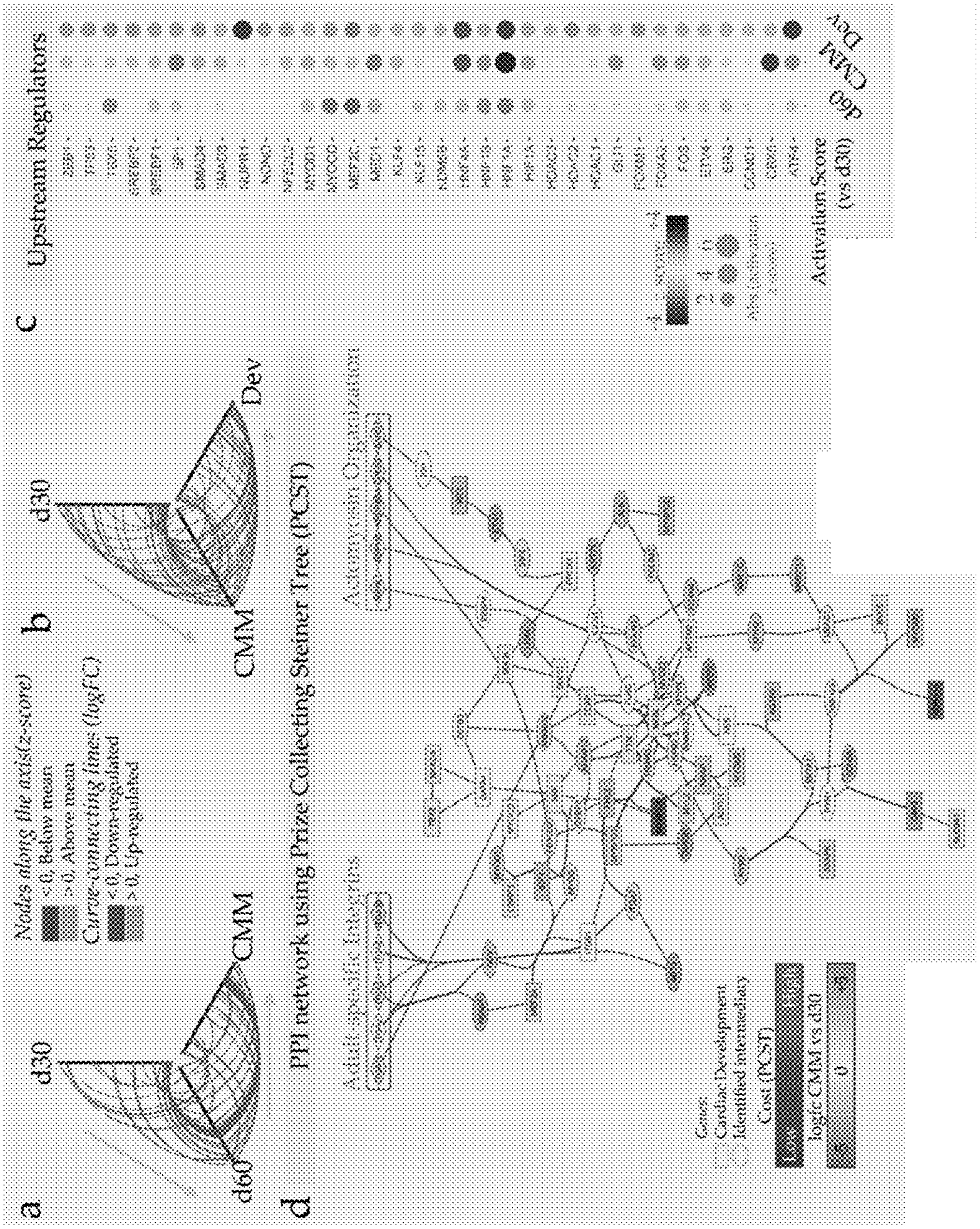
FIG. 2 shows CMM transcriptionally upregulates cardiac development. (a-b) Hive plots showing changes in gene expression of cardiac development genes between (a) d30, d60, and CMM, and (b) d30, CMM, and developed (Dev) heart. (c) Activation scores of transcription factors (TFs) between d60, CMM and Dev in comparison with d30 culture. (d) A subnetwork of protein-protein interactions relating input: (i) integrins targeted in CMM, and (ii) top expressed genes in actomyosin organization ontology to target: cardiac development genes. Details in methods Predicted intermediary genes are in ovals, grayscale indicate CMM vs d30 expression, and are listed for a path-length of 5 (from inputs to target) in (e). (f) The number of target genes activated or reached from either inputs against the maximal lengths of paths through the network. (g) The set of targets, i.e., cardiac development genes activated by the Integrins and actomyosin organization genes with path lengths of 5 or less in the network constructed from multi-validated PPIs. (h) Relative quantification using RT-PCR of key genes associated with cardiac maturation, Details in methods for individual components in CMM. (i) Heatmap with relative quantification (RQ) of select cardiac transcripts expression using RT-PCR on different substrates (with and without matrix).
Figure 2:
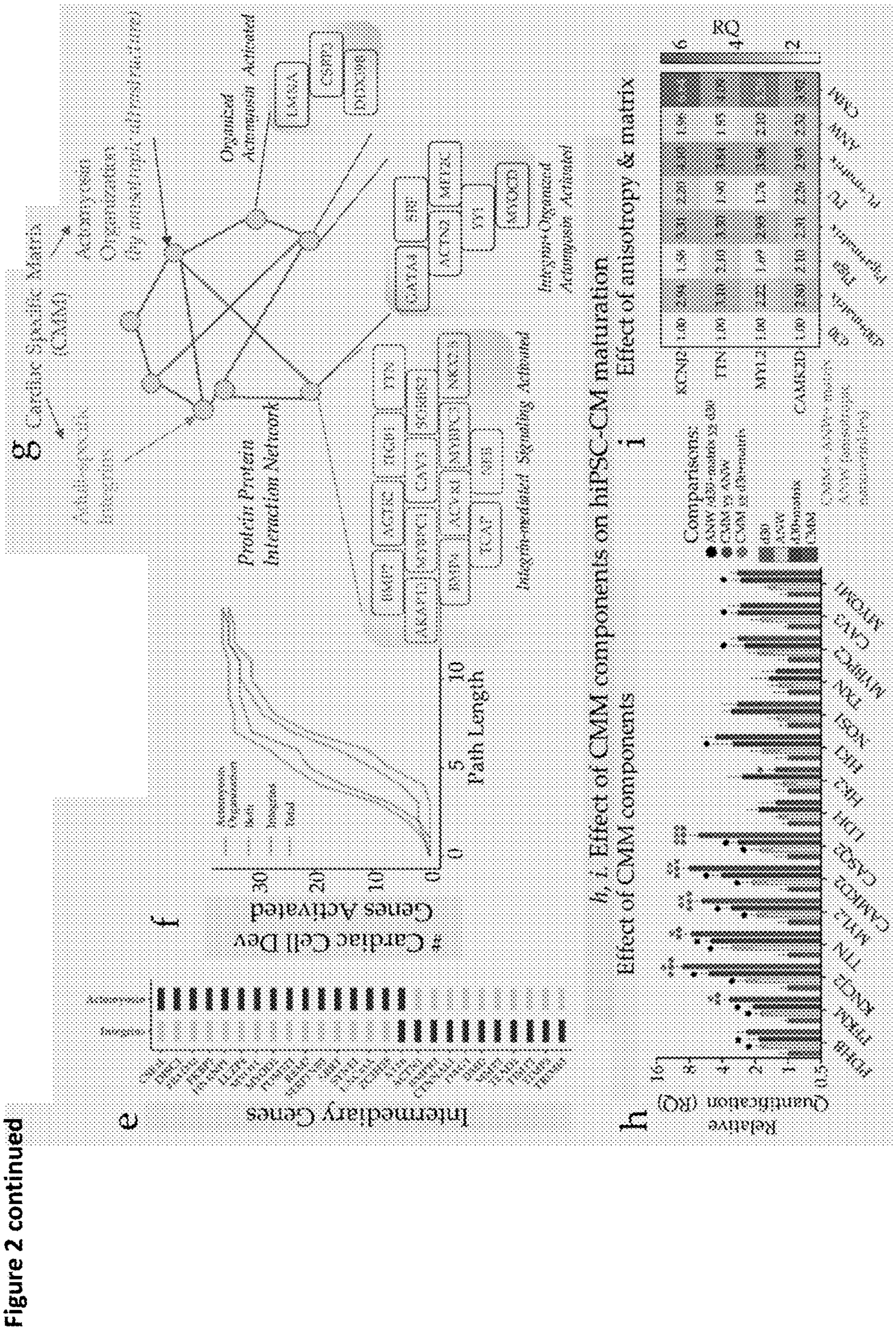

Tracing individual gene expression change along the stages of maturation (d30 to d60 to CMM to fetal to adult) confirmed the general trend of a transcriptomic cardiac maturation vector (FIG. 1*l, m*). Hive plots for cardiac development ontology showed that CMM resulted in accelerated upregulation of many genes within 30 days, similar to prolonged culture for 60 days (FIG. 2*a*-*b*). Upstream regulators predicted by Ingenuity Pathway Analysis (IPA) contained many transcriptional factors (TFs) related to cardiac development activated in CMM, as well as in developed heart, many activated in CMM even more than in prolonged d60 condition (FIG. 2*c*). These TFs included many SMADs, cardiac specific TFs MYOD1, MYOCD, MEF2C, and TBX5. The global persistence of genes suggested activation of cardiac development related transcriptional program that strengthens as cells change their state along the cardiac maturation vector.

Figure 12:
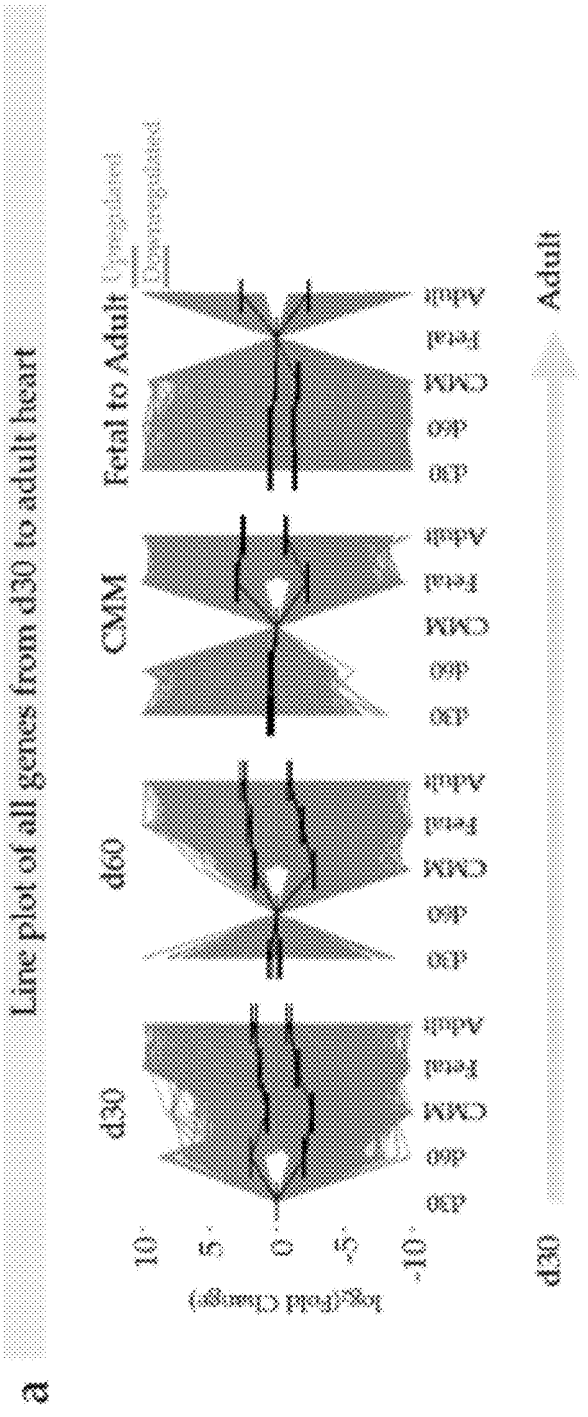
FIG. 12 shows MINI transcriptionally upregulates cardiac development genes and regulators, Related to FIG. 2. (a) Line plot of individual genes Log fold change (LFC) showing expression changes in each stage (d30, d60, CMM, fetal, and adult heart); Each panel shows only genes significantly differentially regulated between the subsequent stages of maturation. Black line represents the mean expression changes with error bars (SD). The data show that genes that are upregulated or downregulated at d30 are progressively increased/reduced in d60, CMM and fetal/adult heart showing a linear trend. Integrin mediated signaling and actomyosin assembly synergistically activate cardiac developmental program in hiPSC-CMs on CMM. (b) A subnetwork of protein-protein interactions relating the key integrins targeted in MINI and the up-regulated cardiac development genes. The network is generated by prioritizing up-regulated genes and nonpromiscuous connections to connect the adult heart specific integrins and all actomyosin organization genes, with both inputs equally weighted to cardiac development genes using a customized Prize Collecting Steiner Tree (PCST). (c) The list of intermediary genes connecting the 5 integrin and 5 actomyosin genes connecting the target cardiac genes with paths of length 5 or less, in a PCST constructed from multivalidated PPIs. The genes included in these paths starting from each source (integrins or actomyosin organization) are shown in the respective column. (d) The number of cardiac cell development genes activated or reached from the 5 integrins or 202 actomyosin organization genes, both sets equally weighted, shown on the y-axis against the maximal lengths of paths considered on the x-axis. The different lines are for the genes predicted to be activated by integrins, actomyosin organization genes, both activations (Both), or by either (Total). All analysis performed on the PCST constructed using the multivalidated PPIs.
Figure 12:
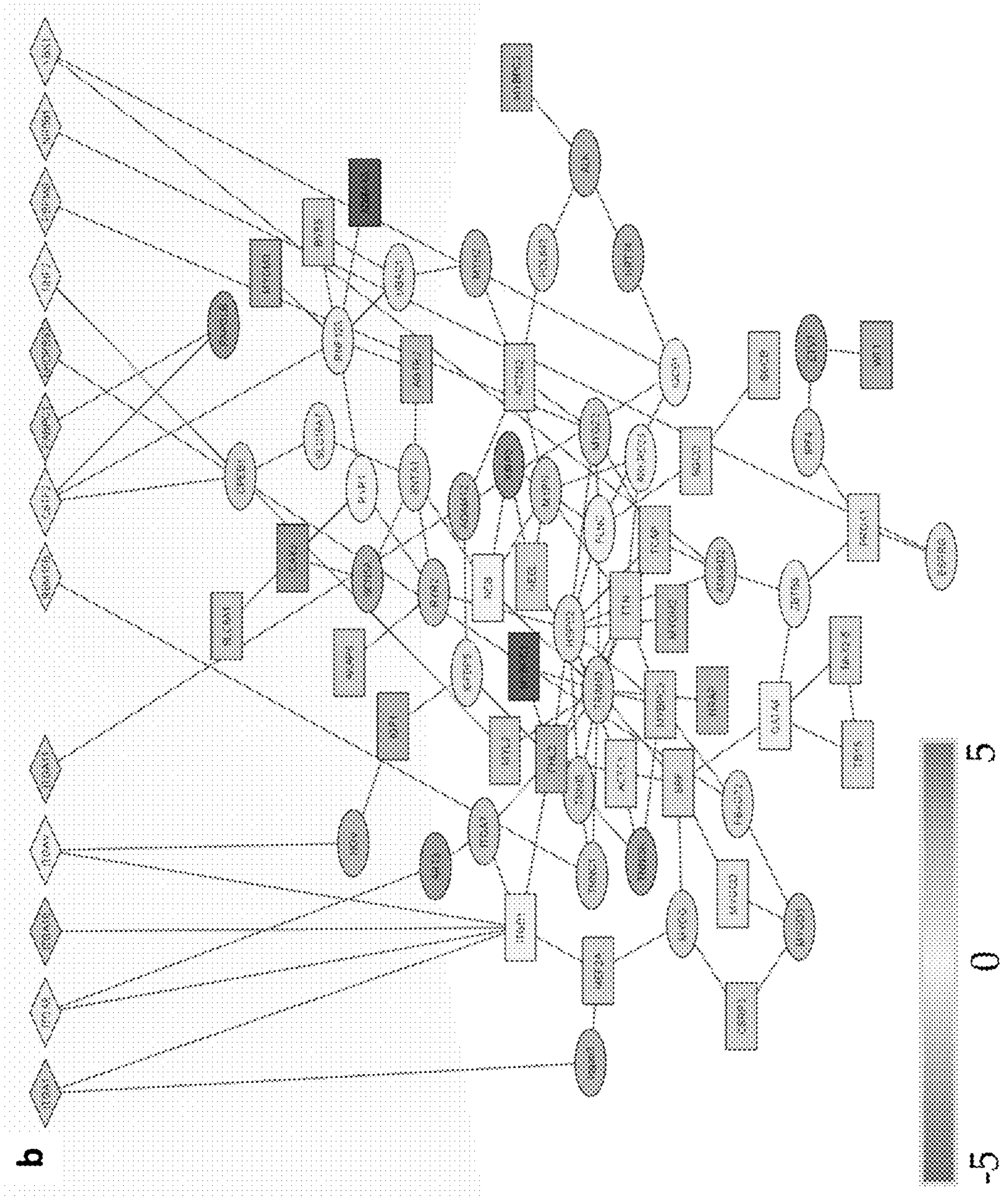
Figure 12:
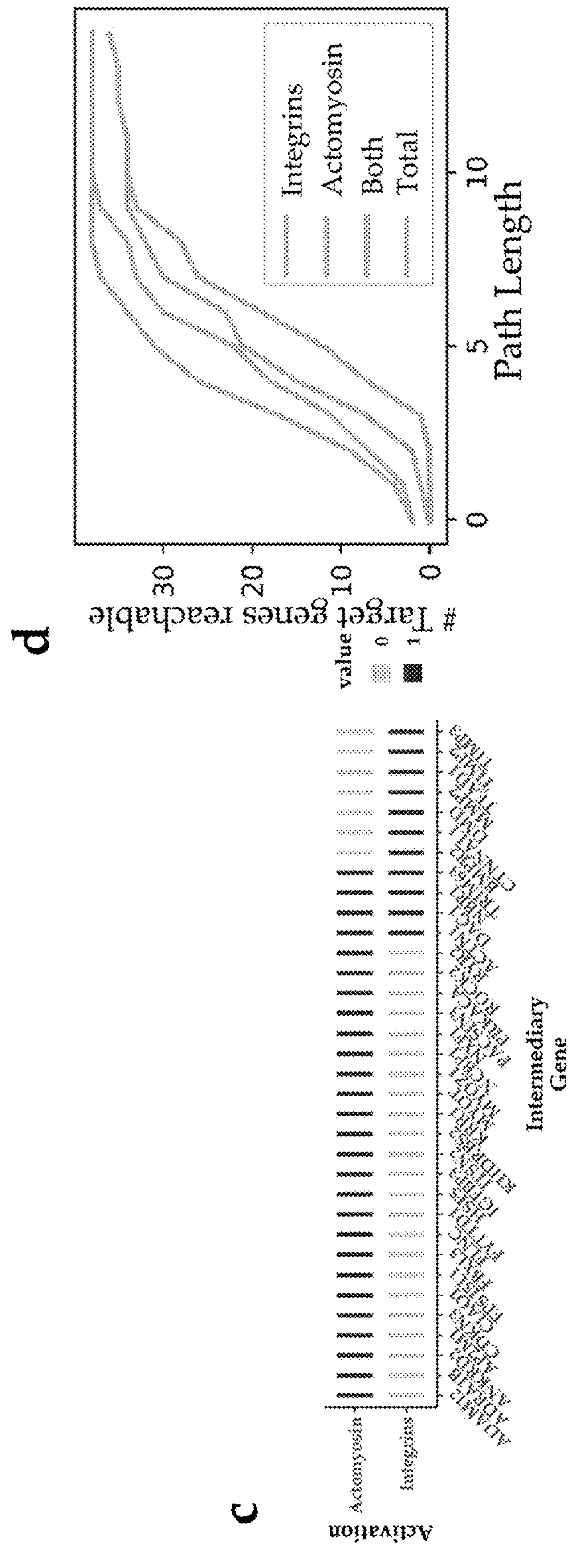

Example 5: CMM Induced Cardiac Maturation by Synergistic Combination of Cardiac-Specific Matrix Ligands, Ultrastructure, and Mechanics CMM is a composite platform, consisting of specific ligand chemistry, matrix mechanics and ultrastructure. To assess their relative contribution and identify potential signaling intermediaries involved, a novel networking analysis method was creasted using the Prize Collecting Steiner Tree formulation (see Example 1) (Akhmedov et al., 2017; Bienstock et al., 1993). The resultant subnetwork connecting CMM constituents (ligand chemistry, and mechanics) with the genes related to cardiac development through BIOGRID interactome (Stark et al., 2006). Genes in actomyosin organization ontology were used as a surrogate for those influenced by anisotropic matrix and physiological elasticity, while adult-heart specific integrins were used as the second input into the PPI network, prioritizing inclusion of genes differentially upregulated in CMM vs Control. A comprehensive network was generated connecting the 5 integrin genes in adult-heart, and top 5 genes (FIG. 2*d*), or weighted input of the whole actomyosin organization ontology (FIG. 12*b*). Both networks succinctly captured candidate intermediaries also mostly upregulated in CMM (FIG. 2*d*, 12*b*), including TNNI3, MYOD1, MYPN, MYH2, XIRP2, RYR1 and RYR2 (Friedman et al., 2018; Paige et al., 2015; Thompson et al., 1991; Uosaki et al., 2015) (FIG. 2*d*, 12*b*). Within a path length of 5, nearly exclusive subnetworks suggesting an additive effect of both inputs, with ATF6 as the common intermediary was found (FIG. 2*e*). With more gene inputs, a few more non-exclusive intermediaries (ACTN1, DAG1, NBR1, and TRIM63) was found, but subnetworks remained largely mutually exclusive (FIG. 12*c*). It was found that counting the number of gene targets reached for a given path length, either input synergistically reaching multiple target nodes in relatively short paths (FIG. 2*f*, 12(*d*), chiefly ACTN2, CAV3, GSK3A, MYBPC1/3, GATA4, MEF2C, MYOCD, and SRF (FIG. 2*g* and Table 4).

TABLE 4

The set of targets, i.e., cardiac development genes activated by the Integrins and actomyosin organization genes with path lengths of 5 or less in the PCST constructed from on multivalidated PPIs

| Reachable from Actomyosin | Reachable from Integrins | Reachable from Both |
|---|---|---|
| ACO1, ADRA1A, AKAP6, APOBEC3G, CDK1, DDX39B, IGF1, IREB2, KHDRBS1, KHDRBS3, LIN28A, LIN28B, MYL2, NCBP2, NIFK, NUDT21, RBM15, RBM15B, RBMX, RNPS1, SAMHD1, SGCD, SRSF1, SRSF6, WT1, YBX1, YTHDC1 | ACVR1, AGTR2, AKAP13, BMP2, BMP4, GATA4, ITGA1, ITGAV, MEF2C, MYOCD, NKX2-5 | ACTN2, CAV3, FHL2, GSK3A, ITGB1, MYBPC1, MYBPC3, NEB, SORBS2, SRF, TCAP, TTN |

Figure 13:
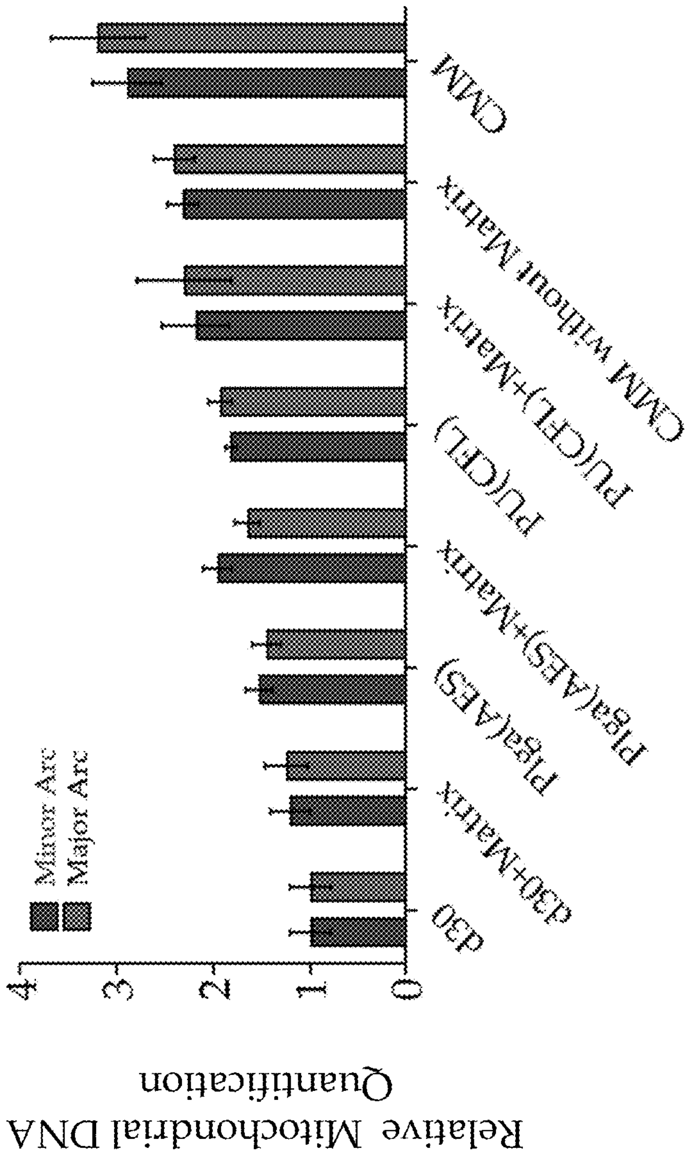
FIG. 13 shows CMM upregulates cardiac genes and mitochondrial DNA, Related to FIG. 2. Detail statistical analysis of qRT-PCR data (FIG. 2*i*). Coding shows statistically significant values following Anova test with Tukey correction (from FIG. 2*i*). Relative mitochondrial quantification on different surfaces with/without matrix shows matrix in combination with different technologies to produce anisotropic nanotopography increases mitochondrial numbers (Tables 5-7). MINI without matrix showed a significant increase in mitochondrial content than other nanotopographical substrates (aligned electrospun PLGA nanofibers, and capillary force lithography-based PU fibers). Sidak's test was performed to evaluate differences among each condition in combination with/without matrix.
Figure 14:
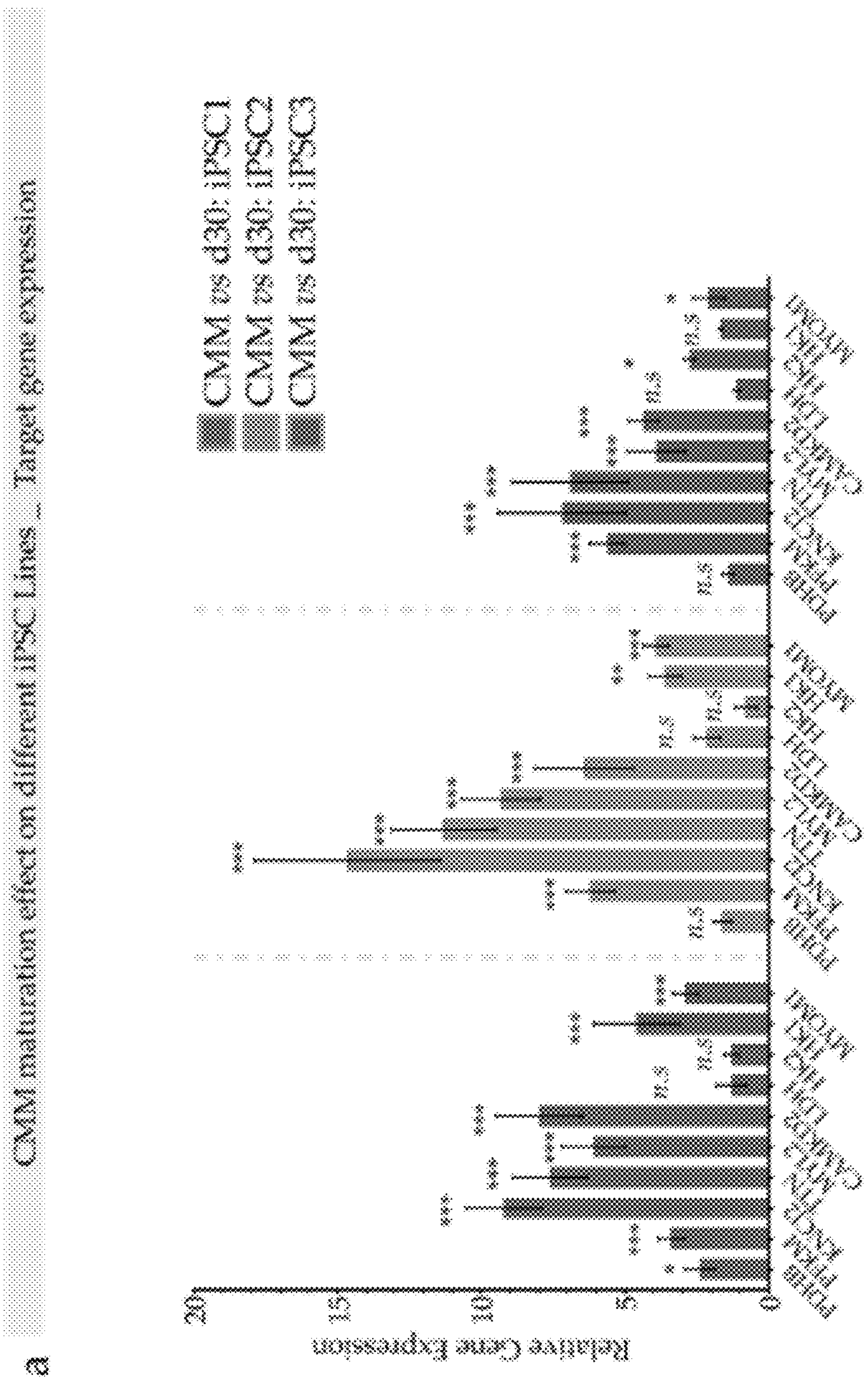
FIG. 14 shows maturation of iPSC-CM on CMM is cell line independent, Related to FIG. 2. (a-b) RT-PCR of cardiac maturation markers and mitchondiral DNA. (a) Targeted gene expression and (b) mitochondrial quantification from three different iPSCs lines on the CMM substrate when compared to their respective d30 samples demonstrate molecular cardiac maturation. Human iPSCs line 1 (WTC-11) was the line used for all the other studies in the manuscript while line 2 (HF-YK27) and line 3 (PBY4-48D) were used to test the molecular markers for cardiac differentiation. Statistical significance was calculated using Anova test with Tukey correction.
Figure 14:
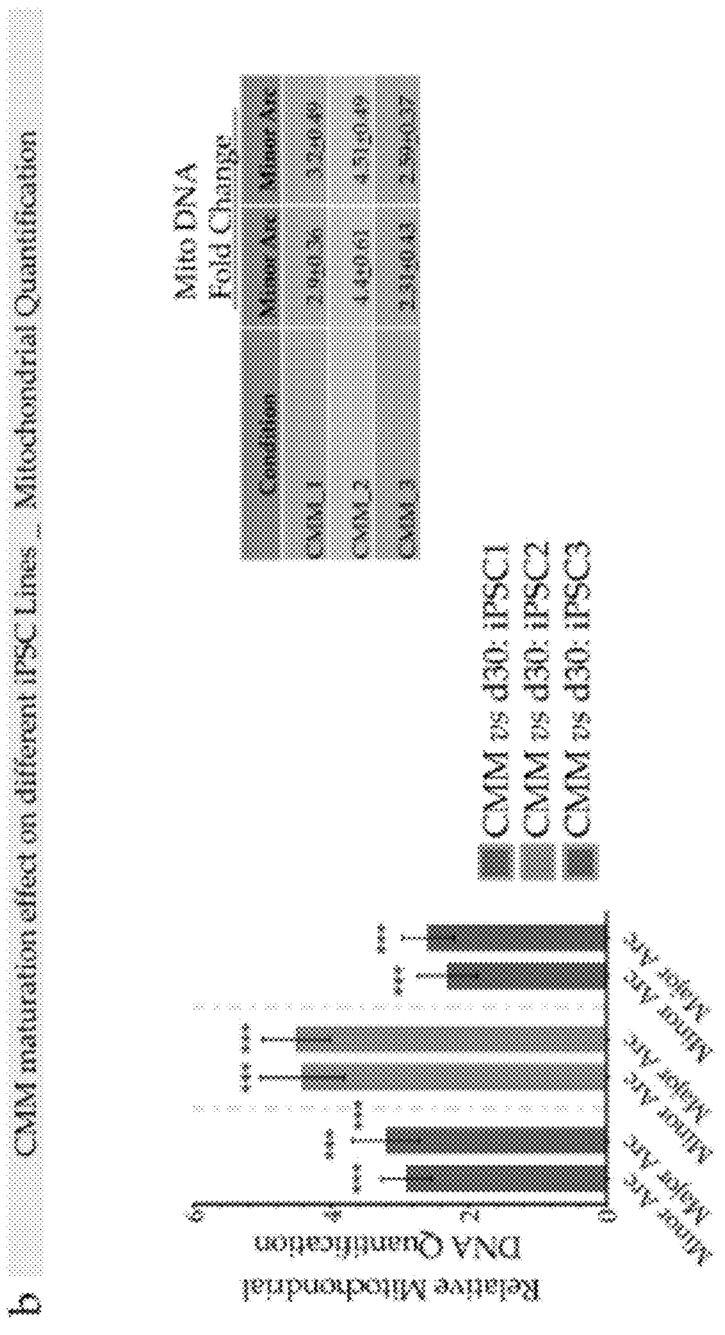

It was then experimentally tested the prediction of synergistic effect of individual components of CMM for cardiac transcripts, and mitochondrial maturation. Cells were placed on flat (d30), matrix conjugated (d30+matrix), anisotropic nanowrinkled (ANW) surfaces, and ANW surfaces conjugated with matrix (CMM) (FIG. 2*h*). RT-PCR analysis on a panel of key cardiac specific genes showed that ligands and ultrastructure had a synergistic effect on CMM (FIG. 2*h*). Culture on CMM showed increase in key metabolic, structural, and calcium/electrophysiological genes, including PDHB, PFKM, KCNJ2, TTN, MYL2, CAMK2D, CASQ2. The effect of alternative nanotextured substrates combined with cardiac specific matrix ligands was also tested. RT-PCR of key markers for cardiac maturation showed that CMM induced superior maturation than aligned electrospun PLGA, and aligned capillary force lithography (CFL) based PUA substrates (FIG. 2*i*, 13, Tables 5-7)(Carson et al., 2016; Choi et al., 2020; Kumar et al., 2020; Yu et al., 2014). Mitochondrial DNA quantification confirmed a similar trend on CMM vs anisotropic PLGA electrospun fibers, and CFL substrates (FIG. 13 and Tables 5-7). RT-PCR and mitochondrial DNA also demonstrated maturation of cardiomyocytes derived from other iPSC cell lines on CMM (FIG. 14*a*-*b*). Together with the PPI subnetwork analysis, these data showed that a mechano-chemical cues in CMM synergistically influenced cardiac development. It was then sought to characterize the cardiac-specific phenotypes of CMM matured cardiac constructs, positioning their structure, metabolism and function contextually to the adult-like hallmarks of cardiac behavior (Yang et al., 2014).

TABLE 5

| Statistics of qRT-PCR of genes with matrix and different anisotropic surfaces | | | | |
|---|---|---|---|---|
| | Adjusted pVal (Tukey's multicomparison) | | | |
| Condition | KCNJ2 | TTN | CAMK2D | MYL2 |
| d30 vs. d30 + matrix | <0.0001 | <0.0001 | <0.0001 | 0.0028 |
| d30 vs. Plga(AES) | 0.5641 | 0.0108 | 0.0108 | 0.3333 |
| d30 vs. Plga(AES) + matrix | <0.0001 | <0.0001 | 0.0009 | <0.0001 |
| d30 vs. PU(CFL) | 0.0035 | 0.0748 | 0.0017 | 0.2169 |
| d30 vs. PU(CFL) + matrix | <0.0001 | <0.0001 | <0.0001 | <0.0001 |
| d30 vs. CMM without matrix | 0.0439 | 0.1127 | 0.0008 | 0.0108 |
| d30 vs. CMM | <0.0001 | <0.0001 | <0.0001 | <0.0001 |
| d30 + matrix vs. Plga(AES) | 0.0005 | 0.0301 | 0.3149 | 0.6734 |
| d30 + matrix vs. Plga(AES) + matrix | 0.9304 | 0.9981 | 0.7548 | 0.2630 |
| d30 + matrix vs. PU(CFL) | 0.2470 | 0.0035 | 0.6520 | 0.8097 |
| d30 + matrix vs. PU(CFL) + matrix | 0.0056 | 0.2470 | 0.9997 | 0.0005 |
| d30 + matrix vs. CMM without matrix | 0.0364 | 0.0019 | 0.7738 | >0.9999 |
| d30 + matrix vs. CMM | <0.0001 | 0.0331 | 0.0296 | <0.0001 |
| Plga(AES) vs. Plga(AES) + matrix | <0.0001 | 0.0035 | 0.9974 | 0.0017 |
| Plga(AES) vs. PU(CFL) | 0.4761 | 0.9981 | 0.9995 | >0.9999 |
| Plga(AES) vs. PU(CFL) + matrix | <0.0001 | <0.0001 | 0.1127 | <0.0001 |
| Plga(AES) vs. CMM without matrix | 0.9205 | 0.9922 | 0.9965 | 0.8855 |
| Plga(AES) vs. CMM | <0.0001 | <0.0001 | <0.0001 | <0.0001 |
| Plga(AES) + matrix vs. PU(CFL) | 0.0097 | 0.0003 | >0.9999 | 0.0039 |
| Plga(AES) + matrix vs. PU(CFL) + matrix | 0.1765 | 0.6520 | 0.4333 | 0.4545 |
| Plga(AES) + matrix vs. CMM without matrix | 0.0005 | 0.0001 | >0.9999 | 0.1127 |
| Plga(AES) + matrix vs. CMM | <0.0001 | 0.1765 | 0.0002 | <0.0001 |
| PU(CFL) vs. PU(CFL) + matrix | <0.0001 | <0.0001 | 0.3333 | <0.0001 |
| PU(CFL) vs. CMM without matrix | 0.9940 | >0.9999 | >0.9999 | 0.9551 |
| PU(CFL) vs. CMM | <0.0001 | <0.0001 | <0.0001 | <0.0001 |
| PU(CFL) + matrix vs. CMM without matrix | <0.0001 | <0.0001 | 0.4545 | <0.0001 |
| PU(CFL) + matrix vs. CMM | <0.0001 | 0.9922 | 0.0979 | <0.0001 |
| CMM without matrix vs. CMM | <0.0001 | <0.0001 | 0.0002 | <0.0001 |

TABLE 6

| Mito DNA Fold Change | | |
|---|---|---|
| Condition | Minor Arc | Minor Arc |
| d30 | 1 ± 0.212 | 1 ± 0.19 |
| d30 + Matrix | 1.21 ± 0.2 | 1.25 ± 0.23 |
| Plga(AES) | 1.53 ± 0.14 | 1.4 ± 0.15 |
| Plga(AES) + Matrix | 1.96 ± 0.15 | 1.65 ± 0.13 |
| PU(CFL) | 1.82 ± 0.09 | 1.93 ± 0.12 |
| PU(CFL) + Matrix | 2.19 ± 0.35 | 2.31 ± 0.49 |
| CMM without Matrix | 2.32 ± 0.16 | 2.41 ± 0.21 |
| CMM | 2.9 ± 0.36 | 3.2 ± 0.49 |

TABLE 7

| Šídák's multiple comparisons test | | |
|---|---|---|
| Šídák's multiple comparisons test | Summary | pVal_Adj |
| MajorArc | | |
| d30 vs. d30 + matrix | ns | 0.9466 |
| d30 vs. Plga(AES) | ns | 0.0956 |
| d30 vs. Plga(AES) + Matrix | ** | 0.0012 |
| d30 vs. PU(CFL) | **** | <0.0001 |
| d30 vs. PU(CFL) + Matrix | **** | <0.0001 |
| d30 vs. CMM without Matrix | **** | <0.0001 |
| d30 vs. CMM | **** | <0.0001 |
| d30 + matrix vs. Plga(AES) | ns | 0.9969 |
| d30 + matrix vs. Plga(AES) + Matrix | ns | 0.2288 |
| d30 + matrix vs. PU(CFL) | *** | 0.0006 |
| d30 + matrix vs. PU(CFL) + Matrix | **** | <0.0001 |
| d30 + matrix vs. CMM without Matrix | **** | <0.0001 |
| d30 + matrix vs. CMM | **** | <0.0001 |
| Plga(AES) vs. Plga(AES) + Matrix | ns | 0.9969 |
| Plga(AES) vs. PU(CFL) | ns | 0.0535 |
| Plga(AES) vs. PU(CFL) + Matrix | **** | <0.0001 |
| Plga(AES) vs. CMM without Matrix | **** | <0.0001 |
| Plga(AES) vs. CMM | **** | <0.0001 |
| Plga(AES) + Matrix vs. PU(CFL) | ns | 0.8499 |
| Plga(AES) + Matrix vs. PU(CFL) + Matrix | *** | 0.0009 |
| Plga(AES) + Matrix vs. CMM without Matrix | **** | <0.0001 |
| Plga(AES) + Matrix vs. CMM | **** | <0.0001 |
| PU(CFL) vs. PU(CFL) + Matrix | ns | 0.3109 |
| PU(CFL) vs. CMM without Matrix | ns | 0.0535 |
| PU(CFL) vs. CMM | **** | <0.0001 |
| PU(CFL) + Matrix vs. CMM without Matrix | ns | >0.9999 |
| PU(CFL)+Matrix vs. CMM | **** | <0.0001 |
| CMM without Matrix vs. CMM | **** | <0.0001 |
| MinorArc | | |
| d30 vs. d30 + matrix | ns | 0.9936 |
| d30 vs. Plga(AES) | * | 0.0189 |
| d30 vs. Plga(AES) + Matrix | **** | <0.0001 |
| d30 vs. PU(CFL) | **** | <0.0001 |
| d30 vs. PU(CFL) + Matrix | **** | <0.0001 |
| d30 vs. CMM without Matrix | **** | <0.0001 |
| d30 vs. CMM | **** | <0.0001 |
| d30 + matrix vs. Plga(AES) | ns | 0.6405 |
| d30 + matrix vs. Plga(AES) + Matrix | **** | <0.0001 |
| d30 + matrix vs. PU(CFL) | ** | 0.0031 |
| d30 + matrix vs. PU(CFL) + Matrix | **** | <0.0001 |
| d30 + matrix vs. CMM without Matrix | **** | <0.0001 |
| d30 + matrix vs. CMM | **** | <0.0001 |
| Plga(AES) vs. Plga(AES) + Matrix | ns | 0.1377 |
| Plga(AES) vs. PU(CFL) | ns | 0.8044 |
| Plga(AES) vs. PU(CFL) + Matrix | *** | 0.0009 |
| Plga(AES) vs. CMM without Matrix | **** | <0.0001 |

TABLE 7-continued

| Šidák's multiple comparisons test | | |
|---|---|---|
| Šidák's multiple comparisons test | Summary | pVal_Adj |
| Plga(AES) vs. CMM | **** | <0.0001 |
| Plga(AES) + Matrix vs. PU(CFL) | ns | >0.9999 |
| Plga(AES) + Matrix vs. PU(CFL) + Matrix | ns | 0.9791 |
| Plga(AES) + Matrix vs. CMM without Matrix | ns | 0.4099 |
| Plga(AES) + Matrix vs. CMM | **** | <0.0001 |
| PU(CFL) vs. PU(CFL) + Matrix | ns | 0.3584 |
| PU(CFL) vs. CMM without Matrix | * | 0.0356 |
| PU(CFL) vs. CMM | **** | <0.0001 |
| PU(CFL) + Matrix vs. CMM without Matrix | ns | >0.9999 |
| PU(CFL) + Matrix vs. CMM | *** | 0.0003 |
| CMM without Matrix vs. CMM | ** | 0.0062 |

Example 6: Differentiated Cardiomyocytes Structurally Mature on CMM

Figure 15:
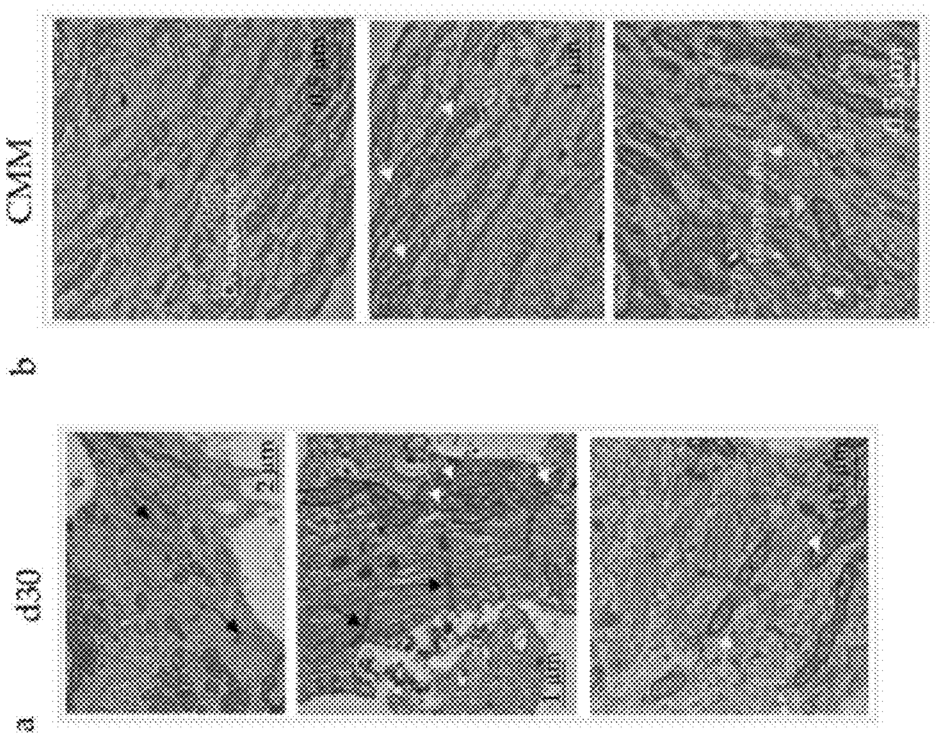
FIG. 15 shows transmission electron microscopy, Related to FIG. 3. Fused elongated and innumerable mitochondria on CMM (b) compared to d30 (a). Pointers indicate desmosomes, sr (sarcoplasmic reticulum), white pointers along long axis of mitochondria and black are perpendicular to the myofibrils Z-band in d30.
Figure 16:
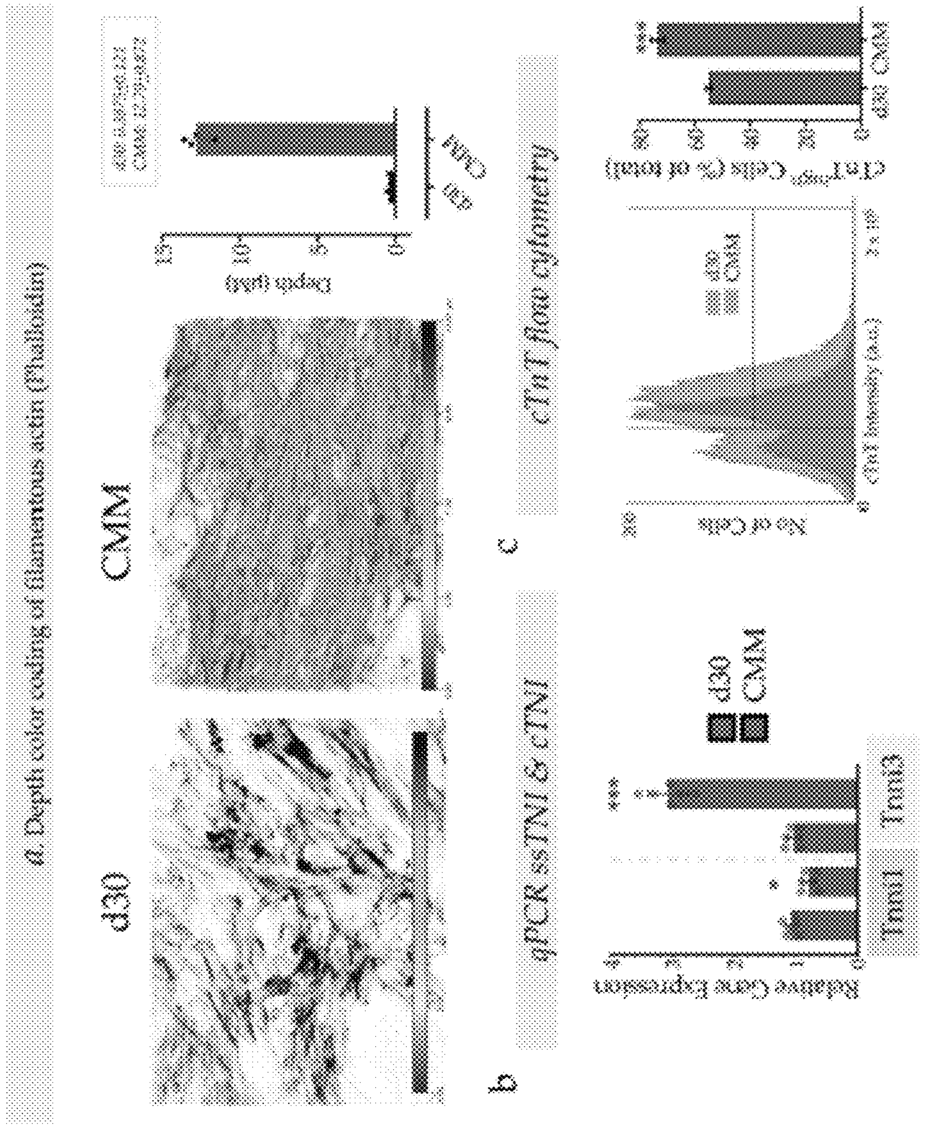
FIG. 16 shows structural changes on CMM, Related to FIG. 3. (a) Depth color coded z-stack of FActin (Phalloidin) immunostained samples viewed in a xy plane on a 2 photon microscope. The filamentous actin strands depth coding indicates F-actin bundles traversing 10 uM distance in on CMM (14 uM depth) while d30 (8 uM depth) have F-actin within 1 uM depth. Cells on d30 do not have a z-axis profile due to cell spreading on a flat surface with no 3D profile. Analysis of depth scaling shows that cells on CMM shows ~13 μM z-axis profile while cells on flat culture (d30) shows only ~0.5 μM of depth indicating flat morphology of cells in d30 condition. Color coding of heat intensity bar represent the z-axis depth (n=4). (b) qRT-PCR of slow skeletal type troponin I1 (Tnni1, ssTNI) and cardiac troponin I (TnniI3) genes show significant upregulation (3 fold) of cardiac Tnni3 and downregulation (0.7 fold) of Tnni1 on CMA/1. Statistical significance was calculated using Anova with Dunnett's test and reported as $p<0.05$(*) & $p<0.01$ (*). (c-d) Flowcytometry data of sarcomeric proteins. (c) Over 70% of cells on CMM express significantly higher cTnT levels per cell (n=4). (d) My12 intensity plot of flowcytometry data. Bar plots are presented as mean with +SD. Statistical significance is defined as $p<0.001$(*). (e-f) Confocal image of cells on CMM with MYL2 and α-Actinin, with average intensity profiles/average peak to peak distance along individual sarcomeric strips indicated in (e). (g-h) Confocal image of cells on CMM with MYL2 and cardiac troponin, along with the average intensity profile along sarcomeres in (g).
Figure 16:
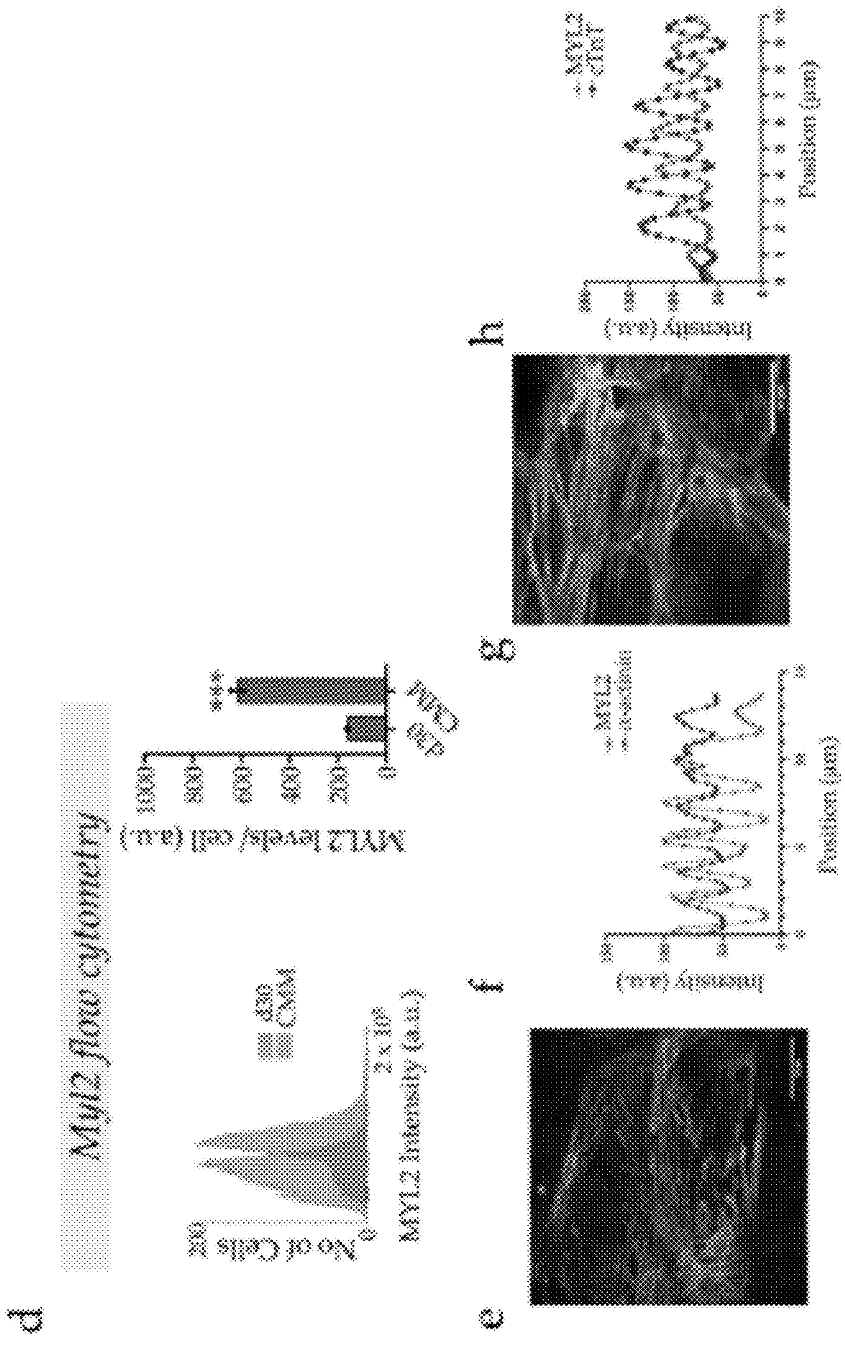
Figure 17:
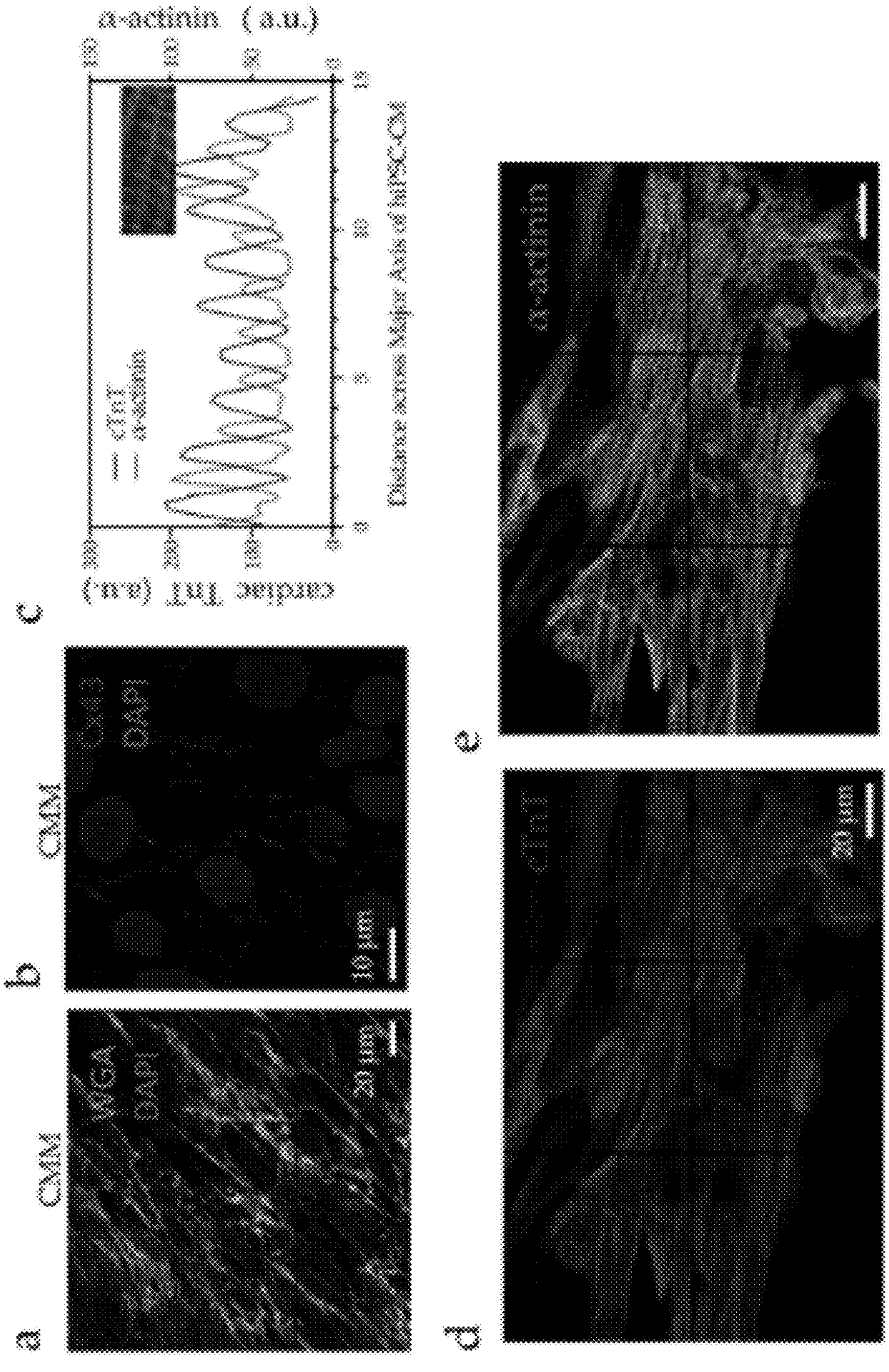
FIG. 17 shows structural changes on CMM, Related to FIG. 3. (a-b) Airyscan imaging of cells on CMM stained with WGA, or CX43; nuclei stained with DAPI; images are stitched to create a montage. (c) Quantification of Airyscan imaging of cells on CMM stained with cardiac troponin T and a-actinin from FIG. 3*n*. (d-e) Airyscan imaging of cells on CMM stained with cardiac troponin T (d) and α-actinin (e). Merge figure shown in FIG. 3*n*. (f-g) Beating duration and frequency calculated from the velocity profiles (FIG. 3*o*). Significance was calculated using oneway ANOVA with Tukey's HSD. (h-l) Nanowrinkled Incorporated Traction Force Microscopy. (h) Images of fluorescent beads incorporated in the NanoTFM substrate. (i) Individual cell spreading (evaluated using ventricular cardiac fibroblast) along the anisotropic nanowrinkled TFM substrate. (j) Waveform showing beads displacement relative to their location in the nanowrinkled TFM substrate when plated cardiac cells are paced at 0.5 Hz. (k-l) Strain energy and contractility levels on CMM and d30 cells when paced from 0.5 Hz to 1.5 Hz. Significance was calculated using two-way ANOVA with Šidak correction. Data is represented as mean+SD, and statistical significance is defined as p<0.001 (***).
Figure 17:
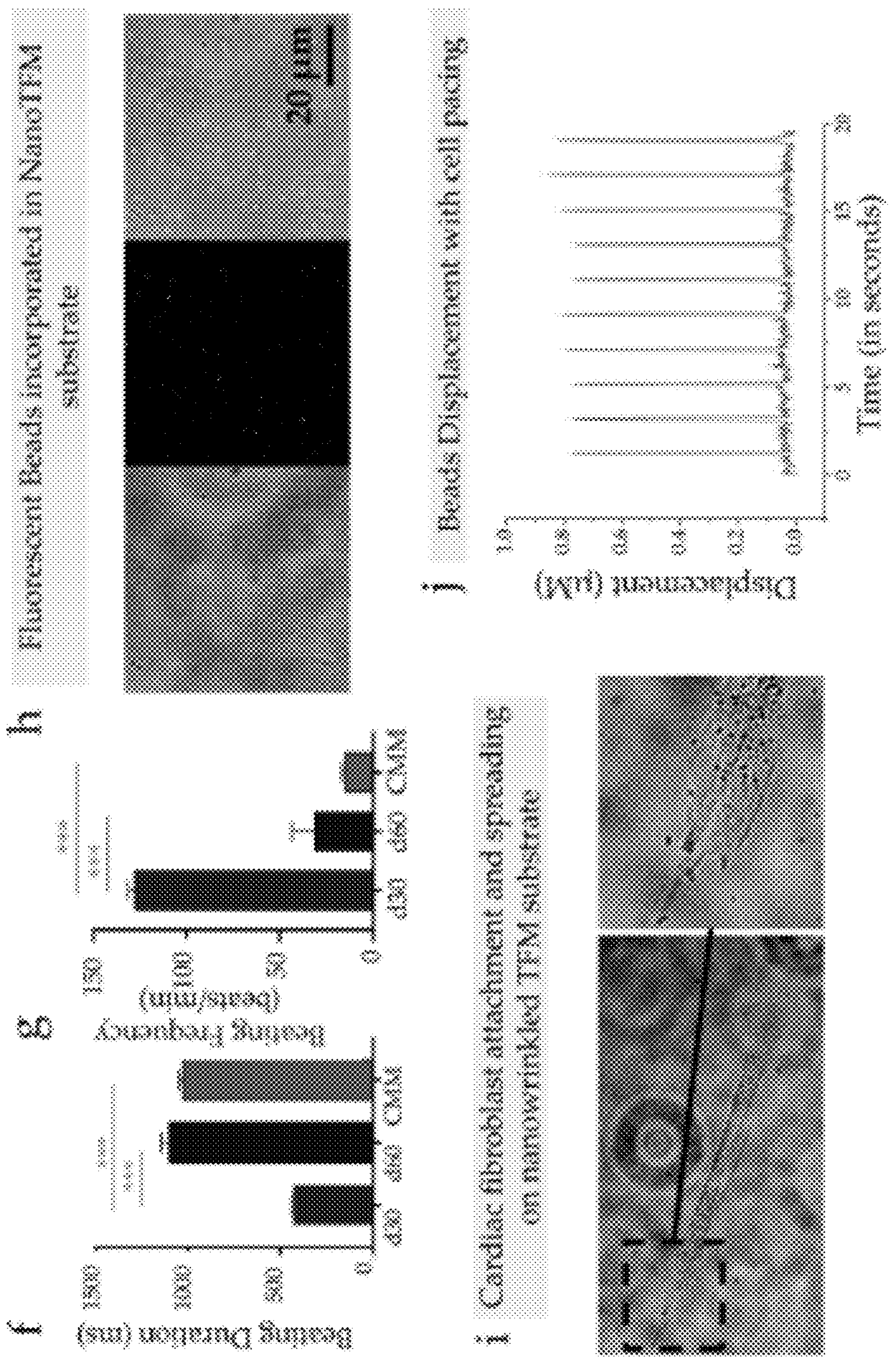
Figure 17:
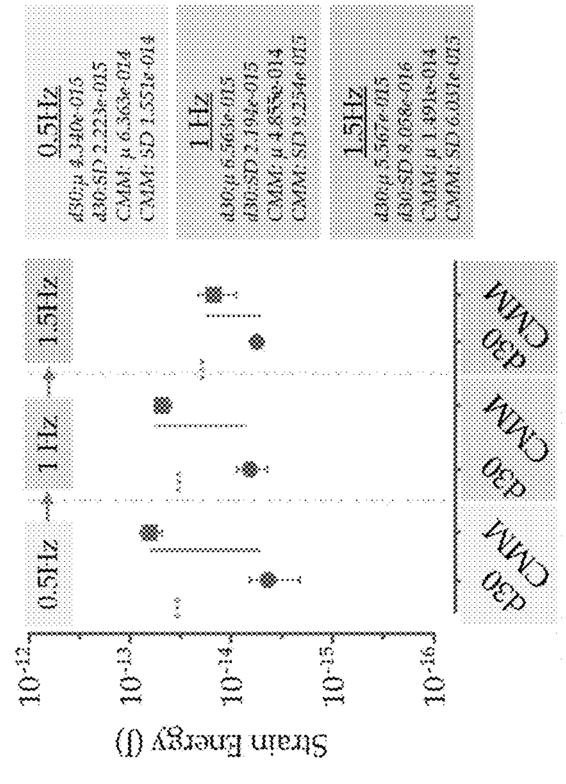
Figure 17:
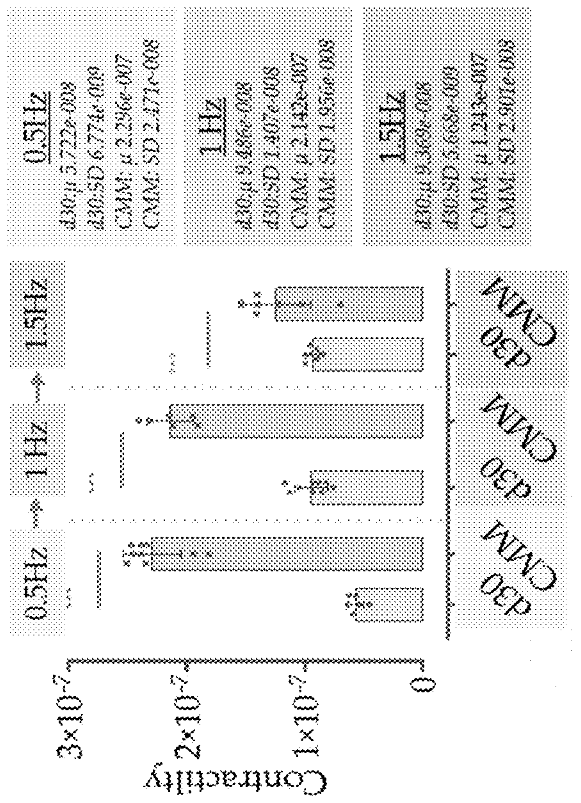

It was first characterized whether CMM induced changes in gene expression resulted in accompanying maturation in the structural and mechanical characteristics. Focusing on ontologies related to cardiac structure, it was found that CMM caused increase in gene expression even more than d60 (FIG. 3*a*). Top genes with correlated increase on CMM, and developed heart showed higher expression on CMM compared to d30, and even d60 (FIG. 3*b*). Transmission Electron Microscopy (TEM) showed that cells on CMM contained structurally organized and aligned arrangement of multiple sarcomeres bundle parallel to each other, and many enlarged and elongated mitochondria (FIG. 3*c*, 15*a-b*). Confocal microscopy revealed highly bundled and directionally aligned F-actin strands (FIG. 3*d-f*, 16*a*), with higher z-axis depth, indicating more voluminous microfilamentous architecture on CMM vs d30 (FIG. 16*a*). Immunostaining for α-actinin and Troponin I showed aligned myofibrils in cells on CMM vs d30 (FIG. 3*g*). Cardiac troponins form key structural components of muscle cell sarcomeric architecture and determine the maturation of iPSC-CMs (Bedada et al., 2016). RT-PCR showed significant upregulation of cardiac troponin isoform (Tnni3) and downregulation of slow skeletal isoform of Tnni1 on CMM (FIG. 16*b*). Flow cytometry distribution of cardiac Troponin T (cTnT) showed higher cTnT levels per cell (FIG. 3*h*, 16*c*), as well as enrichment of a $cTnT^{high}$ subpopulation (all cells were $cTnr^{+ve}$) (FIG. 16*c*), a trend observed for another key sarcomeric component, myosin light chain-2 (FIG. 3*i*, 16*d*). Immunoblot confirmed significantly higher levels of cTnT and cTnI on CMM vs d30 (FIG. 3*j-k*). As cardiomyocytes mature, relative abundance of isoform for myosin light chain MYL2 increases vs MYL7, a useful marker for a more developed state(Guo and Pu, 2020). Immunoblot showed a clear increase in relative abundance of MYL2 vs MYL7 isoforms in CMM vs control (FIG. 3*l-m*). Confocal imaging for MYL2 with α-actinin showed non-overlapping abundance on sarcomeres, with well separated bands (~1.8 μm) observed on CMM (FIG. 16*e-h*) (Lundy et al., 2013). Furthermore, airyscan imaging showed extensive overlapping strands stained for WGA (wheat germ agglutinin) (FIG. 17*a* shows 3D arrangement of lectin). Connexin 43 stained gap junctions also showed the classic punctate structures between cells, as well as organized series of intercellular junctions (FIG. 17*b*). Airyscan also showed cTnT and α-actinin distributed in adjacent locales within the sarcomeres with staggered expression patterns, indicating high degree of sarcomeric maturation/myofibrillar bundles in cells on CMM (FIG. 3*n*, 17*c-e*). Airyscan also confirmed the sarcomere length to be ~1.83±0.14 μm on matured cardiomyocytes on CMM (FIG. 17*c*).

Example 7: CMM Enhances Mechanical Maturation and Force Generation Capability of Differentiated Cardiomyocytes Cardiomyocytes are contractile cells, capable of force generation upon electrical stimulation. Increased structural maturation and high mitochondrial content in hiPSC-CMs on CMM suggested increased capability to produce contractile force. Particle image velocimetry on time-lapsed images of cells revealed contraction velocity vectors being randomly aligned on control substrate, while being more sustained and highly directional on CMM (FIG. 3*o*). Duration of beats on CMM was twice as long as on d30, while spontaneous beating was significantly reduced (FIG. 3*o*, 17*f-g*). To directly quantify the force generating capacity of cells, traction force microscopy (TFM) on anisotropic nanowrinkled substrates was augmented by embedding fluorescent beads below the nanowrinkles (FIG. 3*p-q*, 17*h*) (Knoll et al., 2014). TFM measures traction forces applied by a cell to the substratum via integrins tethered to the matrix and the force generating actomyosin assembly within. However, because cells are unloaded, the direct relation between traction force and contractile force may break down in very high pacing rates. TFM offers advantages beyond its subcellular resolution, as it can be combined with many microscopy compatible probes, to elicit direct relationship between force generation, and cell signaling or metabolic activity. Nano-TFM were placed with cultured cells in a pacing chamber, measuring their contractility and strain energy upon external pacing compared to d30. hiPSC-CMs on CMM had many folds increase in strain energy (FIG. 3*r-s*, 17*k*), and directional contractile force generation (FIG. 3*t*, 17*l*). High temporal resolution imaging confirmed mechanical contraction coupled to pacing (FIG. 17*j*). Overall, the data showed increased structural maturation on CMM accompanied by markedly higher force generating capability.

Example 8: CMM Exhibits Hallmarks of Adult-Like Metabolism

Cardiac tissue is highly metabolically active, dependent on mitochondrial oxidative respiration(Lopaschuk and Jaswal, 2010), with a high plasticity in substrate utilization, essential to rapidly generate ATP, which is limiting; ~10 mM lasting for a few contractions (Ingwall, 2009; Stanley et al., 2005). Transcriptomic data showed that hiPSC-CMs on CMM follow a more adult cardiac metabolic program, with increased expression of key transcripts in electron transport chain (ETC), FAO and OxPhos (FIG. 4*a*, 11 and Table 2-3). To evaluate the metabolic signature of cells on CMM, a comprehensive investigation of energetics was performed to characterize cellular and mitochondrial metabolism in both intact cells (for OxPhos and glycolysis) and permeabilized cells (for ETC activity and FAO). It was found that cells on CMM demonstrate significantly higher oxygen consumption rate (OCR) in comparison to the d30 (FIG. 4*b*). Compared to d30, cells on CMM exhibited higher OCR in intact cells at baseline from 81 pMol/min to 151 pMol/min, coupled respiration (oligomycin sensitive respiration) from 65 pMol/min to 141 pMol/min, and uncoupling capacity (FCCP) from 140 pMol/min to 425 pMol/min, indicating significantly higher OxPhos capacity (FIG. 4*b*). Not observed were significant differences in basal glycolysis levels (ECAR) in cells on CMM vs d30 (FIG. 4*c*). Then investigated was the maturation of mitochondrial energetics by measuring complex I & II of ETC and FAO in permeabilized cells (FIG. 4*d-e*). Activity of Complex I/II of ETC was measured at basal rates/State-4 (substrate only) using 5 mM Glutamate/Malate & 5 mM Succinate respectively, and active/State-3 respiration was measured with the addition of 4 mM Adp. An increase was observed in both state-4 and state-3 ETC activity in cells cultured on CMM, indicating higher mitochondrial ETC activity (FIG. 4*d*). Using 200 mM Palmitoyl-CoA Carnitine, an increased FAO in cells on CMM vs control was observed (FIG. 4*e*). The 2D nature of CMM facilitated measurement on permeabilized cells, necessary to directly measure ETC chain activity and substrate utilization.

Dependence on OxPhos and a high rate of ATP generation result in a high burden of reactive oxygen species, which adult-like cardiac cells can scavenge by maintaining 100 fold higher reduced glutathione (GSH) than the oxidized species (oxidized GSH, GSSG and mixed disulphide, GSSR) (Burgoyne et al., 2012; Santos et al., 2011) (Aquilano et al., 2014). Using a pulse of 1 mM-hydrogen peroxide ($H_2O_2$) in Tyrode buffer, the recovery of oxidized glutathione pool of hiPSC-CMs was evaluated using cytoplasmic Grx1-roGFP2 probe (Gutscher et al., 2008; Meyer and Dick, 2010). Grx1-roGFP2 signal intensity was normalized by respective addition of diamide, and Dithiothreitol (DTT) for max and min signal(Meyer and Dick, 2010). It was found that stable Grx1-roGFP2 signal (400 nm/485 nm ratio) at 60 seconds in all the conditions before calibration, and found that cells on CMM showed consistently lower Grx1-roGFP2 ratio (400 nm/485 nm) of 0.423±0.092, indicating rapid recovery of glutathione pool compared to cells on d30 cells (0.7163±0.08) (FIG. 4*f-g*). These results show metabolic maturation with higher OxPhos and improved ROS scavenging capability in CMM condition. The metabolic switch was also accompanied by reduced abundance of Pyruvate Dehydrogenase Kinase (PDK1) and platelet isoform of phosphofructokinase (PFKP), key glycolytic enzymes isoforms that are responsible for aerobic glycolysis, highly expressed in proliferative/glycolytic cells including stem cells(Lunt and Vander Heiden, 2011; Tanner et al., 2018) (FIG. 4*h-i*). There was no detectable difference in fatty acid synthase (FAS) levels, but abundance of acetyl-CoA synthetase (AceCS1), an enzyme regulating fatty acid/lipid biosynthesis (Schwer and Verdin, 2008) increased (FIG. 4*h-i*).

Example 9: Matured and Increased Mitochondria in hiPSC-CMs on CMM

Figure 5:
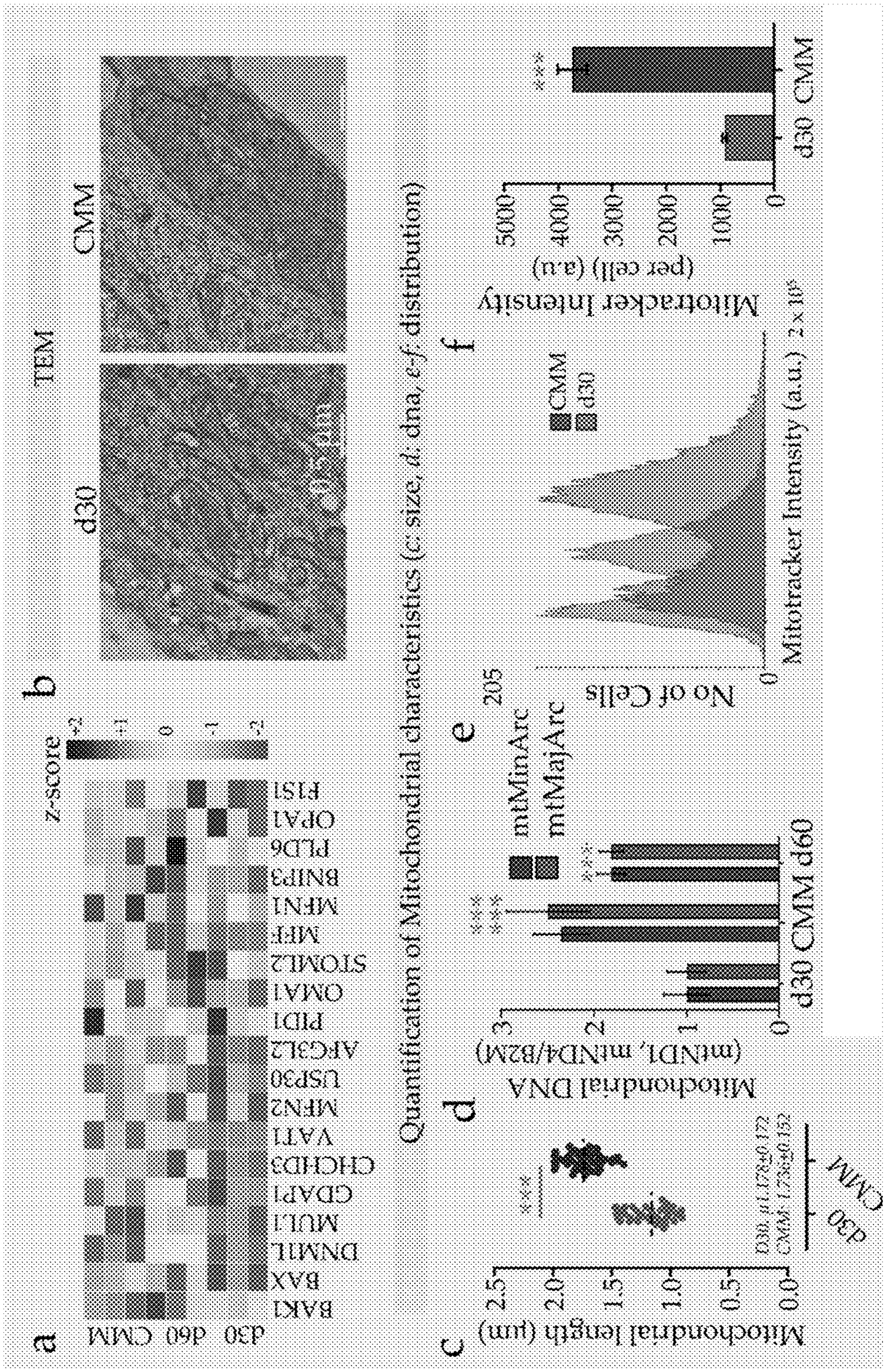
FIG. 5 shows increase in mitochondrial number and ETC subunits abundance on CMM. (a) Heatmap showing Z-scores of genes involved in mitochondrial dynamics (fusion). (b) TEM shows fused elongated mitochondria on CMM. Gj: gap junctions, D: desmosomes, sr: sarcoplasmic reticulum, m: mitochondria. (c) Mitochondrial length estimated from longitudinal TEM sections. (d) Mitochondrial DNA RT-PCR. Black stars: CMM vs d30, stars: CMM vs d60. (e-g) Flow cytometry analysis of Mitotracker Green indicate >3fold increase mitochondrial content on CMM (f), greater percentage of cells showing high mitochondrial numbers (g). (h-i) Immunoblot of ETC subunits (with relative quantification to GAPDH).
Figure 5:
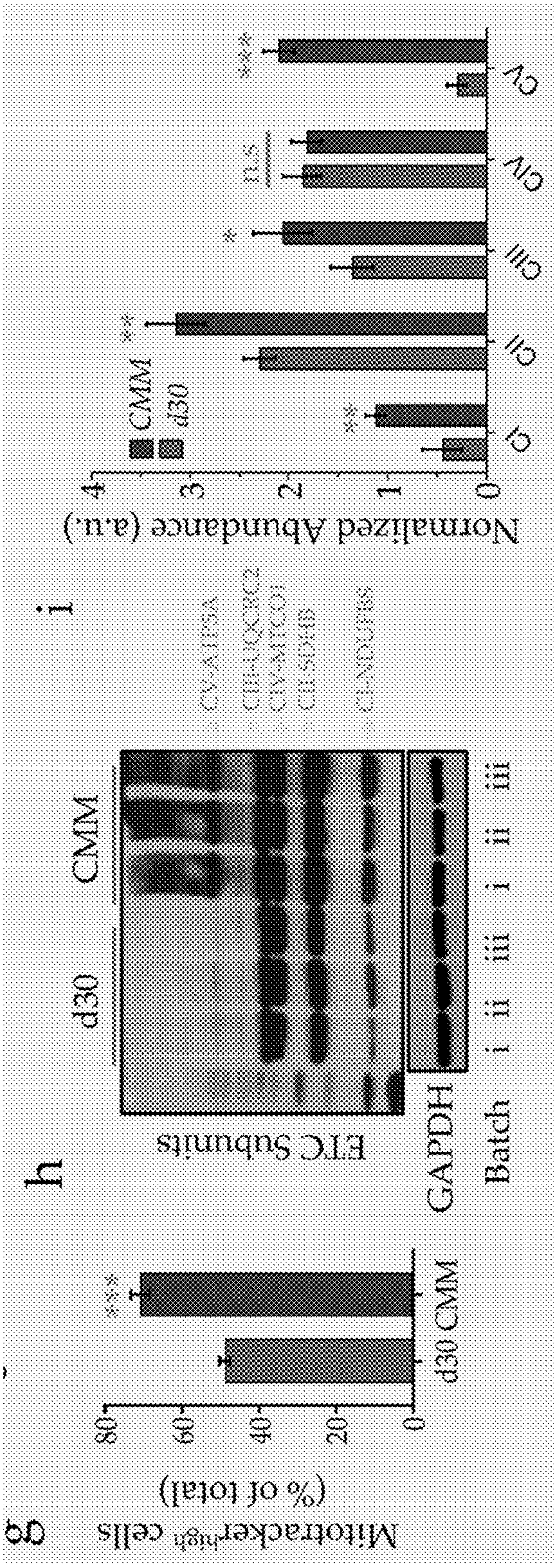
Figure 18:
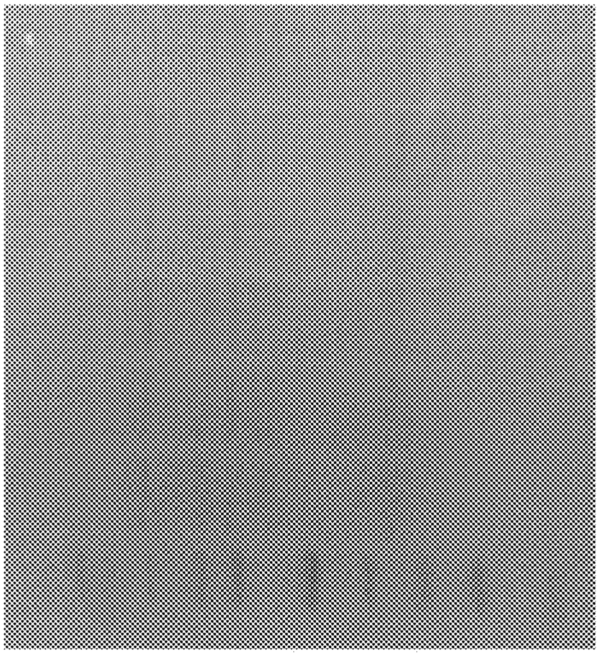
FIG. 18 shows ponceau Staining of ETC immunoblot membrane, Related to FIG. 5. Electron transport chain maturation on CMM supporting data. Ponceau S staining showing equal protein loading on the PVDF membrane used for ETC subunits immunoblots.
Figure 19:
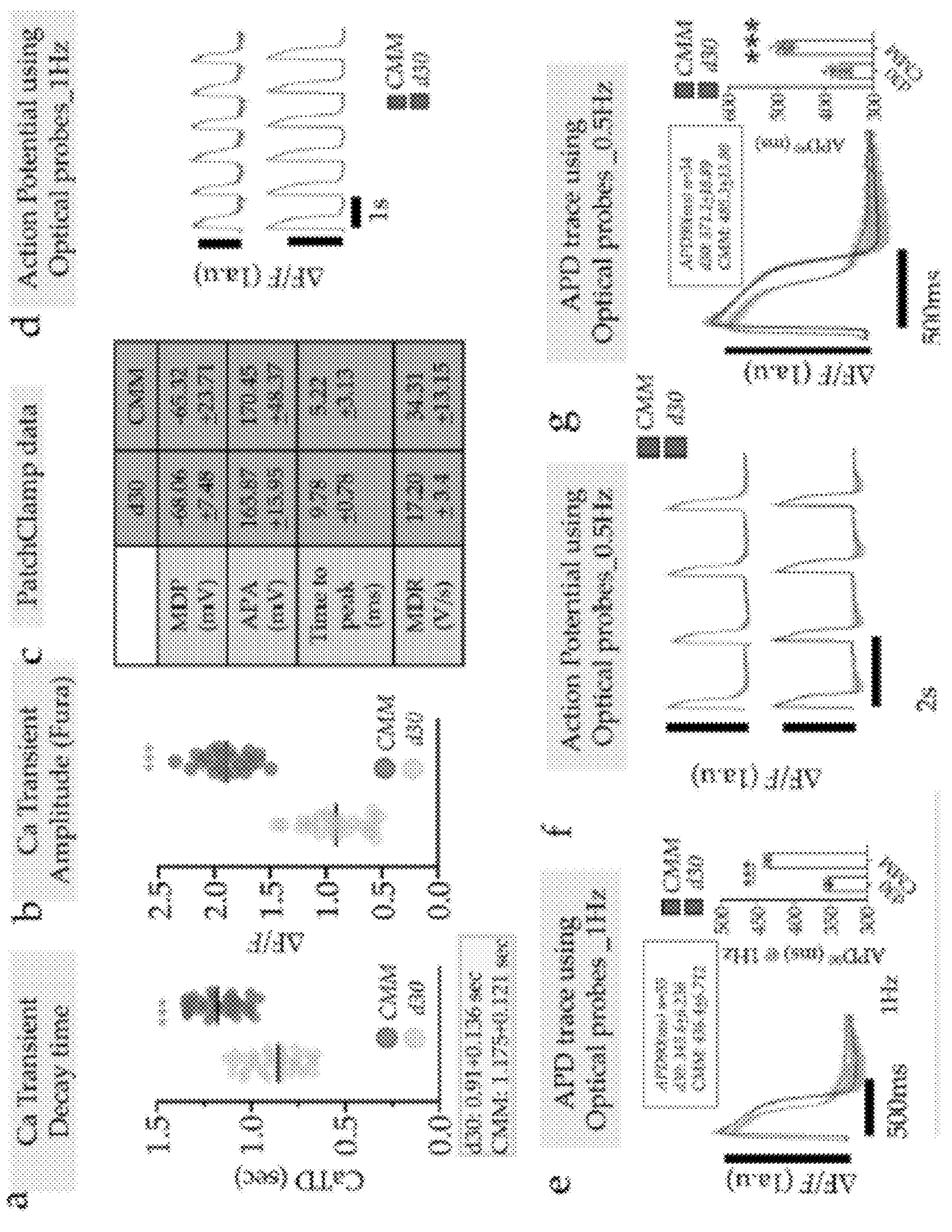
FIG. 19 shows calcium handling and EP maturation, Related to FIG. 6. (a-b) Increased calcium transient decay time (CaTD) and transient amplitude from the on CMM compared to d30 cells, calculated using ratiometric Fura2 imaging (transient data in FIG. 7*h-i*). Data is presented as +SD with n~30. (c) Patchclamp data: No differences in minimum diastolic potential and action potential amplitude were observed between d30 and CMM while time to peak was reduced and Vmax (maximum diastolic rate) was increased in cells on CMM. (d-g) Optical recording of Action potential using Varnam probe. APD traces (with mean+SD from 3 biological batches) show increase amplitude and prolonged APD in cells on CMM when paced at 1 Hz (d-e) and 0.5 Hz (f-g). (h-k) Optical recordings of action potential (with mean+SD from 2 biological batches) following ion channel inhibitors in cells on CMM (using Varnam probe): Lidocaine ($I_{Na}$ 100 um), Dofetilide ($I_{kr}$ 3 nM), Nifedipine ($I_{ca(L)}$ 100 nM), n=30 for each compound. Lidocaine reduces beat frequency (bar plot is displayed as +SD). Dofetilide causes appearance of EAD and APD prolongation. Nifedipine shortens APD; Cells on CMM were sensitive to 10 nM Dofetilide within seconds therefore 3 nM dose was used. Ion Channel Inhibitors. n=10 in both biological batches. Statistical significance is defined as the p<0.05 (*). Bar plots are presented from same data with +SD. Statistical significance is defined as p<0.001 (***).
Figure 19:
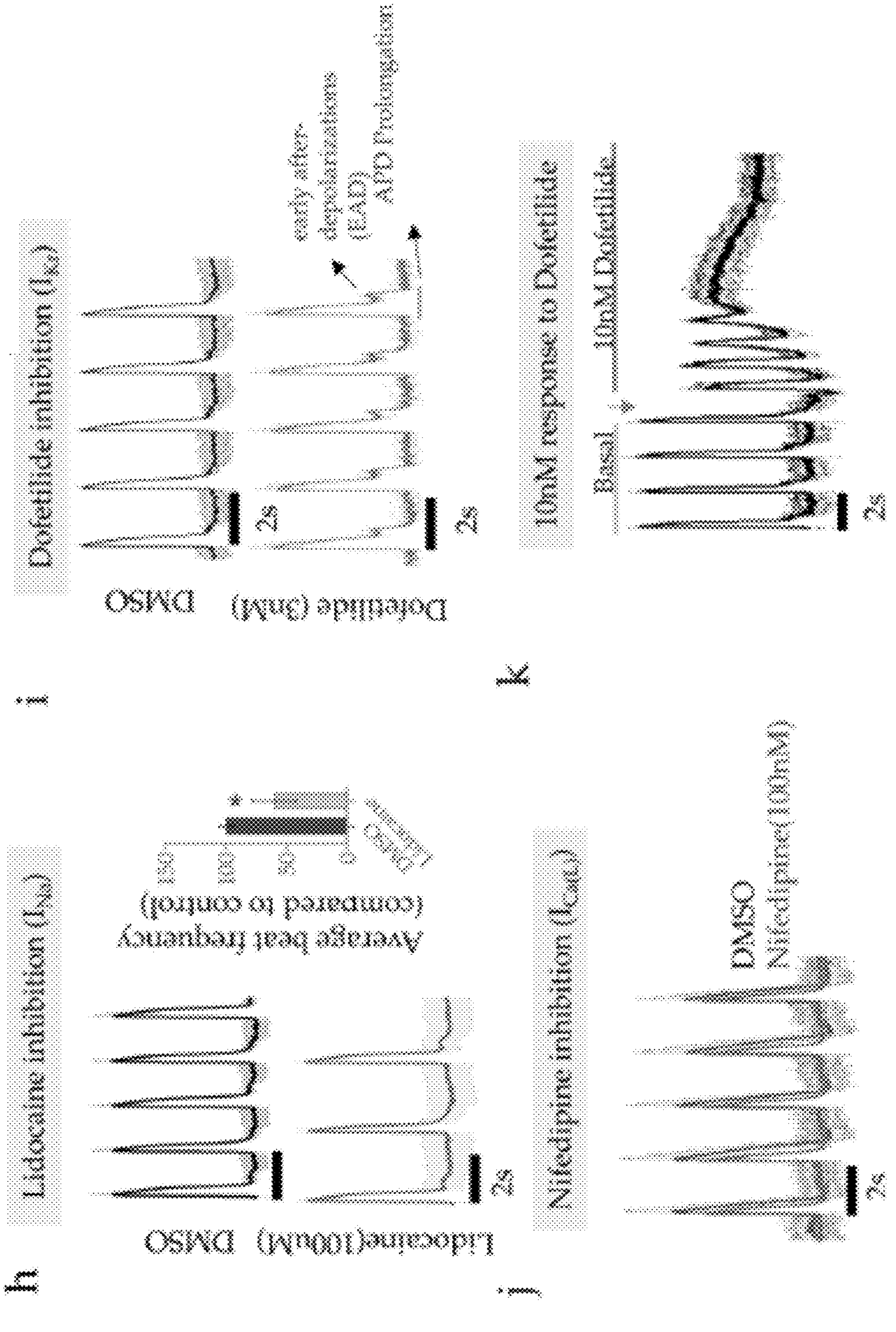

To support increased ATP generation from OxPhos, cells require high mitochondrial number, which are typically fused and elongated in adult cardiomyocytes, as well as upregulation of ETC subunits. MFN1, MFN2, DNM1L, OPA1, and other genes related to mitochondrial fusion were up-regulated on CMM (FIG. 5*a*). Transmission Electron Microscopy (TEM) showed that cells on CMM demonstrate elongated and fused mitochondria (average size 1.73 μM) (FIG. 5*b-c*). qRT-PCR of mitochondrial dna showed >2 times higher expression in CMM vs d30 or d60 (FIG. 5*d*). Relative per cell mitochondrial content (Mitotracker Green intensity) showed >3 times higher levels in hiPSC-CMs cultured on CMM vs d30 (FIG. 5*e-f*). Interestingly, cells showed two subpopulations with low, and high mitochondrial content, the latter significantly enriched on CMM (FIG. 5*e*). As all cells including d30 controls were $cTnT^{+ve}$ (FIG. 9), along with the previous data on cTnT, and MYL2 distribution, these data show enrichment of a metabolically and structurally mature ventricular myocyte type phenotype on CMM. Significantly higher levels of key ETC subunits (I, II, III) and ATP synthase subunit-V was observed, in cells on CMM in three biological replicates, although protein expression levels for subunit IV were not different (FIG. 5*h*-I, 18). These results demonstrate CMM induces increases in mitochondrial content, structural maturation, and quality.

Example 10: Improved Electrophysiological and Calcium Transient on CMM

Figure 6:
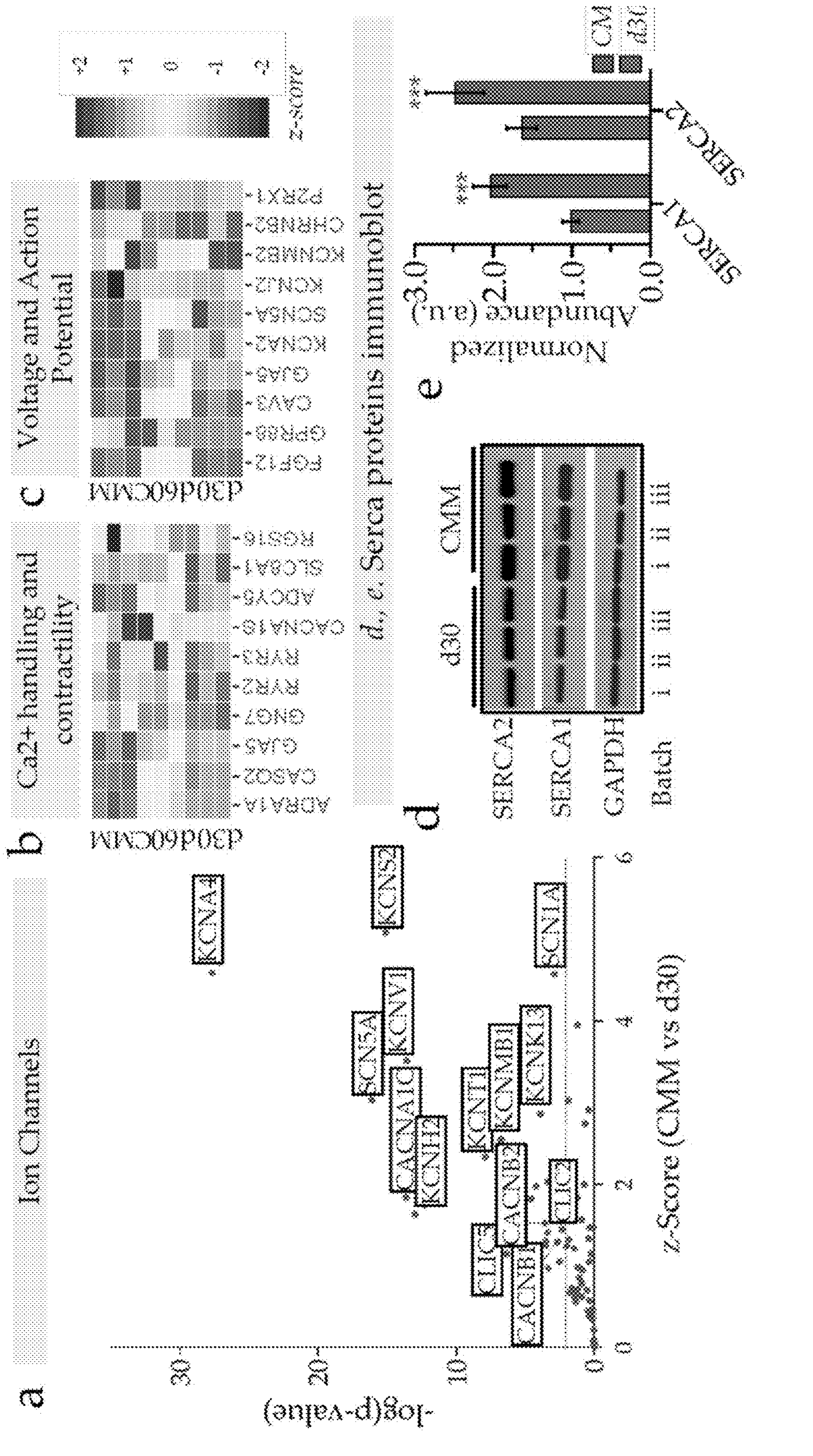
FIG. 6 shows CMM improves calcium handling and EP maturation. (a) Ion channels with increased expression in CMM compared to d30. (b) Calcium handling, and (c) Voltage and Action Potential related genes with increased expression in CMM vs d30. (d-e) Immunoblot of serca proteins. (f-g) Calcium transient of cells on CMM and d30 using GCamp6f. Normalized calcium traces and a representative normalized calcium trace of calcium showed higher transient amplitude on CMM. (h-i) Sarcoplasmic reticulum (SR) calcium content using ratiometric Fura2 imaging. (h) Caffeine (10 mM) exposure shows significant calcium release from CMM cells. (j) Immunostaining of RYR2 and membrane labeling with WGA. White arrows show RYR2 on CMM and arrow indicates cytoplasmic RYR2 in d30. (k-m) Electrophysiological Patchclamp analysis. (k) Increase APD50 & APD90 in cells on CMM vs d30. (l-m) Cells on CMM were more responsive to calcium channel ($Ca_L$) inhibition using Nifedipine ($Ic_{a(L)}$ 100 nM). (n) Response to Ion channel inhibitors in cells on CMM using optical recording of action potential with Varnam probe. Averaged single AP traces show cells on CMM respond to ion channel inhibitors: Lidocaine ($I_{Na}$ 100 um), Dofetilide ($I_{Kr}$, 3 nM), Nifedipine ($I_{Ca(L)}$ 100 nM). For Calcium and AP data, x-axis (time) and y-axis (intensity) are scaled/normalized to same unit for both CMM and d30 to represent them together. Each panel has units defined by black bar.
Figure 6:
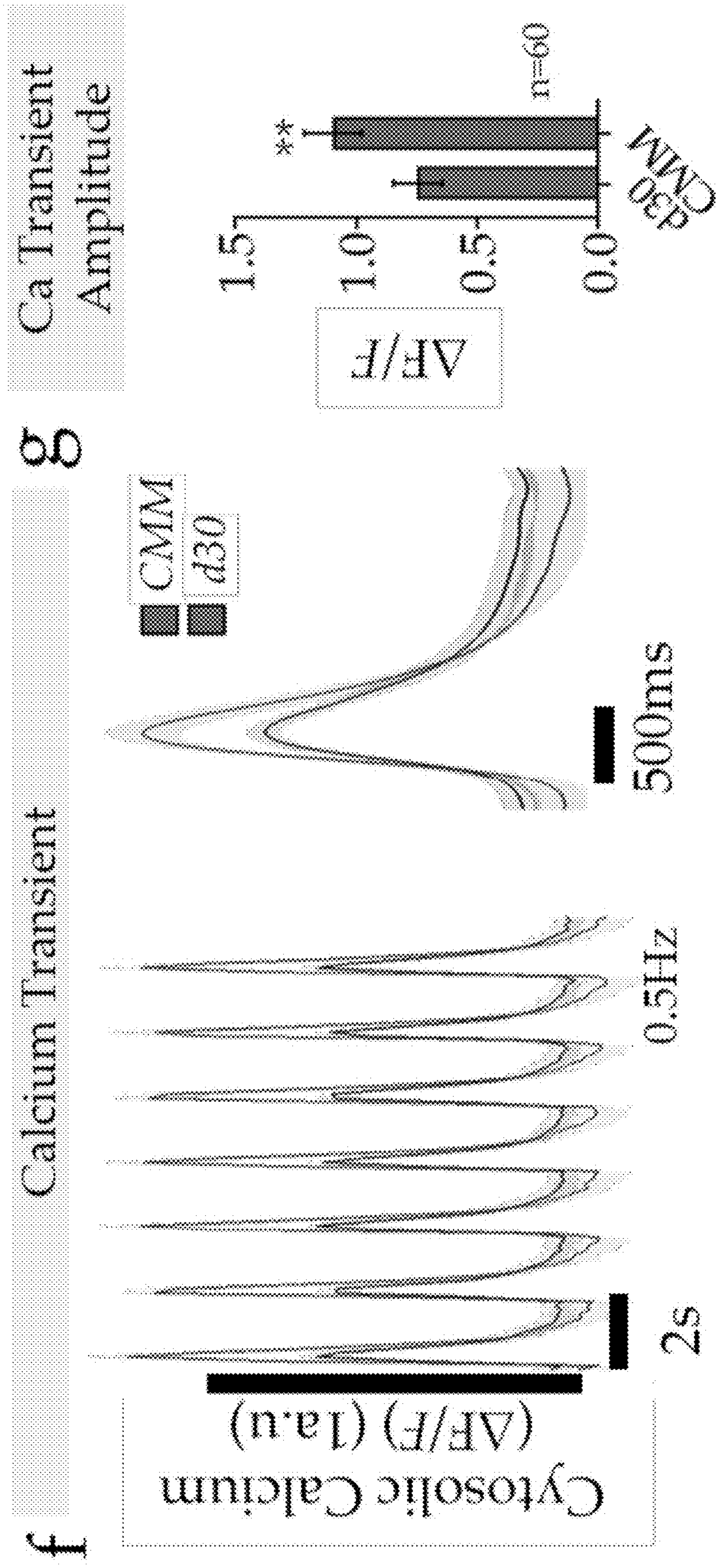
Figure 6:
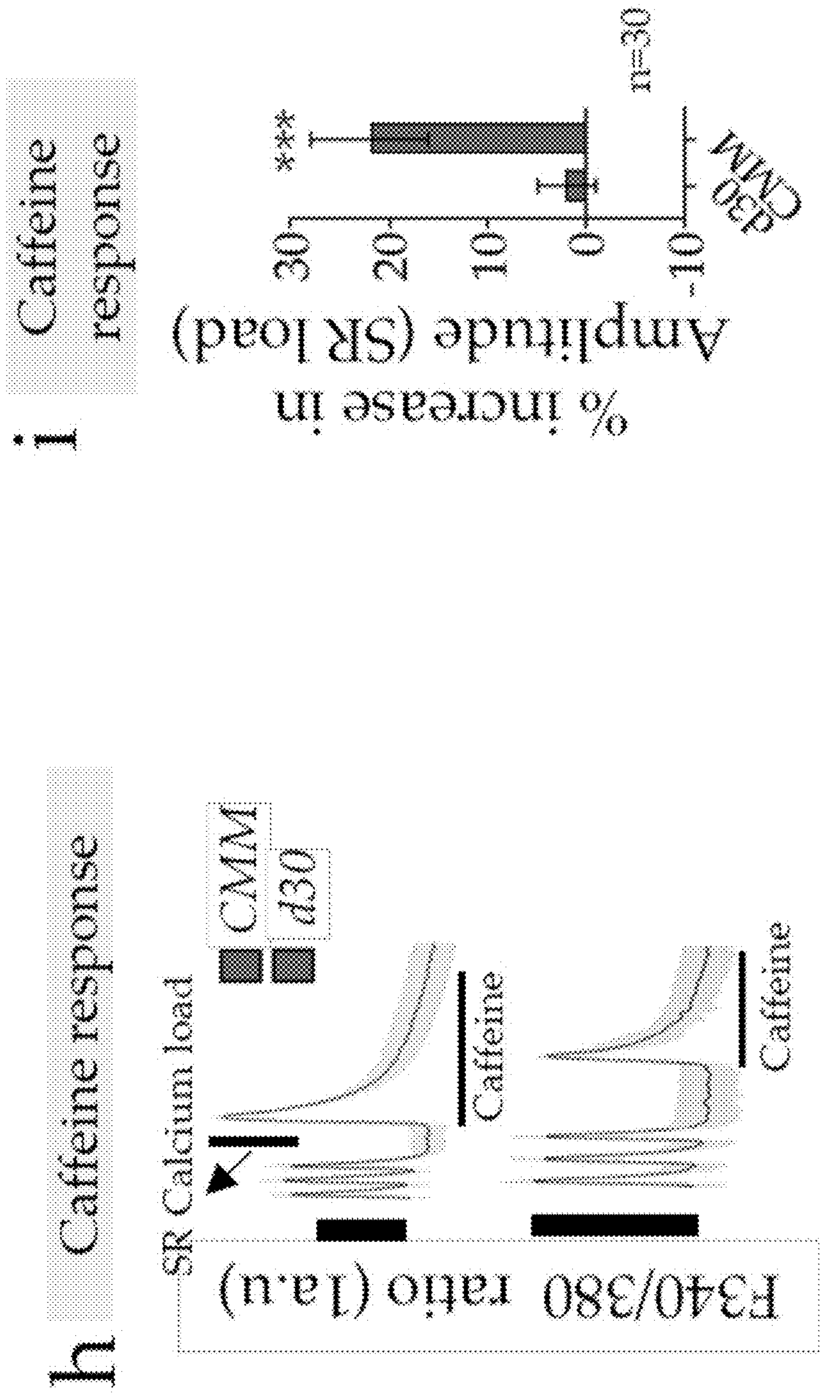
Figure 6:
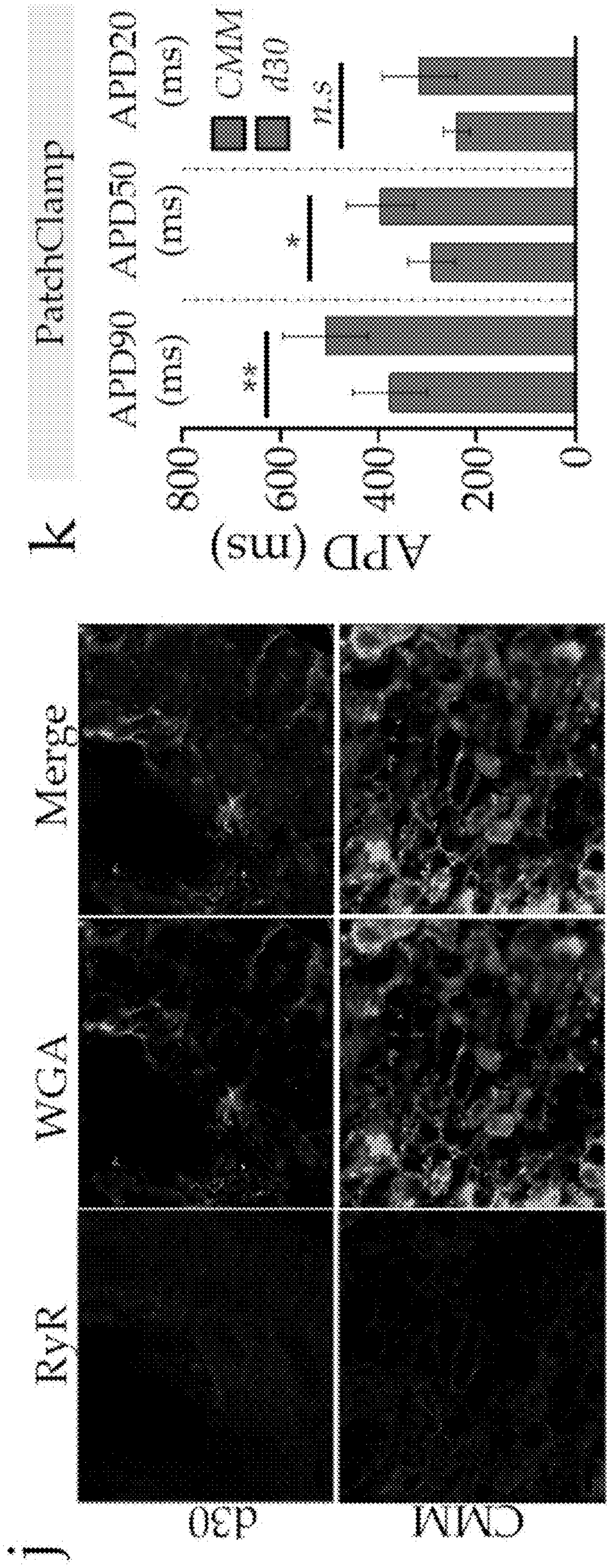
Figure 6:
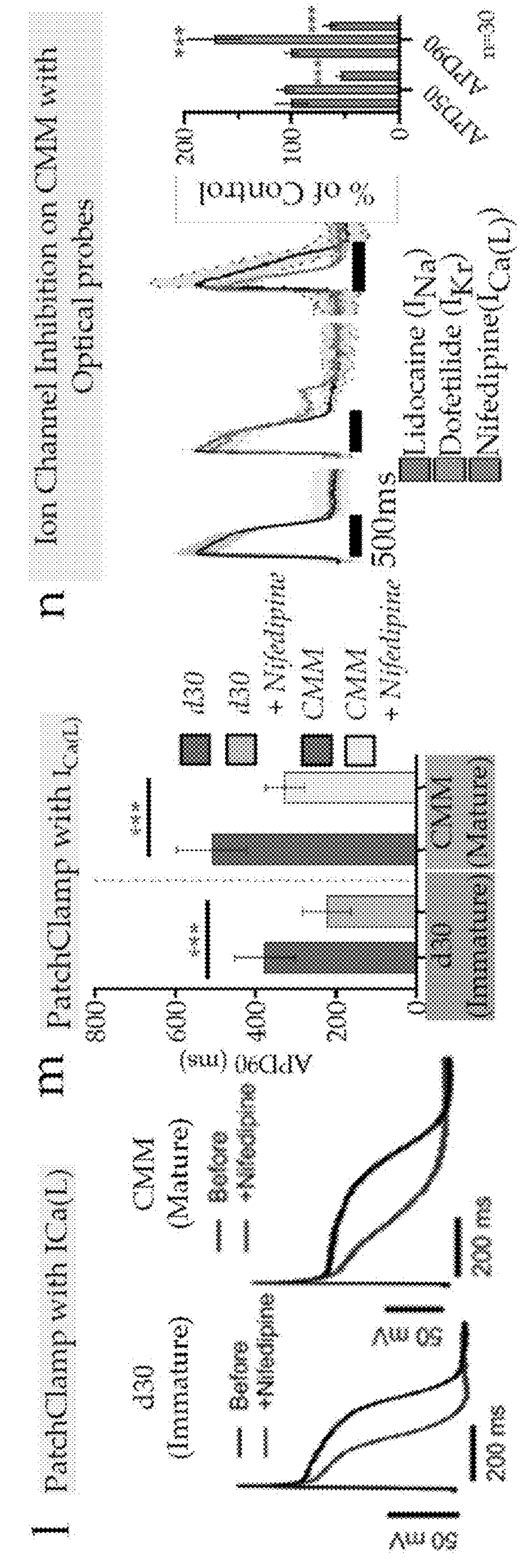

Cardiac tissue development leads to coordinated electrical excitation coupled to contraction known as excitation contraction coupling (ECC)(Bers, 2002). The interplay of ions for ECC requires specific expression of proteins including L-type $Ca^{2+}$ channels (LTCC), ryanodine receptors, sarco/endoplasmic reticulum $Ca^{2+}$ ATPase (SERCA) and $Na^{+}$/$Ca^{2+}$ exchanger(Bers, 2002; Liu et al., 2016). Cardiac maturation on CMM led to a synchronous but slow beating rate of cells (FIG. 3*o*, 17*f-g*)(Keung et al., 2014; Sartiani et al., 2007). CMM showed significant upregulation of several ion channels transcripts present in developed myocytes (FIG. 6*a*). Channel components encoded by these genes are involved in rapid upstroke (SCNA5-encodes Nav1.5) and phase 1 of repolarization (Kv1.4-KCNA4). Several key calcium handling genes including L-type calcium channels (LTCC), ryanodine receptors (RyR), calsequestrin (Casq2) and phospholamban (Pln) were also upregulated indicating better maturation on CMM even compared to d60 (FIG. 6*b-c*).

Efficient calcium cycling is crucial to convert electrical signal to mechanical force in the myocytes(Bers, 2002), and calcium transient profiles inform the extent of maturation (Liu et al., 2009). SERCA had higher abundance CMM vs control (FIG. 6*d-e*). Using GCamp6f, higher $Ca^{2+}$ transient amplitude (ΔF/F) in CMM compared to d30 was found (FIG. 6*f-g*). To evaluate calcium handling efficiency, caffeine-induced $Ca^{2+}$ release from the sarcoplasmic reticulum (SR) for calcium storage (SR Load) was investigated using 10 mM caffeine in Fura2 (ratiometric dye) loaded cells(Feyen et al., 2020). Cells matured on CMM demonstrated increased calcium decay time and calcium amplitude, and a significant increase in amplitude following caffeine exposure, while d30 cells failed to demonstrate the calcium release from SR (FIG. 6*h*-I, 19*a-b*). Ryanodine receptors (RYR2), a $Ca^{2+}$-induced $Ca^{2+}$ release (CICR) modulator, were also localized near the WGA labeled membranes with low cytoplasmic localization in CMM compared to d30 (FIG. 6*j*).

Single cell patch clamp was performed and it was found that CMM significantly increased action potential duration (APD) APD90 and APD50 vs d30 (FIG. 6*k*, 17*c*). No statistical difference was observed between d30 and CMM on maximum diastolic potential (MDP) and AP amplitude (APA) which was about −70 mV and 170 mV respectively (FIG. 17*c*). Significant reduction in time to peak (5.22 ms versus 9.78 ms) and maximum depolarization rate (MDR) in cells on CMM compared to d30 cells was observed (FIG. 17*c*). Similar APD profiles with genetically encoded voltage indicators were obtained (Jin et al., 2012; Kannan et al., 2018) which exhibited the action potential duration (APD90) of 436.4±6.71 ms compared to 345.6±6.23 ms in d30 cells at 1 Hz and 485.3±13.80 ms compared to 371.1±18.89 ms in d30 cells at 0.5 Hz (Barbuti et al., 2016), (FIG. 17*d-g*). The effect of 100 nM Nifedipine, a L-type $Ca^{2+}$ channel blocker using patch clamp was investigate and found significant reduction of APD90 on both, with greater response in cells on CMM (FIG. 6*l-m*). A comprehensive ion channel inhibition on cells matured on CMM was performed (FIG. 6*n*, 17*h-k*). Lidocaine, a sodium channel blocker reduced the frequency (by ~40% in 2 biological batches; n=30) (FIGS. 6*n* and 17*h*), while potassium channel inhibition by Dofetilide induced AP prolongation and early after depolarization (EAD) (FIGS. 6*n* and 17*i*). Dofetilide is a well characterized drug associated with corrected QT interval (QTc) prolongation and torsades de pointes (TdP), and is a human ether-a-go-go-related gene (hERG) K(+) channel blocker used to evaluate maturity of iPSC-CMs for their utility in cardiotoxicity screens(Shi et al., 2020). Cells on CMM were sensitive to 3 nM dose of Dofetilide while they fail to tolerate 10 nM dose range (FIG. 17*j*). Nifedipine reduced the AP duration (APD50, APD90) without affecting frequency (FIG. 6*n*, 17*k*). These results show significant electrophysiological (EP) maturation of cells on CMM.

Example 11: CMM Mitigates Response of Pathological Hypertrophy Induction

With establishment of transcriptional, metabolic, redox, and calcium handling characteristic of a matured cardiac tissue, the effect of a key pathological stimulus, endothelin-1 (ET-1) treatment on cardiac cells was tested (FIG. 7*a*). Endothelin mediates a wide range of effects on cardiac tissue, with an increase in muscle size and abnormalities in cellular contractility, and calcium dynamics resulting in pathological hypertrophy(Archer et al., 2017). Like most cardiac diseases, pathological hypertrophy is a slow progressing disease resulting from chronic elevated workload on the heart, resulting in cardiac remodeling without myocyte proliferation and gradual disruption in normal matrix architecture(Marian and Braunwald, 2017; Rossi, 1998), which itself accentuates and accelerates disease progression (Kim et al., 2000; Sewanan et al., 2019). Culture of hiPSC-CMs on non-physiological architecture (d30) may prime cells to be more sensitive to ET-1 induced pathological hypertrophy. Both d30 and CMM constructs were treated with ET-1 for 48 hours, and profiled gene expression using RNA Sequencing. ET-1 samples were compared with their own respective untreated control samples (d30, or CMM), as the maturation state of cells is expected to be different in either matrix contexts (FIG. 7*a*).

Figure 20:
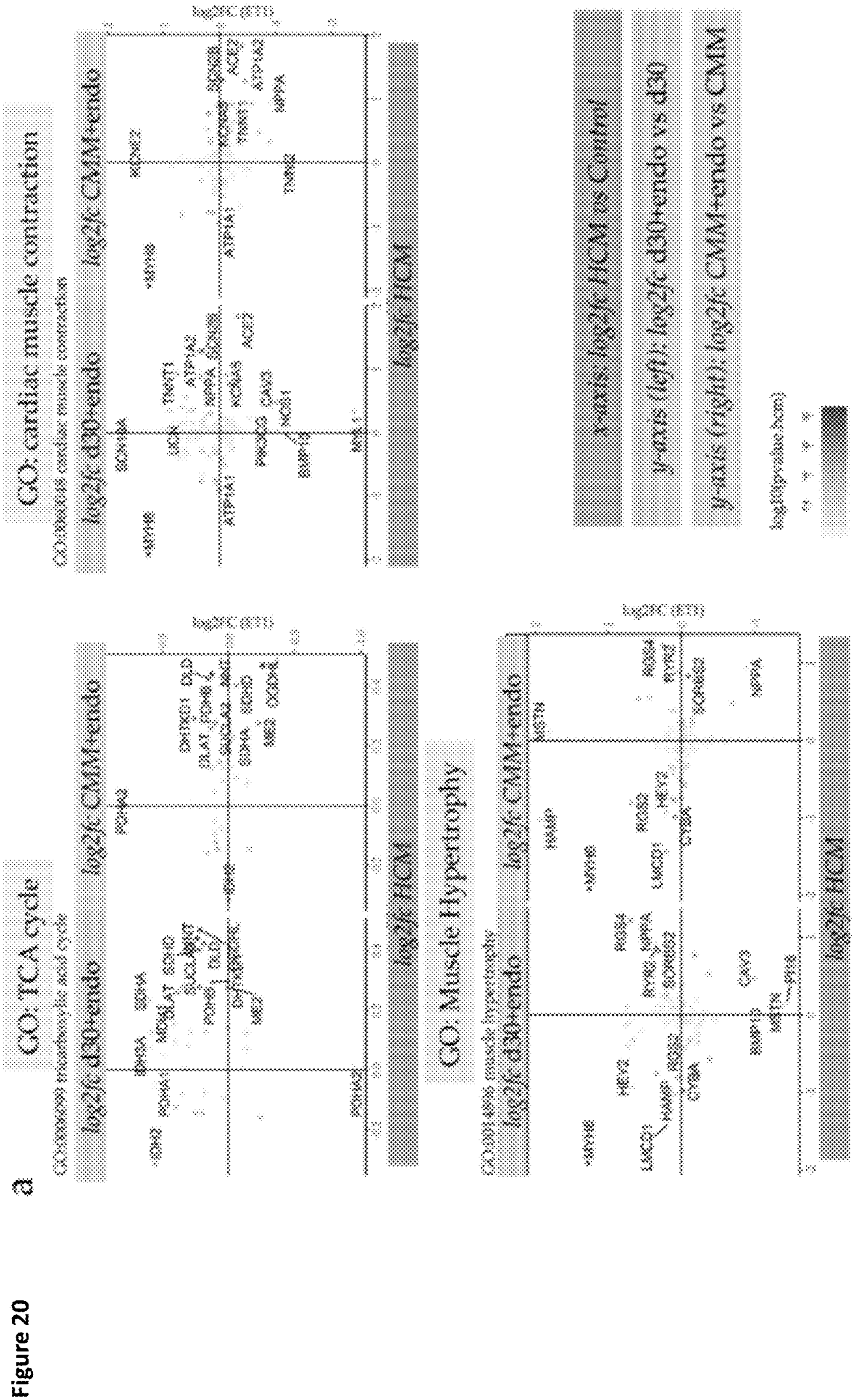
FIG. 20 shows comparison of HCM dataset with endothelin treated d30 and CMM samples, Related to FIG. 7. (a) Utilizing online Mayo clinic HCM myectomy datasets (GSE36961), comparison was performed in select ontologies in TCA, cardiac muscle contraction and muscle hypertrophy. Cells on CMM with endothelin treatment showed downregulation of some TCA cycle intermediaries, ANP (Nppa), cardiac muscle contraction and hypertrophy transcripts in comparison with HCM or with d30 endo treatment. The differential gene lists were obtained from HCM vs control, d30+endo vs d30 and CMM+endo vs CMM. X-axis represents the log 2fc of HCM vs control and y axis represent d30+endo vs d30 (left) and CMM+endo vs CMM (right). Color intensity bar represents the log 10pVal of genes in HCM dataset. (b) Ranked gene list comparison of top 100 HCM genes compared with endo treatment on CMM and d30. Enrichment in CMM+endo was observed when compared to top 100 HCM negative genes (downregulated in HCM compared to control) indicating opposite different differential response. Top100 HCMpos genes (upregulated in HCM versus control) when compared to CMM+endo and flat+endo do not show any enrichment.
Figure 20:
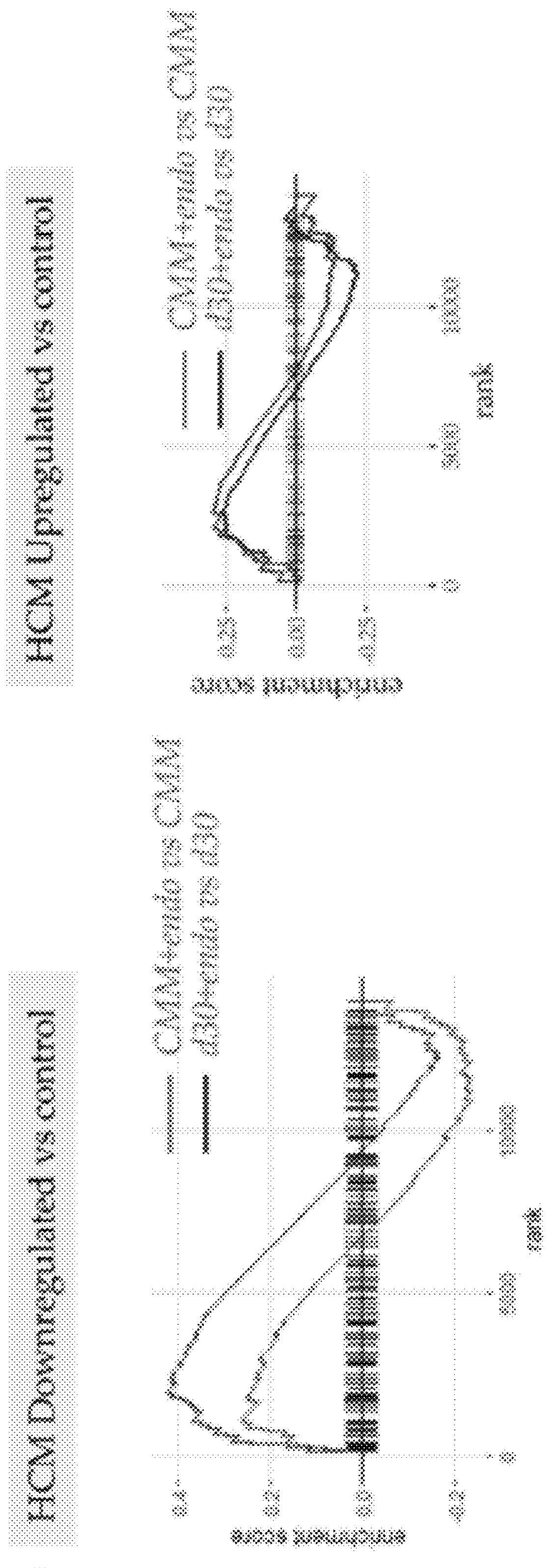
Figure 21:
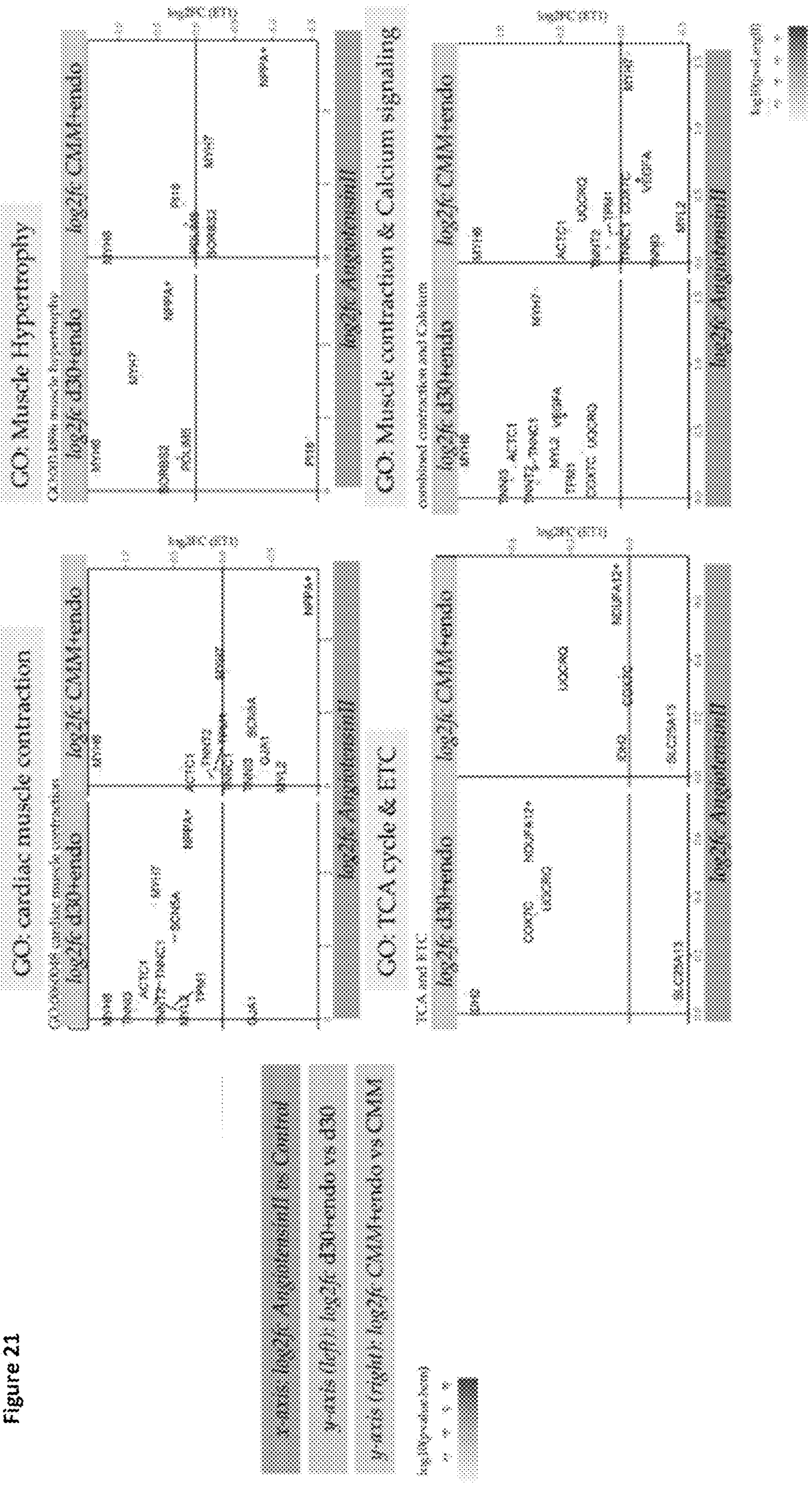
FIG. 21 shows comparison of AngiotensinII treated mice model with endothelin treated d30 and CMM samples, Related to FIG. 7. Utilizing scRNA seq data (from McLellan et al Circulation. 2020; 142:1448-1463), comparison was performed in select ontologies of cardiac muscle contraction, muscle hypertrophy, combination of TCA and electron transport chain (ETC), and muscle contraction and calcium signaling. Only cardiac myocytes data from the mice scRNA seq was used in the analysis. Cells on CMM with endothelin treatment showed downregulation of ANP (Nppa), Myh7 and other genes (including ETC intermediates) compared to both AngiotensinII treatment and d30 endo treatment. Cells on d30 endo treatment also upregulate several of contractility genes which are not observed in either AngII treatment or CMM+endo. The differential genelists were obtained from d30+endo vs d30, CMM+endo vs CMM and HCM vs control. X-axis represents the log 2fc of HCM vs control and y axis represent d30+endo vs d30 (left) and CMM+endo vs CMM (right). Grayscale intensity bar represents the log 10pVal of genes in AngII dataset.
Figure 22:
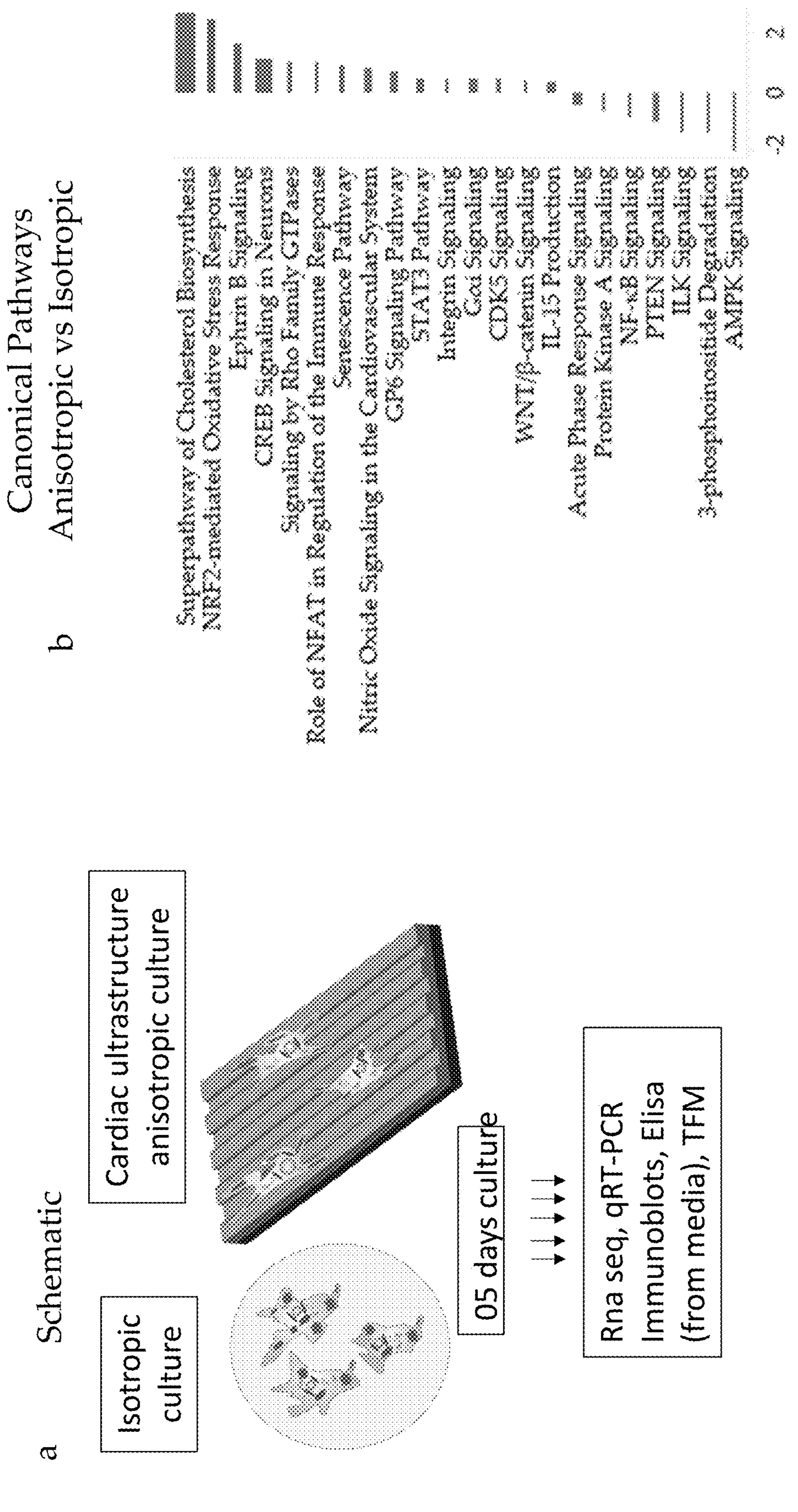
FIG. 22 shows physiologically isotropic matrix nanotopography mitigate progression of cardiac fibrosis. (a) Schematic showing cardiac fibroblasts seeded either on a flat, or isotropic wrinkled surface or an anisotropically nanowrinkled substrate. Cellular state will be assessed by RNAseq, qRT-PCR, immunoblots, ELISA collected from conditioned medium, traction force microscopy, multiome, or metabolomics. (b) Fold changes in the activated canonical pathways in anisotropic vs isotropic nanowrinkled substrates in cardiac fibroblasts. (c) Activation of transcription factors in cardiac fibroblasts predicted by Ingenuity Pathway analysis in anisotropic vs isotropic surfaces. (d) qRT-PCR showing fold change of key fibroblast associated genes in cardiac fibroblasts cultured on anisotropic vs isotropic surfaces. (e) Phase contrast and immunofluorescence of F-actin in cardiac fibroblasts cultured on anisotropic vs isotropic surfaces. (f-g) Immunofluorescence analysis of fibroblast activation marker aSMA in cardiac fibroblasts cultured on anisotropic surface show lower expression, density vs isotropic surface, while increased polymeric bundling. (h-i) Traction force microscopy analysis of contractile force generation of cardiac fibroblasts cultured on isotropic or anisotropic surface measured in a flat substrate or a nanowrinkled anisotropic substrate (with embedded fluorescent beads to facilitate TFM measurements) show significantly higher strain energy and contractility in latter.
Figure 22:
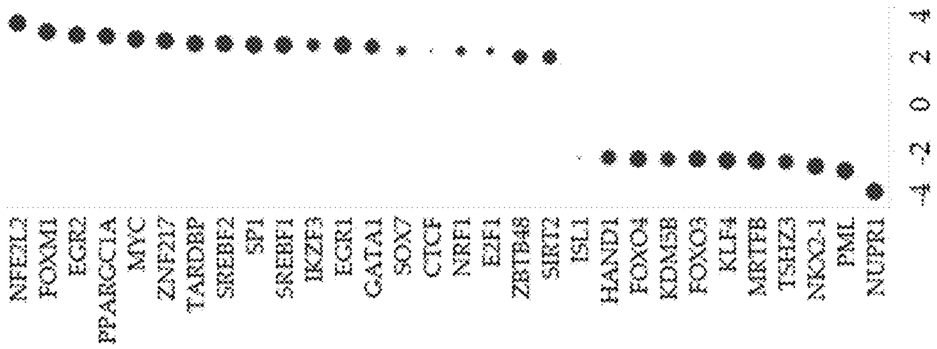
Figure 22:
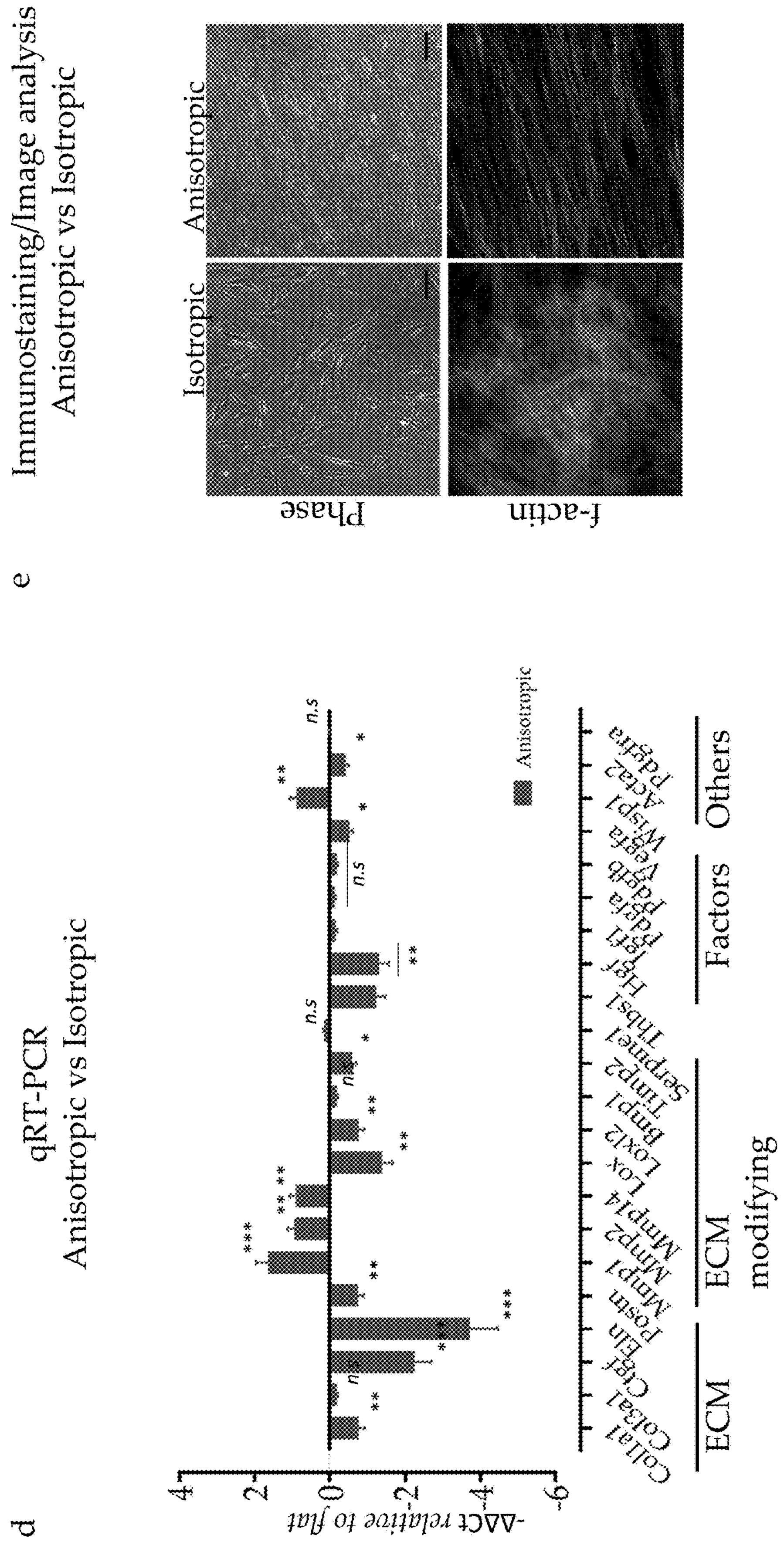
Figure 22:
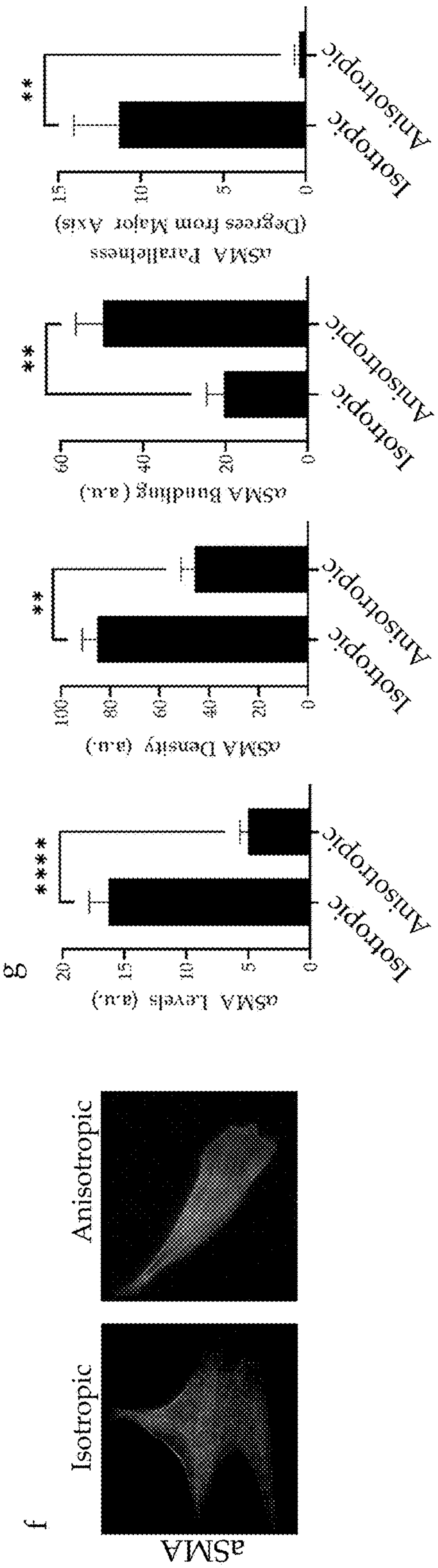
Figure 22:
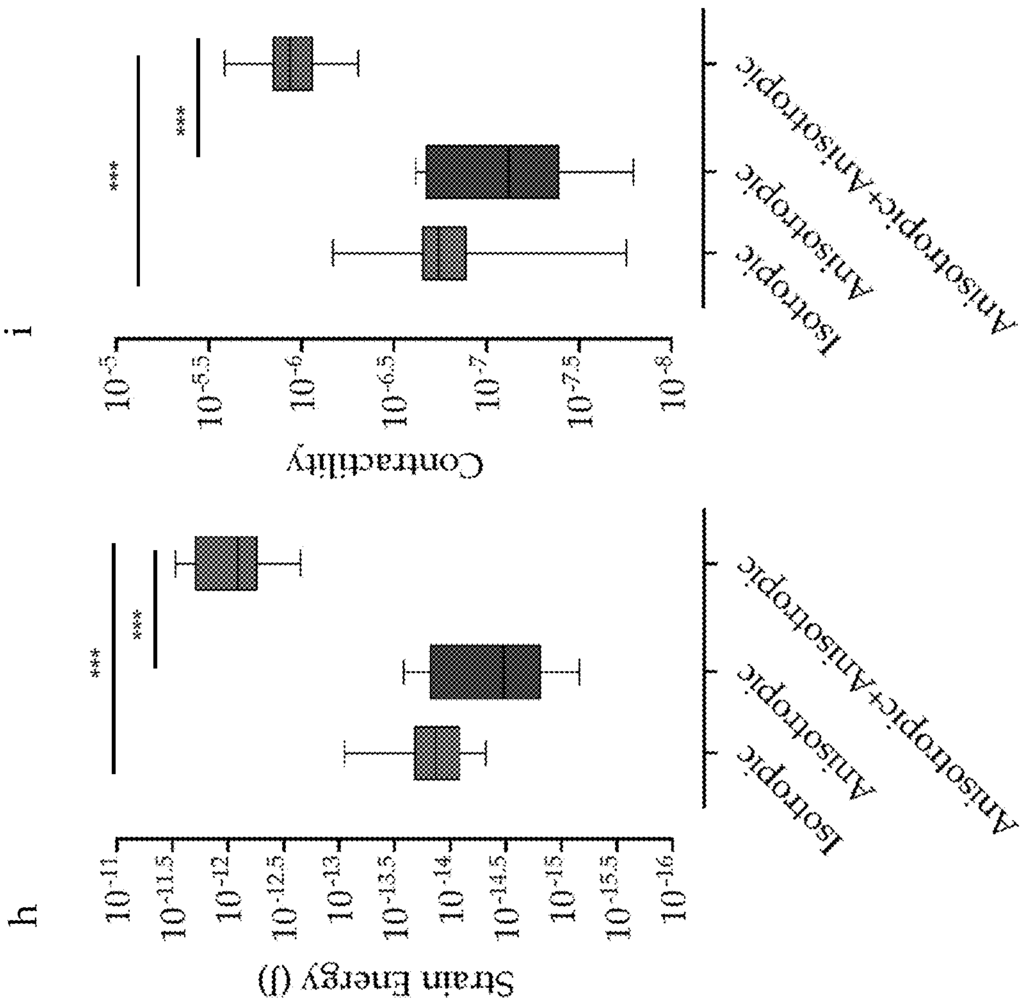
Figure 23:
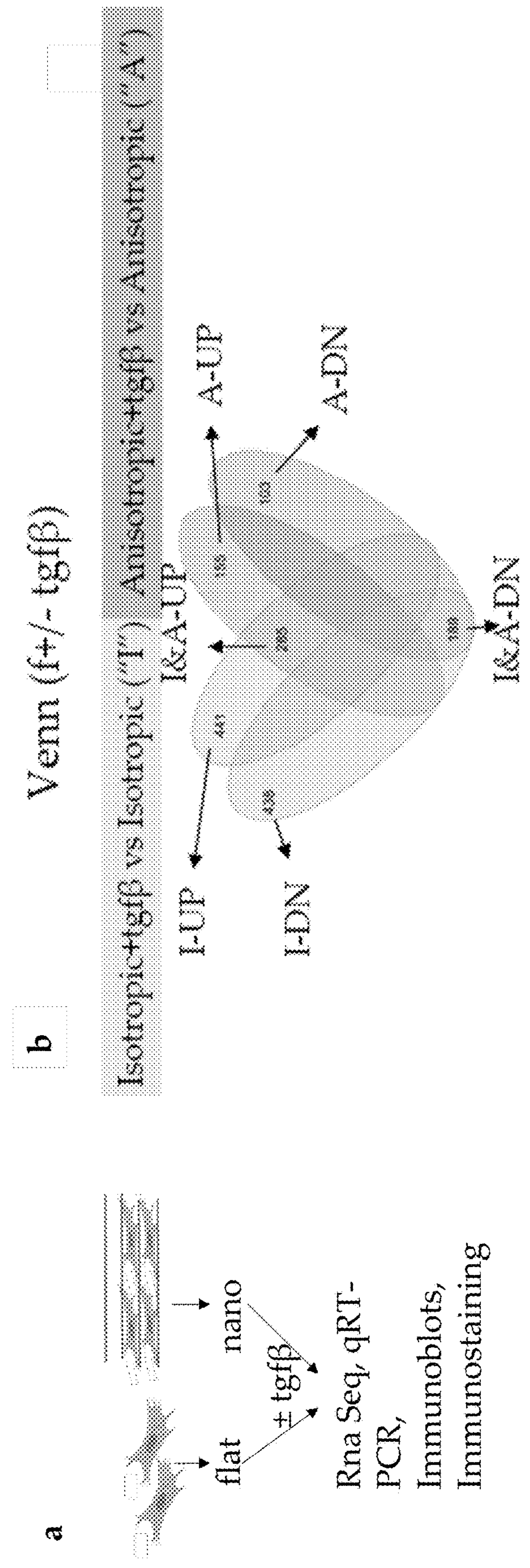
FIG. 23 shows Cardiac fibroblast manifest decreased myofibroblast phenotype, and increased remodeling on physiologically isotropic matrix. (a) Schematic showing experimental design. (b) Venn diagram of gene expression analysis of cardiac fibroblasts cultured on isotropic vs anisotropic surfaced before, and after treatment with TGFb. (d-e) Relative fold change of canonical pathways in cardiac fibroblasts cultured on isotropic vs anisotropic surfaced before, and after treatment with TGFb. (f, h) qRT-PCR showing fold change of gene transcripts associated with fibroblast activation (f), and matrix remodeling enzymes (h) in cardiac fibroblasts cultured on anisotropic vs isotropic surface, isotropic surface with TGFb vs DMSO, and anisotropic surface with TGFb vs DMSO.
Figure 23:
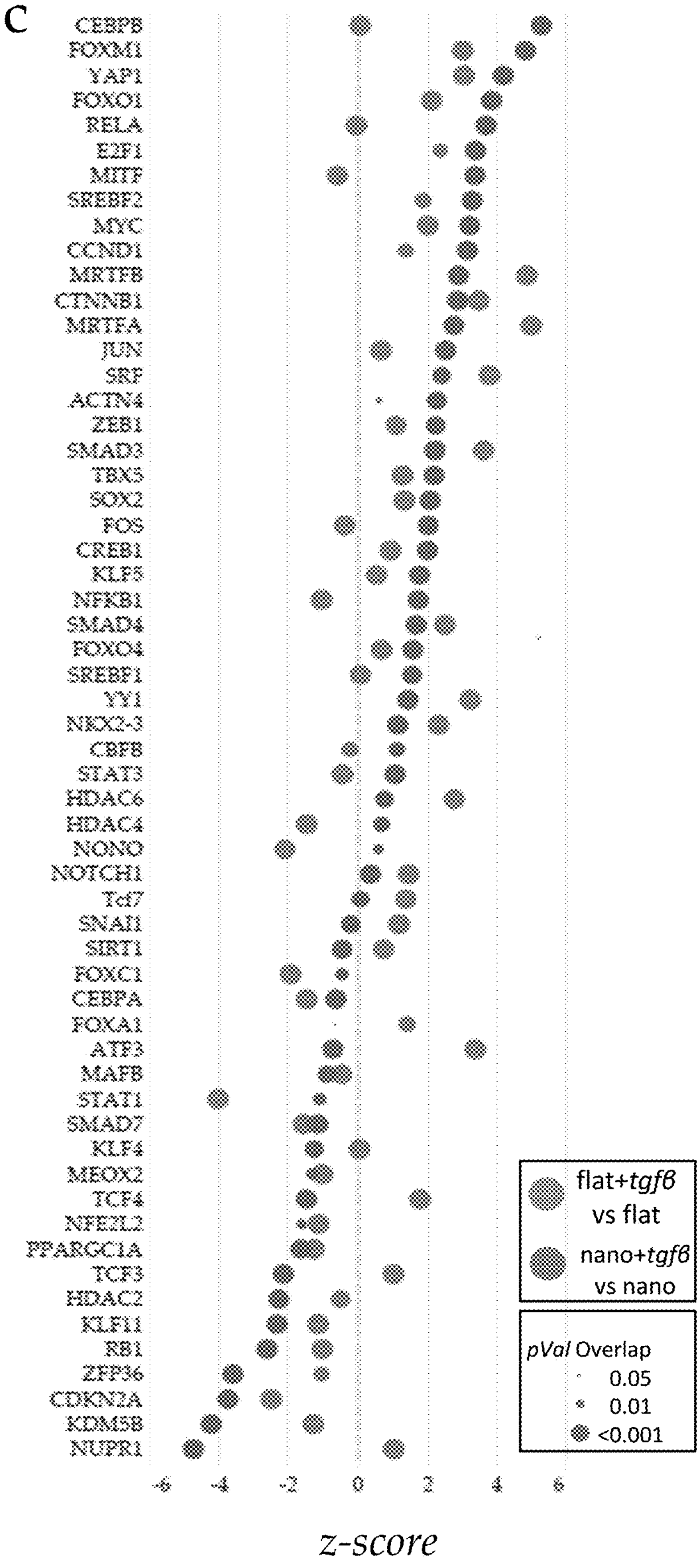
Figure 23:
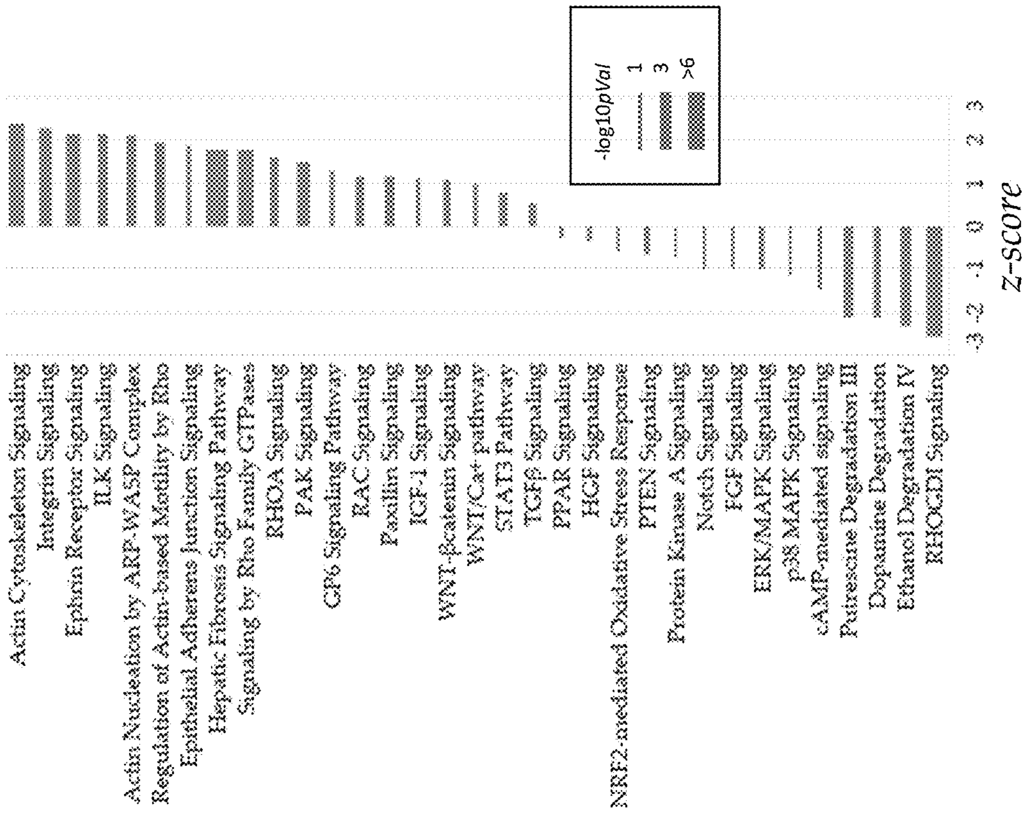
Figure 23:
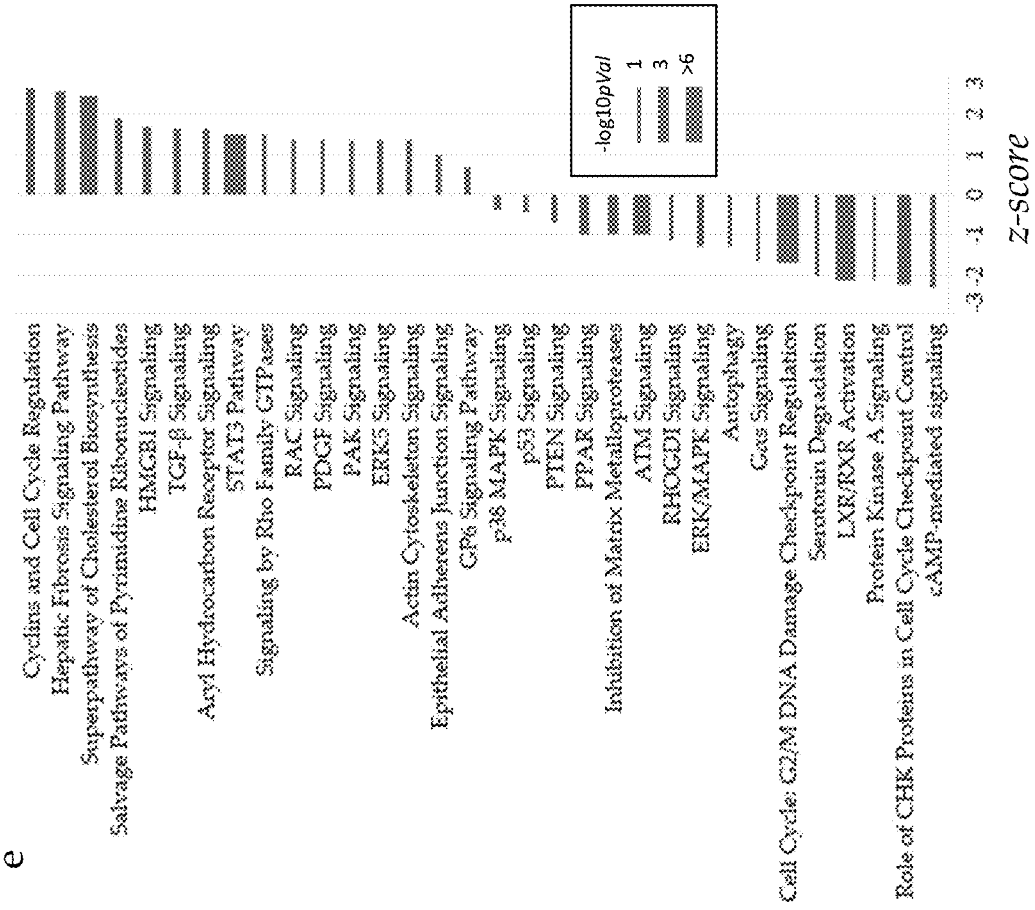
Figure 23:
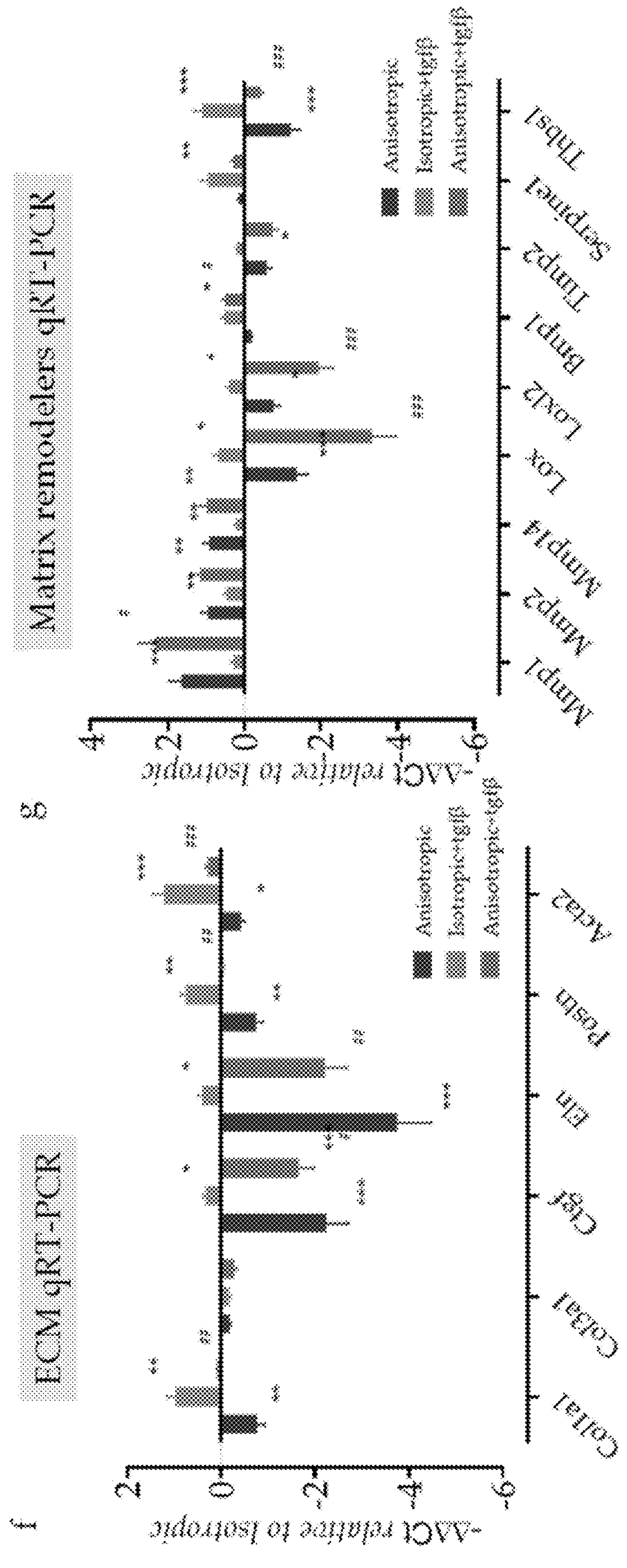
Figure 23:
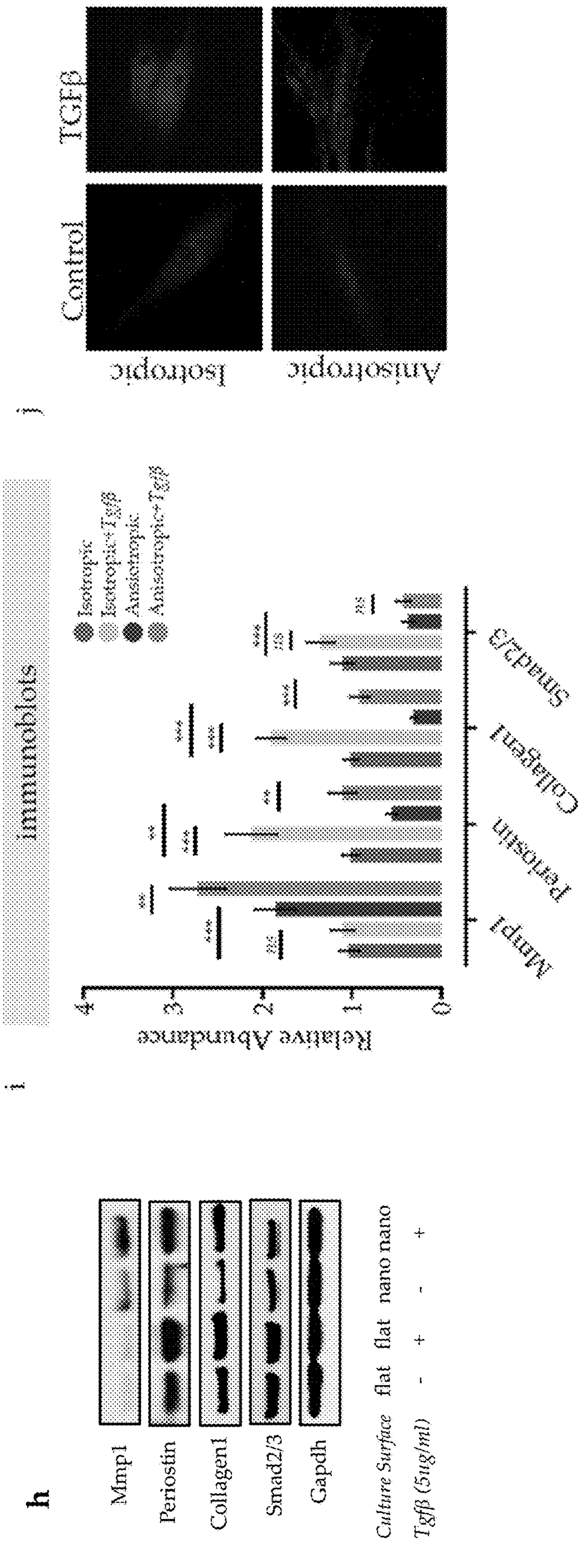
Figure 24:
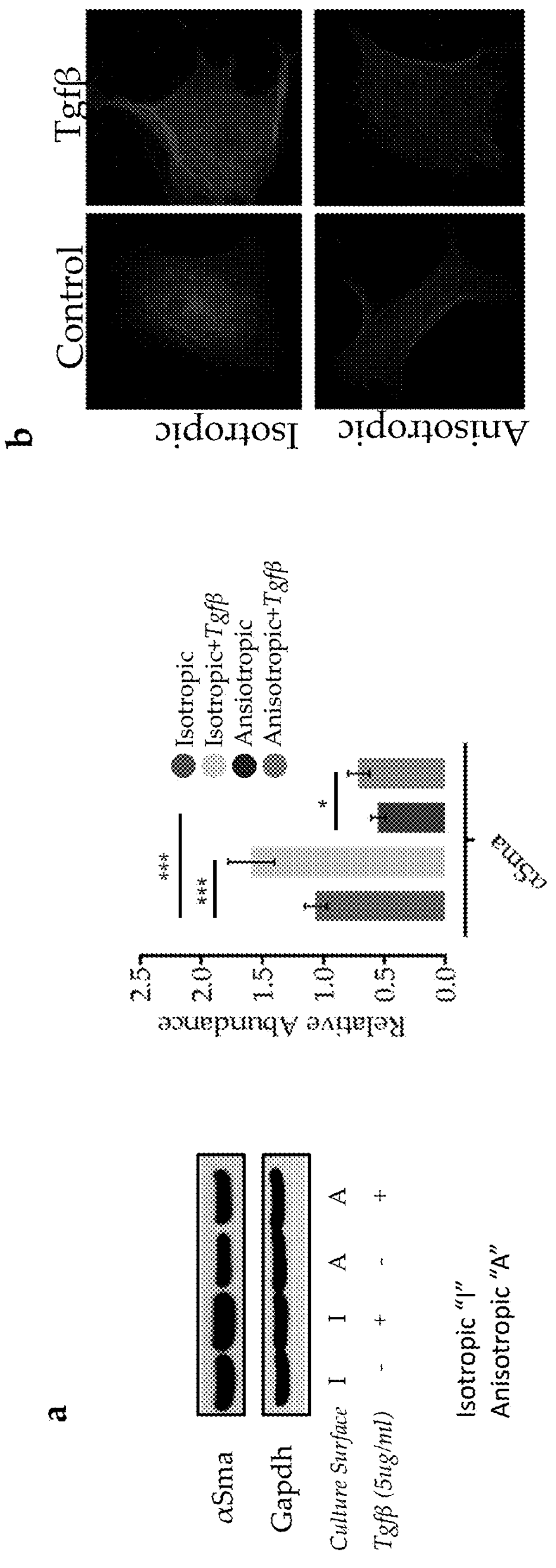
FIG. 24 shows cardiac fibroblasts generate more contractile force in surface with high anisotropic arrangement of matrix topography. (a) Immunoblot showing relative abundance of aSMA in cardiac fibroblasts cultured on isotropic vs anisotropic surfaced before, and after treatment with TGFb, also shown in immunofluorescence images (b). (c) Traction force maps of cardiac fibroblasts cultured on isotropic vs anisotropic surfaced before, and after treatment with TGFb, when measured on a standard TFM hydrogel without embedded topographical features. (d) Schematic showing fabrication of nano-TFM wherein TFM measurement is facilitated on nanowrinkled substrate with a representative traction force map of cardiac fibroblasts. The features of cell culture and measurement are retained. (e-f) Strain energy and contractility of cardiac fibroblasts cultured on isotropic vs anisotropic surfaced before, and after treatment with TGFb either on flat TFM gel, or on nano-TFM. (g) Schematic showing how high fibroblast activation on isotropic surface still results on reduced directional force generation because of random coupling of actomyosin assembly, while the force generation is directional when coupled to extracellular matrix direction, resulting in increased contractile force generation ins spite of reduced aSMA.
Figure 24:
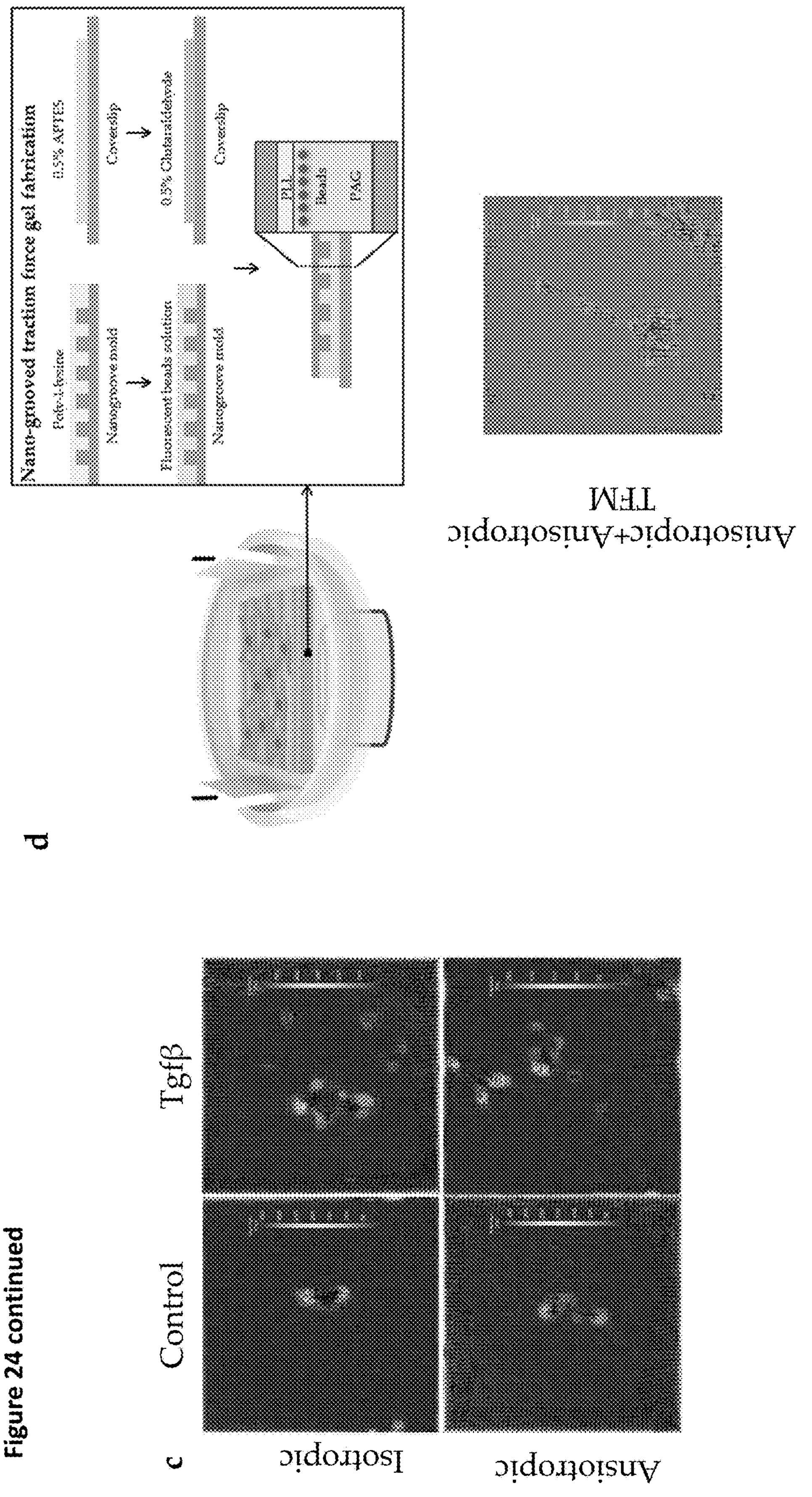
Figure 24:
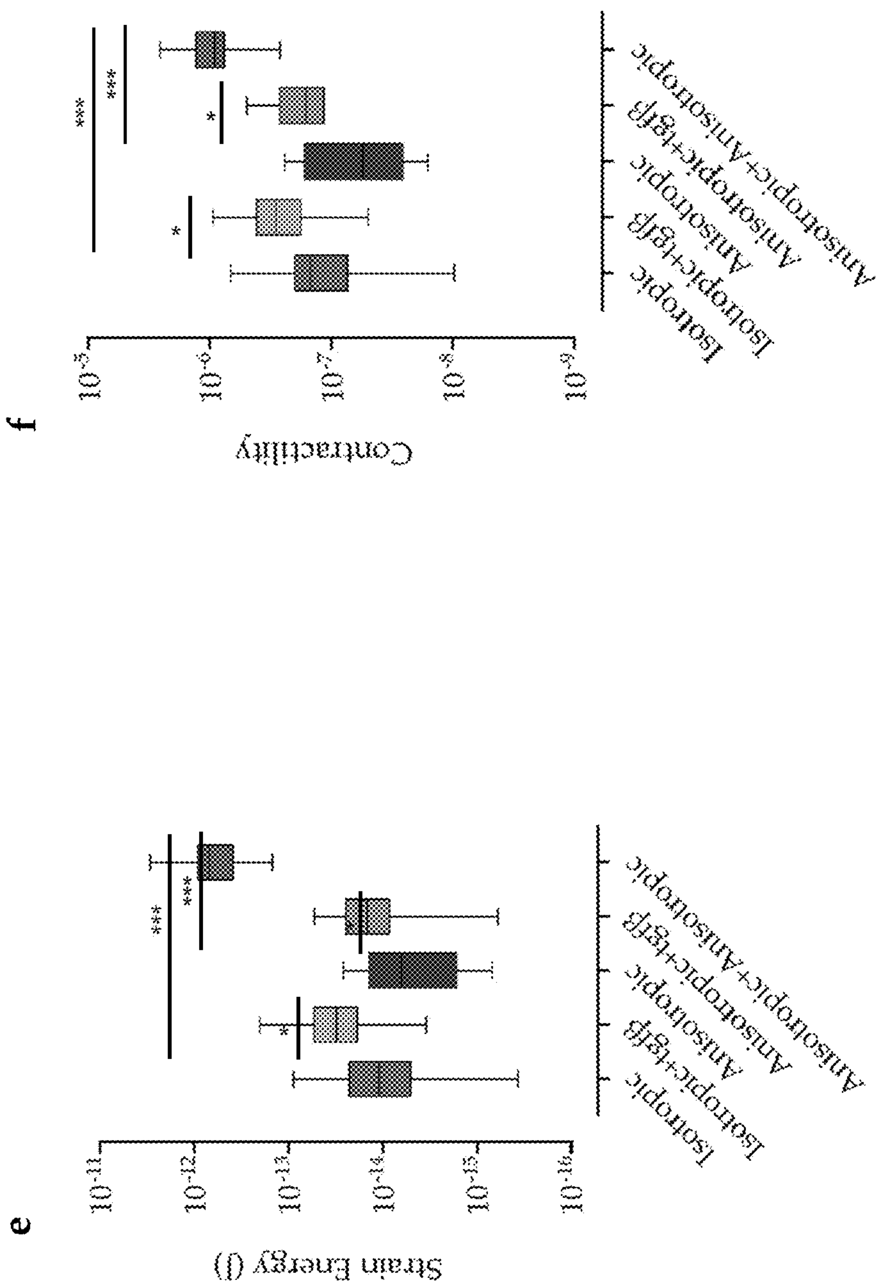
Figure 24:
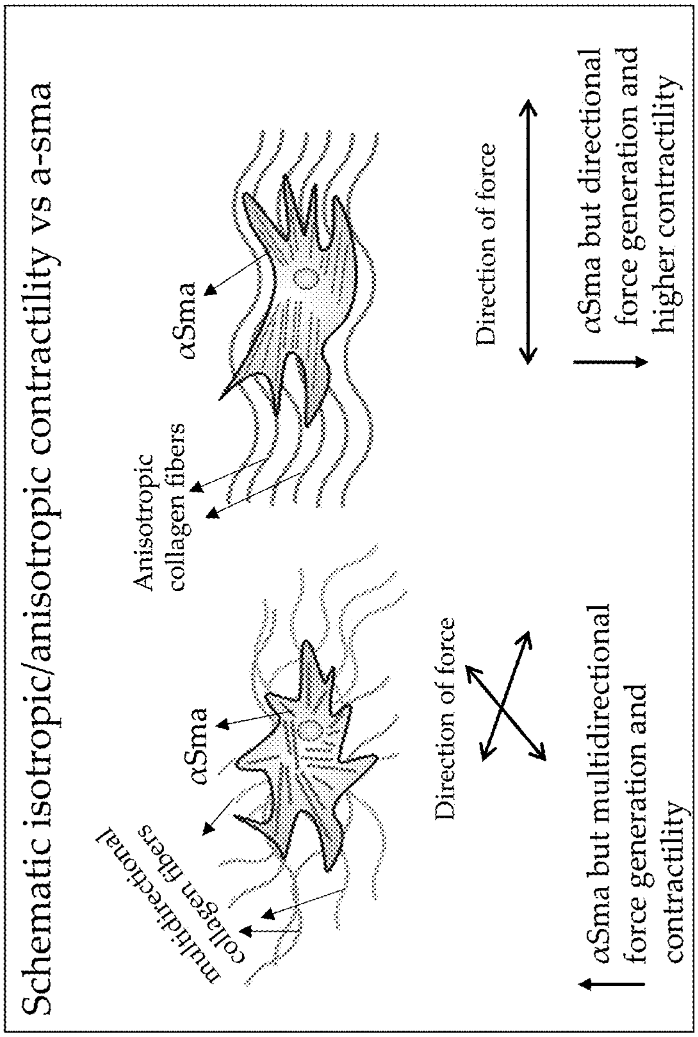

Using IPA pathway analysis, it was found that ET-1 treatment in d30 exhibited differential regulation of gene expression related to adrenergic signaling, metabolism, hypertrophic signaling, calcium and NOS signaling (FIG. 7*b*), while effect on CMM was attenuated. While ET-1 downstream signaling targets and PKA signaling were upregulated in CMM after ET-1 treatment, the metabolic effect was minimal (FIG. 7*b*). IPA analysis predicted activation of key cardiac-specific transcription factors related to cardiogenesis, metabolic transformation and hypertrophy on d30, including GATA4/5, MYOD1, PPARG, TBX5, MEF2A, and MYOC and MYOD1 (FIG. 7*c*). ET-1 treatment increased enrichment of these gene ontologies, their levels were still not similar to CMM which activates maturation related ontologies (calcium, metabolism, electrophysiology) (FIG. 2*c*). Overall, these data show that ET-1 induced hypertrophy is partly attenuated by presence of physiological matrix, or conversely, lack of cardiac specific matrix supports progression of pathological hypertrophy. It was confirmed that this observation by comparing published human gene expression data from hypertrophic myectomy samples (NCBI GEO GSE6961), from patients with established disease phenotype and therefore expected remodeled hearts (FIG. 20-21). Diseased transcripts were compared to their own controls (FIG. 20-21). Several key transcripts showing similar response in HCM patients and d30 with ET-1 treatment were found, including TCA cycle and expression of Nppa compared to CMM (FIG. 20*a*). Using non-parametric based GSEA (gene set enrichment analysis), it was found that transcripts that were downregulated in HCM patients showed opposite enrichment in CMM after ET-1 treatment compared to d30, while no discernable difference was observed in upregulated genes (FIG. 20*b-c*). Further, single cell RNA sequencing data was used from published angiotensin mice model (McLellan et al., 2020), and found that several transcripts are differentially regulated in both mice model and d30 after ET-1 treatment compared to CMM. These transcripts included Nppa and those encoding ETC subunits (FIG. 21).

The attenuated response of ET-1 on hiPSC-CMs matured on CMM for key characteristics of cardiac function: metabolism (energetics and redox), calcium handling and electrophysiology was confirmed. ET-1 treatment significantly increased both OxPhos and glycolysis on d30, but the levels of OxPhos was still lower than cells on CMM (FIG. 7*d*). After ET-1 treatment, cells on d30 exhibited increase in FAO, while CMM exhibited an opposite effect (FIG. 7*e*). Although respiratory control ratio (state 3 (active) respiration to state 4 (basal) respiration) was higher in CMM, it was not affected upon acute ET-1 treatment (FIG. 7*f*). Taken together, upon ET-1 treatment, CMM exhibited metabolic response of slight increase in glycolysis, with reduction in FAO, modest response to induction of pathological hypertrophy (de las Fuentes et al., 2003; Kolwicz and Tian, 2011; Lopaschuk et al., 2010). roGFP2 after $H_2O_2$ treatment showed d30 cells have reduced oxidative stress handling with ET-1, while it was unperturbed in CMM (FIG. 7*g*). $Ca^{2+}$ levels showed increase in peak amplitude on d30 with ET-1, but no significant effect on CMM (FIG. 7*h*), with increased $Ca^{2+}$ delay in both conditions, primarily by an increase in the diastolic calcium levels for CMM upon ET-1 stimulation (FIG. 7*i*-j). Finally, a decrease in beating frequency (FIG. 7*k*) and increase in action potential duration (FIG. 7*l*), for both d30 and CMM was found. Together, these data, along with the other Examples which established the increased maturation of cardiomyocytes on CMM, show that physiologically intact matrix and the resultant cardiomyocyte state can attenuate the pathological manifestation of endothelin treatment, particularly withstanding the disruption in metabolism, and redox handling, while electrophysiological effects of the treatment continue to manifest. Conversely, these data show that disrupted matrix architecture due to hypertrophic remodeling possibly contribute to the disease progression itself.

REFERENCES

1. Afzal, J., Chan, A., Karakas, M. F., Woldemichael, K., Vakrou, S., Guan, Y., Rathmell, J., Wahl, R., Pomper, M., Foster, D. B., et al. (2017). Cardiosphere-Derived Cells Demonstrate Metabolic Flexibility That Is Influenced by Adhesion Status. JACC Basic Transl Sci 2, 543-560.

2. Ahmed, R. E., Anzai, T., Chanthra, N., and Uosaki, H. (2020). A Brief Review of Current Maturation Methods for Human Induced Pluripotent Stem Cells-Derived Cardiomyocytes. Front Cell Dev Biol 8, 178.
3. Akhmedov, M., LeNail, A., Bertoni, F., Kwee, I., Fraenkel, E., and Montemanni, R. (2017). A Fast Prize-Collecting Steiner Forest Algorithm for Functional Analyses in Biological Networks. Lect Notes Comput Sc 10335, 263-276.
4. Aquilano, K., Baldelli, S., and Ciriolo, M. R. (2014). Glutathione: new roles in redox signaling for an old antioxidant. Front Pharmacol 5, 196.
5. Aratyn-Schaus, Y., Oakes, P. W., Stricker, J., Winter, S. P., and Gardel, M. L. (2010). Preparation of complaint matrices for quantifying cellular contraction. J Vis Exp.
6. Archer, C. R., Robinson, E. L., Drawnel, F. M., and Roderick, H. L. (2017). Endothelin-1 promotes hypertrophic remodelling of cardiac myocytes by activating sustained signalling and transcription downstream of endothelin type A receptors. Cell Signal 36, 240-254.
7. Ayad, N. M. E., Kaushik, S., and Weaver, V. M. (2019). Tissue mechanics, an important regulator of development and disease. Philos Trans R Soc Lond B Biol Sci 374, 20180215.
8. Barbuti, A., Benzoni, P., Campostrini, G., and Dell'Era, P. (2016). Human derived cardiomyocytes: A decade of knowledge after the discovery of induced pluripotent stem cells. Developmental dynamics: an official publication of the American Association of Anatomists 245, 1145-1158.
9. Barth, E., Stammler, G., Speiser, B., and Schaper, J. (1992). Ultrastructural quantitation of mitochondria and myofilaments in cardiac muscle from 10 different animal species including man. Journal of molecular and cellular cardiology 24, 669-681.
10. Bedada, F. B., Wheelwright, M., and Metzger, J. M. (2016). Maturation status of sarcomere structure and function in human iPSC-derived cardiac myocytes. Biochim Biophys Acta 1863, 1829-1838.
11. Bers, D. M. (2002). Cardiac excitation-contraction coupling. Nature 415, 198-205.
12. Bienstock, D., Goemans, M. X., Simchilevi, D., and Williamson, D. (1993). A Note on the Prize Collecting Traveling Salesman Problem. Math Program 59, 413-420.
13. Burgoyne, J. R., Mongue-Din, H., Eaton, P., and Shah, A. M. (2012). Redox signaling in cardiac physiology and pathology. Circ Res 111, 1091-1106.
14. Burridge, P. W., Matsa, E., Shukla, P., Lin, Z. C., Churko, J. M., Ebert, A. D., Lan, F., Diecke, S., Huber, B., Mordwinkin, N. M., et al. (2014). Chemically defined generation of human cardiomyocytes. Nature methods 11, 855-860.
15. Carson, D., Hnilova, M., Yang, X., Nemeth, C. L., Tsui, J. H., Smith, A. S., Jiao, A., Regnier, M., Murry, C. E., Tamerler, C., et al. (2016). Nanotopography-Induced Structural Anisotropy and Sarcomere Development in Human Cardiomyocytes Derived from Induced Pluripotent Stem Cells. ACS Appl Mater Interfaces 8, 21923-21932.
16. Caulfield, J. B., and Janicki, J. S. (1997). Structure and function of myocardial fibrillar collagen. Technol Health Care 5, 95-113.
17. Chen, T. W., Wardill, T. J., Sun, Y., Pulver, S. R., Renninger, S. L., Baohan, A., Schreiter, E. R., Kerr, R. A., Orger, M. B., Jayaraman, V., et al. (2013). Ultrasensitive fluorescent proteins for imaging neuronal activity. Nature 499, 295-300.
18. Cho, G. S., Lee, D. I., Tampakakis, E., Murphy, S., Andersen, P., Uosaki, H., Chelko, S., Chakir, K., Hong, I., Seo, K., et al. (2017). Neonatal Transplantation Confers Maturation of PSC-Derived Cardiomyocytes Conducive to Modeling Cardiomyopathy. Cell Rep 18, 571-582.
19. Choi, J. S., Smith, A. S. T., Williams, N. P., Matsubara, T., Choi, M., Kim, J. W., Kim, H. J., Choi, S., and Kim, D. H. (2020). Nanopatterned Nafion microelectrode arrays for in vitro cardiac electrophysiology. Adv Funct Mater 30.
20. Choy, J. Y., Boon, P. L., Bertin, N., and Fullwood, M. J. (2015). A resource of ribosomal RNA-depleted RNA-Seq data from different normal adult and fetal human tissues. Sci Data 2, 150063.
21. Correia, C., Koshkin, A., Duarte, P., Hu, D., Teixeira, A., Domian, I., Serra, M., and Alves, P. M. (2017). Distinct carbon sources affect structural and functional maturation of cardiomyocytes derived from human pluripotent stem cells. Scientific reports 7, 8590.
22. Crowder, S. W., Liang, Y., Rath, R., Park, A. M., Maltais, S., Pintauro, P. N., Hofmeister, W., Lim, C. C., Wang, X., and Sung, H. J. (2013). Poly(epsilon-caprolactone)-carbon nanotube composite scaffolds for enhanced cardiac differentiation of human mesenchymal stem cells. Nanomedicine (Lond) 8, 1763-1776.
23. de las Fuentes, L., Herrero, P., Peterson, L. R., Kelly, D. P., Gropler, R. J., and Davila-Roman, V. G. (2003). Myocardial fatty acid metabolism: independent predictor of left ventricular mass in hypertensive heart disease. Hypertension 41, 83-87.
24. Dias, T. P., Pinto, S. N., Santos, J. I., Fernandes, T. G., Fernandes, F., Diogo, M. M., Prieto, M., and Cabral, J. M. S. (2018). Biophysical study of human induced Pluripotent Stem Cell-Derived cardiomyocyte structural maturation during long-term culture. Biochem Biophys Res Commun 499, 611-617.
25. Doenst, T., Nguyen, T. D., and Abel, E. D. (2013). Cardiac metabolism in heart failure: implications beyond ATP production. Circ Res 113, 709-724.
26. Feaster, T. K., Cadar, A. G., Wang, L., Williams, C. H., Chun, Y. W., Hempel, J. E., Bloodworth, N., Merryman, W. D., Lim, C. C., Wu, J. C., et al. (2015). Matrigel Mattress: A Method for the Generation of Single Contracting Human-Induced Pluripotent Stem Cell-Derived Cardiomyocytes. Circ Res 117, 995-1000.
27. Feyen, D. A. M., McKeithan, W. L., Bruyneel, A. A. N., Spiering, S., Hormann, L., Ulmer, B., Zhang, H., Briganti, F., Schweizer, M., Hegyi, B., et al. (2020). Metabolic Maturation Media Improve Physiological Function of Human iPSC-Derived Cardiomyocytes. Cell Rep 32, 107925.
28. Fischer, R. S., Myers, K. A., Gardel, M. L., and Waterman, C. M. (2012). Stiffness-controlled three-dimensional extracellular matrices for high-resolution imaging of cell behavior. Nat Protoc 7, 2056-2066.
29. Friedman, C. E., Nguyen, Q., Lukowski, S. W., Helfer, A., Chiu, H. S., Miklas, J., Levy, S., Suo, S., Han, J. J., Osteil, P., et al. (2018). Single-Cell Transcriptomic Analysis of Cardiac Differentiation from Human PSCs Reveals HOPX-Dependent Cardiomyocyte Maturation. Cell Stem Cell 23, 586-598 e588.
30. Gintant, G., Burridge, P., Gepstein, L., Harding, S., Herron, T., Hong, C., Jalife, J., and Wu, J. C. (2019). Use of Human Induced Pluripotent Stem Cell-Derived Cardiomyocytes in Preclinical Cancer Drug Cardiotoxicity Testing: A Scientific Statement From the American Heart Association. Circ Res 125, e75-e92.

31. Goversen, B., van der Heyden, M. A. G., van Veen, T. A. B., and de Boer, T. P. (2018). The immature electrophysiological phenotype of iPSC-CMs still hampers in vitro drug screening: Special focus on IK1. Pharmacol Ther 183, 127-136.

32. Guo, Y., and Pu, W. T. (2020). Cardiomyocyte Maturation: New Phase in Development. Circ Res 126, 1086-1106.

33. Gutscher, M., Pauleau, A. L., Marty, L., Brach, T., Wabnitz, G. H., Samstag, Y., Meyer, A. J., and Dick, T. P. (2008). Real-time imaging of the intracellular glutathione redox potential. Nature methods 5, 553-559.

34. Harris, M. A., Clark, J., Ireland, A., Lomax, J., Ashburner, M., Foulger, R., Eilbeck, K., Lewis, S., Marshall, B., Mungall, C., et al. (2004). The Gene Ontology (GO) database and informatics resource. Nucleic Acids Res 32, D258-261.

35. He, C., Hu, H., Wilson, K. D., Wu, H., Feng, J., Xia, S., Churko, J., Qu, K., Chang, H. Y., and Wu, J. C. (2016). Systematic Characterization of Long Noncoding RNAs Reveals the Contrasting Coordination of Cis- and Trans-Molecular Regulation in Human Fetal and Adult Hearts. Circ Cardiovasc Genet 9, 110-118.

36. Hom, J. R., Quintanilla, R. A., Hoffman, D. L., de Mesy Bentley, K. L., Molkentin, J. D., Sheu, S. S., and Porter, G. A., Jr. (2011). The permeability transition pore controls cardiac mitochondrial maturation and myocyte differentiation. Dev Cell 21, 469-478.

37. Hu, D., Linders, A., Yamak, A., Correia, C., Kijlstra, J. D., Garakani, A., Xiao, L., Milan, D. J., van der Meer, P., Serra, M., et al. (2018). Metabolic Maturation of Human Pluripotent Stem Cell-Derived Cardiomyocytes by Inhibition of HIF1 alpha and LDHA. Circ Res 123, 1066-1079.

38. Hubbi, M. E., Kshitiz, Gilkes, D. M., Rey, S., Wong, C. C., Luo, W., Kim, D. H., Dang, C. V., Levchenko, A., and Semenza, G. L. (2013). A nontranscriptional role for HIF-1alpha as a direct inhibitor of DNA replication. Sci Signal 6, ra10.

39. Huntley, R. P., Sawford, T., Mutowo-Meullenet, P., Shypitsyna, A., Bonilla, C., Martin, M. J., and O'Donovan, C. (2015). The GOA database: gene Ontology annotation updates for 2015. Nucleic Acids Res 43, D1057-1063.

40. Ingwall, J. S. (2009). Energy metabolism in heart failure and remodelling. Cardiovasc Res 81, 412-419.

41. Jin, L., Han, Z., Platisa, J., Wooltorton, J. R., Cohen, L. B., and Pieribone, V. A. (2012). Single action potentials and subthreshold electrical events imaged in neurons with a fluorescent protein voltage probe. Neuron 75, 779-785.

42. Jung, J. P., Hu, D., Domian, I. J., and Ogle, B. M. (2015). An integrated statistical model for enhanced murine cardiomyocyte differentiation via optimized engagement of 3D extracellular matrices. Scientific reports 5, 18705.

43. Kaiser, N. J., Kant, R. J., Minor, A. J., and Coulombe, K. L. K. (2019). Optimizing Blended Collagen-Fibrin Hydrogels for Cardiac Tissue Engineering with Human iPSC-derived Cardiomyocytes. ACS biomaterials science & engineering 5, 887-899.

44. Kannan, M., Vasan, G., Huang, C., Haziza, S., Li, J. Z., Iran, H., Schnitzer, M. J., and Pieribone, V. A. (2018). Fast, in vivo voltage imaging using a red fluorescent indicator. Nature methods 15, 1108-1116.

45. Karakikes, I., Ameen, M., Termglinchan, V., and Wu, J. C. (2015). Human induced pluripotent stem cell-derived cardiomyocytes: insights into molecular, cellular, and functional phenotypes. Circ Res 117, 80-88.

46. Kedaigle A, and E., F. (2018). Discovering altered regulation and signaling through network-based integration of transcriptomic, epigenomic and proteomic tumor data. Methods in Molecular Biology.

47. Keung, W., Boheler, K. R., and Li, R. A. (2014). Developmental cues for the maturation of metabolic, electrophysiological and calcium handling properties of human pluripotent stem cell-derived cardiomyocytes. Stem Cell Res Ther 5, 17.

48. Khan, M., Xu, Y., Hua, S., Johnson, J., Belevych, A., Janssen, P. M., Gyorke, S., Guan, J., and Angelos, M. G. (2015). Evaluation of Changes in Morphology and Function of Human Induced Pluripotent Stem Cell Derived Cardiomyocytes (HiPSC-CMs) Cultured on an Aligned-Nanofiber Cardiac Patch. PLoS One 10, e0126338.

49. Kim, D. H., Kshitiz, Smith, R. R., Kim, P., Ahn, E. H., Kim, H. N., Marban, E., Suh, K. Y., and Levchenko, A. (2012). Nanopatterned cardiac cell patches promote stem cell niche formation and myocardial regeneration. Integr Biol (Camb) 4, 1019-1033.

50. Kim, H. E., Dalal, S. S., Young, E., Legato, M. J., Weisfeldt, M. L., and D'Armiento, J. (2000). Disruption of the myocardial extracellular matrix leads to cardiac dysfunction. J Clin Invest 106, 857-866.

51. Knoll, S. G., Ali, M. Y., and Saif, M. T. (2014). A novel method for localizing reporter fluorescent beads near the cell culture surface for traction force microscopy. J Vis Exp, 51873. 52. Kolberg, L., Raudvere, U., Kuzmin, I., Vilo, J., and Peterson, H. (2020). gprofiler2—an R package for gene list functional enrichment analysis and namespace conversion toolset g:Profiler. F1000Res 9.

53. Kolwicz, S. C., Jr., and Tian, R. (2011). Glucose metabolism and cardiac hypertrophy. Cardiovasc Res 90, 194-201.

54. Kshitiz, Afzal, J., Kim, D. H., and Levchenko, A. (2014). Concise review: Mechanotransduction via p190RhoGAP regulates a switch between cardiomyogenic and endothelial lineages in adult cardiac progenitors. Stem Cells 32, 1999-2007.

55. Kshitiz, Hubbi, M. E., Ahn, E. H., Downey, J., Afzal, J., Kim, D. H., Rey, S., Chang, C., Kundu, A., Semenza, G. L., et al. (2012). Matrix rigidity controls endothelial differentiation and morphogenesis of cardiac precursors. Sci Signal 5, ra41.

56. Kumar, N., Sridharan, D., Palaniappan, A., Dougherty, J. A., Czirok, A., Isai, D. G., Mergaye, M., Angelos, M. G., Powell, H. M., and Khan, M. (2020). Scalable Biomimetic Coaxial Aligned Nanofiber Cardiac Patch: A Potential Model for "Clinical Trials in a Dish". Front Bioeng Biotechnol 8, 567842.

57. Lewandowski, J., Rozwadowska, N., Kolanowski, T. J., Malcher, A., Zimna, A., Rugowska, A., Fiedorowicz, K., Labedz, W., Kubaszewski, L., Chojnacka, K., et al. (2018). The impact of in vitro cell culture duration on the maturation of human cardiomyocytes derived from induced pluripotent stem cells of myogenic origin. Cell Transplant 27, 1047-1067.

58. Liu, J., Laksman, Z., and Backx, P. H. (2016). The electrophysiological development of cardiomyocytes. Adv Drug Deliv Rev 96, 253-273.

59. Liu, J., Lieu, D. K., Siu, C. W., Fu, J. D., Tse, H. F., and Li, R. A. (2009). Facilitated maturation of $Ca^{2+}$ handling properties of human embryonic stem cell-derived cardiomyocytes by calsequestrin expression. Am J Physiol Cell Physiol 297, C152-159.

60. Liu, Q., Tian, S., Zhao, C., Chen, X., Lei, I., Wang, Z., and Ma, P. X. (2015). Porous nanofibrous poly(L-lactic acid) scaffolds supporting cardiovascular progenitor cells for cardiac tissue engineering. Acta Biomater 26, 105-114.
61. Liu, W., Acin-Perez, R., Geghman, K. D., Manfredi, G., Lu, B., and Li, C. (2011). Pink1 regulates the oxidative phosphorylation machinery via mitochondrial fission. Proc Natl Acad Sci USA 108, 12920-12924.
62. Lopaschuk, G. D., and Jaswal, J. S. (2010). Energy metabolic phenotype of the cardiomyocyte during development, differentiation, and postnatal maturation. J Cardiovasc Pharmacol 56, 130-140.
63. Lopaschuk, G. D., Ussher, J. R., Folmes, C. D., Jaswal, J. S., and Stanley, W. C. (2010). Myocardial fatty acid metabolism in health and disease. Physiol Rev 90, 207-258.
64. Lopez-Acosta, O., de Los Angeles Fortis-Barrera, M., Barrios-Maya, M. A., Ramirez, A. R., Aguilar, F. J. A., and El-Hafidi, M. (2018). Reactive Oxygen Species from NADPH Oxidase and Mitochondria Participate in the Proliferation of Aortic Smooth Muscle Cells from a Model of Metabolic Syndrome. Oxidative medicine and cellular longevity 2018, 5835072.
65. Lundy, S. D., Zhu, W. Z., Regnier, M., and Laflamme, M. A. (2013). Structural and functional maturation of cardiomyocytes derived from human pluripotent stem cells. Stem Cells Dev 22, 1991-2002.
66. Lunt, S. Y., and Vander Heiden, M. G. (2011). Aerobic glycolysis: meeting the metabolic requirements of cell proliferation. Annual review of cell and developmental biology 27, 441-464.
67. Madamanchi, N. R., and Runge, M. S. (2013). Redox signaling in cardiovascular health and disease. Free Radic Biol Med 61, 473-501.
68. Mamidi, A., Prawiro, C., Seymour, P. A., de Lichtenberg, K. H., Jackson, A., Serup, P., and Semb, H. (2018). Mechanosignalling via integrins directs fate decisions of pancreatic progenitors. Nature 564, 114-118.
69. Mammoto, T., and Ingber, D. E. (2010). Mechanical control of tissue and organ development. Development 137, 1407-1420.
70. Marian, A. J., and Braunwald, E. (2017). Hypertrophic Cardiomyopathy: Genetics, Pathogenesis, Clinical Manifestations, Diagnosis, and Therapy. Circ Res 121, 749-770.
71. McLellan, M. A., Skelly, D. A., Dona, M. S. I., Squiers, G. T., Farrugia, G. E., Gaynor, T. L., Cohen, C. D., Pandey, R., Diep, H., Vinh, A., et al. (2020). High-Resolution Transcriptomic Profiling of the Heart During Chronic Stress Reveals Cellular Drivers of Cardiac Fibrosis and Hypertrophy. Circulation 142, 1448-1463.
72. Meyer, A. J., and Dick, T. P. (2010). Fluorescent protein-based redox probes. Antioxid Redox Signal 13, 621-650.
73. Paige, S. L., Plonowska, K., Xu, A., and Wu, S. M. (2015). Molecular regulation of cardiomyocyte differentiation. Circ Res 116, 341-353.
74. Passier, R., Orlova, V., and Mummery, C. (2016). Complex Tissue and Disease Modeling using hiPSCs. Cell Stem Cell 18, 309-321.
75. Patra, C., Diehl, F., Ferrazzi, F., van Amerongen, M. J., Novoyatleva, T., Schaefer, L., Muhlfeld, C., Jungblut, B., and Engel, F. B. (2011). Nephronectin regulates atrioventricular canal differentiation via Bmp4-Has2 signaling in zebrafish. Development 138, 4499-4509.
76. Patra, C., Ricciardi, F., and Engel, F. B. (2012). The functional properties of nephronectin: an adhesion molecule for cardiac tissue engineering. Biomaterials 33, 4327-4335.
77. Phillips, N. R., Sprouse, M. L., and Roby, R. K. (2014). Simultaneous quantification of mitochondrial DNA copy number and deletion ratio: a multiplex real-time PCR assay. Scientific reports 4, 3887.
78. Picard, M., Taivassalo, T., Gouspillou, G., and Hepple, R. T. (2011). Mitochondria: isolation, structure and function. J Physiol 589, 4413-4421.
79. Ronaldson-Bouchard, K., Ma, S. P., Yeager, K., Chen, T., Song, L., Sirabella, D., Morikawa, K., Teles, D., Yazawa, M., and Vunjak-Novakovic, G. (2018). Advanced maturation of human cardiac tissue grown from pluripotent stem cells. Nature 556, 239-243.
80. Rossi, M. A. (1998). Pathologic fibrosis and connective tissue matrix in left ventricular hypertrophy due to chronic arterial hypertension in humans. J Hypertens 16, 1031-1041.
81. Ruan, J. L., Tulloch, N. L., Razumova, M. V., Saiget, M., Muskheli, V., Pabon, L., Reinecke, H., Regnier, M., and Murry, C. E. (2016). Mechanical Stress Conditioning and Electrical Stimulation Promote Contractility and Force Maturation of Induced Pluripotent Stem Cell-Derived Human Cardiac Tissue. Circulation 134, 1557-1567.
82. Sabass, B., Gardel, M. L., Waterman, C. M., and Schwarz, U. S. (2008). High resolution traction force microscopy based on experimental and computational advances. Biophys J 94, 207-220.
83. Salabei, J. K., Gibb, A. A., and Hill, B. G. (2014). Comprehensive measurement of respiratory activity in permeabilized cells using extracellular flux analysis. Nat Protoc 9, 421-438.
84. Santos, C. X., Anilkumar, N., Zhang, M., Brewer, A. C., and Shah, A. M. (2011). Redox signaling in cardiac myocytes. Free Radic Biol Med 50, 777-793.
85. Sartiani, L., Bettiol, E., Stillitano, F., Mugelli, A., Cerbai, E., and Jaconi, M. E. (2007). Developmental changes in cardiomyocytes differentiated from human embryonic stem cells: a molecular and electrophysiological approach. Stem Cells 25, 1136-1144.
86. Schwach, V., and Passier, R. (2019). Native cardiac environment and its impact on engineering cardiac tissue. Biomaterials science 7, 3566-3580.
87. Schwer, B., and Verdin, E. (2008). Conserved metabolic regulatory functions of sirtuins. Cell metabolism 7, 104-112.
88. Sewanan, L. R., Schwan, J., Kluger, J., Park, J., Jacoby, D. L., Qyang, Y., and Campbell, S. G. (2019). Extracellular Matrix From Hypertrophic Myocardium Provokes Impaired Twitch Dynamics in Healthy Cardiomyocytes. JACC Basic Transl Sci 4, 495-505.
89. Shadrin, I. Y., Allen, B. W., Qian, Y., Jackman, C. P., Carlson, A. L., Juhas, M. E., and Bursac, N. (2017). Cardiopatch platform enables maturation and scale-up of human pluripotent stem cell-derived engineered heart tissues. Nat Commun 8, 1825.
90. Shi, M., Tien, N. T., de Haan, L., Louisse, J., Rietjens, I., and Bouwmeester, H. (2020). Evaluation of in vitro models of stem cell-derived cardiomyocytes to screen for potential cardiotoxicity of chemicals. Toxicol In Vitro 67, 104891.
91. Silva, A. C., Pereira, C., Fonseca, A., Pinto-do, O. P., and Nascimento, D. S. (2020). Bearing My Heart: The Role of Extracellular Matrix on Cardiac Development, Homeostasis, and Injury Response. Front Cell Dev Biol 8, 621644.

92. Slenter, D. N., Kutmon, M., Hanspers, K., Riutta, A., Windsor, J., Nunes, N., Melius, J., Cirillo, E., Coort, S. L., Digles, D., et al. (2018). WikiPathways: a multifaceted pathway database bridging metabolomics to other omics research. Nucleic Acids Res 46, D661-D667.
93. Smith, A. S. T., Yoo, H., Yi, H., Ahn, E. H., Lee, J. H., Shao, G., Nagornyak, E., Laflamme, M. A., Murry, C. E., and Kim, D. H. (2017). Micro- and nano-patterned conductive graphene-PEG hybrid scaffolds for cardiac tissue engineering. Chem Commun (Camb) 53, 7412-7415.
94. Stanley, W. C., Recchia, F. A., and Lopaschuk, G. D. (2005). Myocardial substrate metabolism in the normal and failing heart. Physiol Rev 85, 1093-1129.
95. Stark, C., Breitkreutz, B. J., Reguly, T., Boucher, L., Breitkreutz, A., and Tyers, M. (2006). BioGRID: a general repository for interaction datasets. Nucleic Acids Res 34, D535-539.
96. Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc Natl Acad Sci USA 102, 15545-15550.
97. Sung, T. C., Su, H. C., Ling, Q. D., Kumar, S. S., Chang, Y., Hsu, S. T., and Higuchi, A. (2020). Efficient differentiation of human pluripotent stem cells into cardiomyocytes on cell sorting thermoresponsive surface. Biomaterials 253, 120060.
98. Tanner, L. B., Goglia, A. G., Wei, M. H., Sehgal, T., Parsons, L. R., Park, J. O., White, E., Toettcher, J. E., and Rabinowitz, J. D. (2018). Four Key Steps Control Glycolytic Flux in Mammalian Cells. Cell systems 7, 49-62 e48.
99. Thielicke, W., and Eize J. Stamhuis (2014). PIVlab-Towards User-Friendly, Affordable and Accurate Digital Particle Image Velocimetry in MATLAB. Journal of Open Research Software 2.
100. Thompson, W. R., Nadal-Ginard, B., and Mandavi, V. (1991). A MyoD1-independent muscle-specific enhancer controls the expression of the beta-myosin heavy chain gene in skeletal and cardiac muscle cells. J Biol Chem 266, 22678-22688.
101. Tohyama, S., Hattori, F., Sano, M., Hishiki, T., Nagahata, Y., Matsuura, T., Hashimoto, H., Suzuki, T., Yamashita, H., Satoh, Y., et al. (2013). Distinct metabolic flow enables large-scale purification of mouse and human pluripotent stem cell-derived cardiomyocytes. Cell Stem Cell 12, 127-137.
102. Tu, C., Chao, B. S., and Wu, J. C. (2018). Strategies for Improving the Maturity of Human Induced Pluripotent Stem Cell-Derived Cardiomyocytes. Circ Res 123, 512-514.
103. Uosaki, H., Cahan, P., Lee, D. I., Wang, S., Miyamoto, M., Fernandez, L., Kass, D. A., and Kwon, C. (2015). Transcriptional Landscape of Cardiomyocyte Maturation. Cell Rep 13, 1705-1716.
104. Vining, K. H., and Mooney, D. J. (2017). Mechanical forces direct stem cell behaviour in development and regeneration. Nat Rev Mol Cell Biol 18, 728-742.
105. Wang, Y. L., and Pelham, R. J., Jr. (1998). Preparation of a flexible, porous polyacrylamide substrate for mechanical studies of cultured cells. Methods Enzymol 298, 489-496.
106. Weinberger, F., Mannhardt, I., and Eschenhagen, T. (2017). Engineering Cardiac Muscle Tissue: A Maturating Field of Research. Circ Res 120, 1487-1500.
107. Wixon, J., and Kell, D. (2000). The Kyoto encyclopedia of genes and genomes-KEGG. Yeast 17, 48-55.
108. Wrighton, P. J., Klim, J. R., Hernandez, B. A., Koonce, C. H., Kamp, T. J., and Kiessling, L. L. (2014). Signals from the surface modulate differentiation of human pluripotent stem cells through glycosaminoglycans and integrins. Proc Natl Acad Sci USA 111, 18126-18131.
109. Yang, X., Pabon, L., and Murry, C. E. (2014). Engineering adolescence: maturation of human pluripotent stem cell-derived cardiomyocytes. Circ Res 114, 511-523.
110. Yu, J., Lee, A. R., Lin, W. H., Lin, C. W., Wu, Y. K., and Tsai, W. B. (2014). Electrospun PLGA fibers incorporated with functionalized biomolecules for cardiac tissue engineering. Tissue Eng Part A 20, 1896-1907.
111. Zhao, X., Cai, A., Peng, Z., Liang, W., Xi, H., Li, P., Chen, G., Yu, J., and Chen, L. (2019). JS-K induces reactive oxygen species-dependent anti-cancer effects by targeting mitochondria respiratory chain complexes in gastric cancer. Journal of cellular and molecular medicine 23, 2489-2504.

SEQUENCE LISTING

```
Sequence total quantity: 14
SEQ ID NO: 1            moltype = DNA  length = 21
FEATURE                 Location/Qualifiers
source                  1..21
                        mol_type = other DNA
                        organism = synthetic construct
SEQUENCE: 1
ctaaatagcc cacacgttcc c                                            21

SEQ ID NO: 2            moltype = DNA  length = 19
FEATURE                 Location/Qualifiers
source                  1..19
                        mol_type = other DNA
                        organism = synthetic construct
SEQUENCE: 2
agagctcccg tgagtggtt                                               19

SEQ ID NO: 3            moltype = DNA  length = 20
FEATURE                 Location/Qualifiers
source                  1..20
                        mol_type = other DNA
```

```
                       organism = synthetic construct
SEQUENCE: 3
catcacgatg gatcacaggt                                              20

SEQ ID NO: 4           moltype = DNA  length = 20
FEATURE                Location/Qualifiers
source                 1..20
                       mol_type = other DNA
                       organism = synthetic construct
SEQUENCE: 4
ctgttcccca accttttcct                                              20

SEQ ID NO: 5           moltype = DNA  length = 20
FEATURE                Location/Qualifiers
source                 1..20
                       mol_type = other DNA
                       organism = synthetic construct
SEQUENCE: 5
ccatgattgt gaggggtagg                                              20

SEQ ID NO: 6           moltype = DNA  length = 18
FEATURE                Location/Qualifiers
source                 1..18
                       mol_type = other DNA
                       organism = synthetic construct
SEQUENCE: 6
gaccccctaa caaccccc                                                18

SEQ ID NO: 7           moltype = DNA  length = 27
FEATURE                Location/Qualifiers
source                 1..27
                       mol_type = other DNA
                       organism = synthetic construct
SEQUENCE: 7
gctgggtagc tctaaacaat gtattca                                      27

SEQ ID NO: 8           moltype = DNA  length = 28
FEATURE                Location/Qualifiers
source                 1..28
                       mol_type = other DNA
                       organism = synthetic construct
SEQUENCE: 8
ccatgtacta acaaatgtct aaaatggt                                     28

SEQ ID NO: 9           moltype = DNA  length = 16
FEATURE                Location/Qualifiers
source                 1..16
                       mol_type = other DNA
                       organism = synthetic construct
SEQUENCE: 9
cagcagccta ttctgc                                                  16

SEQ ID NO: 10          moltype = AA  length = 5
FEATURE                Location/Qualifiers
source                 1..5
                       mol_type = protein
                       organism = synthetic construct
SEQUENCE: 10
GRGDS                                                              5

SEQ ID NO: 11          moltype = AA  length = 6
FEATURE                Location/Qualifiers
source                 1..6
                       mol_type = protein
                       organism = synthetic construct
SEQUENCE: 11
GFOGER                                                             6

SEQ ID NO: 12          moltype = AA  length = 6
FEATURE                Location/Qualifiers
source                 1..6
                       mol_type = protein
                       organism = synthetic construct
SEQUENCE: 12
GFPGER                                                             6

SEQ ID NO: 13          moltype = AA  length = 565
FEATURE                Location/Qualifiers
source                 1..565
```

-continued

```
                        mol_type = protein
                        organism = synthetic construct
SEQUENCE: 13
MDFLLALVLV SSLYLQAAAE FDGRWPRQIV SSIGLCRYGG RIDCCWGWAR QSWGQCQPVC  60
QPRCKHGECI GPNKCKCHPG YAGKTCNQDL NECGLKPRPC KHRCMNTYGS YKCYCLNGYM  120
LMPDGSCSSA LTCSMANCQY GCDVVKGQIR CQCPSPGLQL APDGRTCVDV DECATGRASC  180
PRFRQCVNTF GSYICKCHKG FDLMYIGGKY QCHDIDECSL GQYQCSSFAR CYNIRGSYKC  240
KCKEGYQGDG LTCVYIPKVM IEPSGPIHVP KGNGTILKGD TGNNNWIPDV GSTWWPPKTP  300
YIPPIITNRP TSKPTTRPTP KPTPIPTPPP PPPLPTELRT PLPPTTPERP TTGLTTIAPA  360
ASTPPGGITV DNRVQTDPQK PRGDVFIPRQ PSNDLFEIFE IERGVSADDE AKDDPGVLVH  420
SCNFDHGLCG WIREKDNDLH WEPIRDPAGG QYLTVSAAKA PGGKAARLVL PLGRLMHSGD  480
LCLSFRHKVT GLHSGTLQVF VRKHGAHGAA LWGRNGGHGW RQTQITLRGA DIKSVVFKGE  540
KRRGHTGEIG LDDVSLKKGH CSEER                                      565

SEQ ID NO: 14           moltype = AA  length = 5
FEATURE                 Location/Qualifiers
source                  1..5
                        mol_type = protein
                        organism = synthetic construct
SEQUENCE: 14
GFOGR                                                            5
```

We claim:

1. A construct, comprising:

(a) a patterned scaffold, wherein the patterned scaffold comprises a polymeric hydrogel substrate comprising a plurality of nanowrinkles, wherein the nanowrinkles comprise branched folds directionally aligned over a centimeter length scale, wherein the polymeric substrate has a viscoelasticity between about 15 kPa and about 100kPa;

(b) one or more cardiac matrix ligands conjugated to the patterned scaffold, wherein the one or more cardiac matrix ligands comprises 1, 2, 3, 4 or more of nephronectin (SEQ ID NO: 13), GRGDS (SEQ ID NO: 10), GFOGER (SEQ ID NO: 11), GFPGER (SEQ ID NO: 12) and/or other peptides containing one or more RGD motifs.

2. The construct of claim 1, wherein the construct comprises nephronectin (SEQ ID NO: 13), RGD, and GFOGER (SEQ ID NO: 11) conjugated to the patterned scaffold.

3. The construct of claim 2, wherein the nephronectin (SEQ ID NO: 13), RGD, and GFOGER (SEQ ID NO: 11) are present in about an equimolar ratio.

4. The construct of claim 1, wherein the construct further comprises laminin conjugated to the patterned scaffold.

5. The construct of claim 1, wherein the polymeric hydrogel substrate comprises aligned wrinkle ridges, wherein the aligned wrinkle ridges are arranged in one or more continuous and ordered patterns.

6. The construct of claim 1, wherein a height of ridges ranges between about 10 nm and about 4 μm, and optionally the ridges are all of approximately the same height over the entire scaffold, or of approximately the same height in each discrete section of the scaffold.

7. The construct of claim 1, wherein valley to valley distances and/or ridge peak to ridge peak distances of between about 400 nm and about 3 μm.

8. The construct of claim 1, wherein the construct comprises fluorescent beads.

9. The construct of claim 1, wherein the patterned scaffold comprises a polyacrylamide (PA) or polyethylene glycol (PEG) hydrogel, poly lactic-co-glycolic acid (PLGA), polyurethane (PUA), polyacrylate (PA) or their chemical branch derivatives.

10. The construct of claim 1, wherein the patterned scaffold comprises a polyacrylamide (PA) hydrogel having a rigidity of between about 16-24 kPa.

11. The construct of claim 10, wherein the polymeric hydrogel substrate binds to the one or more cardiac matrix ligands via covalent binding or functional group conjugation.

12. The construct of claim 1, further comprising cardiomyocytes or precursors thereof seeded on the construct.

13. The construct of claim 12, wherein the cardiomyocytes or precursors thereof comprise induced pluripotent stem cell (iPSC) derived cardiomyocytes, human cardiomyocytes or precursors thereof, and/or electrochemically connected cardiomyocytes.

14. The construct of claim 1, further comprising cardiac fibroblasts or precursors thereof, endothelial cells, vascular smooth muscle cells and/or macrophages and/or other immune cells seeded on the construct.

15. The construct of claim 1, wherein the polymeric hydrogel substrate is capable of shrinking or expanding to achieve a desired feature size ranging from 0.1 μm to 10 μm.

16. The construct of claim 1, wherein the plurality of nanowrinkles comprises isotropic or non-aligned nanowrinkles capable of non-directional stretching, orthogonal stretching or circular stretching.

* * * * *